(12) United States Patent
Jiao et al.

(10) Patent No.: US 7,326,812 B2
(45) Date of Patent: Feb. 5, 2008

(54) ARYLSULFONAMIDOBENZYLIC COMPOUNDS

(75) Inventors: Xian Yun Jiao, San Mateo, CA (US); Frank Kayser, San Francisco, CA (US); Sharon McKendry, Redwood Shores, CA (US); Derek E. Piper, Foster City, CA (US); Andrew K. Shiau, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 93 days.

(21) Appl. No.: 11/333,958

(22) Filed: Jan. 17, 2006

(65) Prior Publication Data

US 2006/0122239 A1 Jun. 8, 2006

Related U.S. Application Data

(63) Continuation of application No. 10/354,922, filed on Jan. 29, 2003, now Pat. No. 7,071,358.

(60) Provisional application No. 60/353,497, filed on Jan. 30, 2002.

(51) Int. Cl.
C07C 311/15 (2006.01)

(52) U.S. Cl. .................. 564/92; 548/205; 548/250; 548/309.7; 548/335.5; 548/561

(58) Field of Classification Search ............ 564/92; 514/604; 548/205, 250, 309.7, 335.5, 561
See application file for complete search history.

(56) References Cited

U.S. PATENT DOCUMENTS

| | | | |
|---|---|---|---|
| 3,281,466 A | 10/1966 | Stecker et al. | |
| 3,405,177 A | 10/1968 | Jones et al. | |
| 4,093,742 A | 6/1978 | Neustadt | |
| 4,107,303 A | 8/1978 | Aldrich et al. | |
| 4,199,597 A | 4/1980 | Neustadt et al. | |
| 4,218,448 A | 8/1980 | Aldrich et al. | |
| 4,230,635 A | 10/1980 | Neustadt et al. | |
| 4,240,979 A | 12/1980 | Baumann et al. | |
| 4,251,534 A | 2/1981 | Aldrich et al. | |
| 4,251,659 A | 2/1981 | Aldrich et al. | |
| 4,267,193 A | 5/1981 | Neustadt et al. | |
| 5,883,106 A | 3/1999 | Stevens et al. | |
| 6,030,991 A | 2/2000 | Chan et al. | |
| 6,156,766 A | 12/2000 | Arita et al. | |
| 6,162,830 A | 12/2000 | Connor et al. | |
| 6,174,905 B1 | 1/2001 | Suzuki et al. | |
| 6,191,170 B1 | 2/2001 | Medina | |
| 6,197,798 B1 | 3/2001 | Fink et al. | |
| 6,201,013 B1 | 3/2001 | Bloom et al. | |
| 6,211,241 B1 | 4/2001 | Islam et al. | |
| 6,211,242 B1 | 4/2001 | Setoi et al. | |
| 6,214,880 B1 | 4/2001 | Houze | |
| 6,242,493 B1 | 6/2001 | Gareau et al. | |
| 6,316,503 B1 | 11/2001 | Li et al. | |
| 6,458,805 B2 | 10/2002 | Blok et al. | |
| 6,906,069 B1 | 6/2005 | Li et al. | |
| 2003/0220339 A1 | 11/2003 | Yun et al. | |
| 2003/0229093 A1 | 12/2003 | Yun et al. | |

FOREIGN PATENT DOCUMENTS

| | | |
|---|---|---|
| BE | 872.311 | 5/1979 |
| EP | 0 193 249 A2 | 9/1986 |
| EP | 1 919 542 A2 | 6/1999 |
| GB | 1 507 340 | 4/1978 |
| WO | WO00/46203 | 8/2000 |

OTHER PUBLICATIONS

Chkanikov et al. "Hexafluoroacetone and Methyl Trifluoropyruvate as Precursors of Modified Esters of n-acyl-n-phenyl-α-amino acids," *Bulletin of the Russian Academy of Sciences*, 41(8) Part 2 pp. 1415-1424., 1992.

Gilbert et al. "Perhalo Ketones—(VI) Aromatic Amino derivs, of the penhaloacetones," Database 'Online accession No. 16091fXP-002151155, Russian Abstract, 1965.

Miryan et al. "Derivatives of Pyridinecaroxylic acids. Synthesis and antiexudative Effect of Fluorinated Derivatives of Nicotinamide and Isonicotinamide," Database Chemabs 'Online! Chemical Abstract Service, Accession. No. 86:139798 XP-002151153; (1977), 11(1), 70-2 Russian Abstract.

Polishchuk et al. "Electron Paramagnetic Resonance Spectra of 2-arylpolyfluorisopropyl radicals," Database Chemabs 'Online! Chemical Abstract Service, Accession No. 91:4737 CA XP-002151154; (1979), (3), 659-661, Russian Abstract.

*Primary Examiner*—Shailendra Kumar
(74) *Attorney, Agent, or Firm*—Jones Day

(57) ABSTRACT

Arylsulfonamidobenzyl alcohols, amines and sulfonamides are provided which are useful in treating lipid disorders, metabolic diseases and cell-proliferative diseases.

9 Claims, No Drawings

ARYLSULFONAMIDOBENZYLIC COMPOUNDS

CROSS-REFERENCES TO RELATED APPLICATIONS

This application is a continuation of U.S. application Ser. No. 10/354,922, filed Jan. 29, 2003, now U.S. Pat. No. 7,071,358, which claims the benefit of Provisional Application Ser. No. 60/353,497 filed Jan. 30, 2002, the disclosures of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). Excess accumulation of cholesterol in the arterial walls can result in atherosclerosis, which is characterized by plaque formation. The plaques inhibit blood flow, promote clot formation and can ultimately cause heart attacks, stroke and claudication. Development of therapeutic agents for the treatment of atherosclerosis and other diseases associated with cholesterol metabolism has been focused on achieving a more complete understanding of the biochemical pathways involved. Most recently, liver X receptors (LXRs) were identified as key components in cholesterol homeostasis.

The LXRs were first identified as orphan members of the nuclear receptor superfamily whose ligands and functions were unknown. Two LXR proteins ($\alpha$ and $\beta$) are known to exist in mammals. The expression of LXR$\alpha$ is restricted, with the highest levels being found in the liver, and lower levels found in kidney, intestine, spleen, and adrenals (see Willy, et al., *Genes Dev.* 9(9):1033-45 (1995)). LXR$\beta$ is rather ubiquitous, being found in nearly all tissues examined. Recent studies on the LXRs indicate that they are activated by certain naturally occurring, oxidized derivatives of cholesterol, including 22(R)-hydroxycholesterol, 24(S)-hydroxycholesterol and 24,25(S)-epoxycholesterol (see Lehmann, et al., *J. Biol. Chem.* 272(6):3137-3140 (1997)). The expression pattern of LXRs and their oxysterol ligands provided the first hint that these receptors may play a role in cholesterol metabolism (see Janowski, et al., *Nature* 383: 728-731 (1996)).

As noted above, cholesterol metabolism in mammals occurs via conversion into steroid hormones or bile acids. The role of LXRs in cholesterol homeostasis was first postulated to involve the pathway of bile acid synthesis, in which cholesterol 7$\alpha$-hydroxylase (CYP7A) operates in a rate-limiting manner. Support for this proposal was provided when additional experiments found that the CYP7A promoter contained a functional LXR response element that could be activated by RXR/LXR heterodimers in an oxysterol- and retinoid-dependent manner. Confirmation of LXR function as a transcriptional control point in cholesterol metabolism was made using knockout mice, particularly those lacking the oxysterol receptor LXR$\alpha$ (see Peet, et al., *Cell* 93:693-704 (1998)).

Mice lacking the receptor LXR$\alpha$ (e.g., knockout or (−/−) mice) lost their ability to respond normally to increases in dietary cholesterol and were unable to tolerate any cholesterol in excess of that synthesized de novo. LXR$\alpha$ (−/−) mice did not induce transcription of the gene encoding CYP7A when fed diets containing additional cholesterol. This resulted in an accumulation of large amounts of cholesterol and impaired hepatic function in the livers of LXR$\alpha$ (−/−) mice. These results further established the role of LXR$\alpha$ as the essential regulatory component of cholesterol homeostasis. LXR$\alpha$ is also believed to be involved in fatty acid synthesis. Accordingly, regulation of LXR$\alpha$ (e.g., use of LXR$\alpha$ agonist or antagonists) could provide treatment for a variety of lipid disorders including obesity and diabetes.

In view of the importance of LXRs, and particularly LXR$\alpha$s to the delicate balance of cholesterol metabolism and fatty acid biosynthesis, we describe modulators of LXRs which are useful as therapeutic agents or diagnostic agents for the treatment of disorders associated with bile acid and cholesterol metabolism, including cholesterol gallstones, atherosclerosis, lipid storage diseases, obesity, and diabetes. The agents described herein are also useful for disease states associated with serum hypercholesterolemia, such as coronary heart disease.

BRIEF SUMMARY OF THE INVENTION

In one aspect, the present invention provides compounds having the formula:

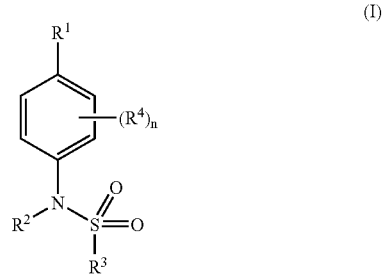

(I)

wherein $R^1$ is selected from:

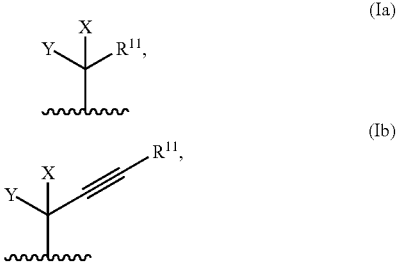

(Ia)

(Ib)

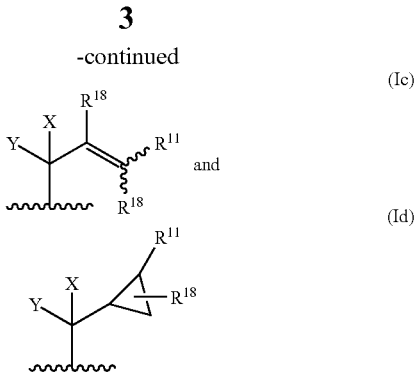

wherein $R^{11}$ is selected from halogen, nitro, cyano, $R^{12}$, $OR^{12}$, $SR^{12}$, $NHR^{12}$, $N(R^{12})_2$, $(C_4\text{-}C_8)$cycloalkyl, $(C_5\text{-}C_8)$cycloalkenyl, $COR^{12}$, $CO_2R^{12}$, $CONHR^{12}$, $CON(R^{12})_2$, aryl, aryl$(C_1\text{-}C_4)$alkyl, heteroaryl and heteroaryl$(C_1\text{-}C_4)$alkyl; wherein each $R^{12}$ is $(C_1\text{-}C_8)$alkyl, $(C_3\text{-}C_8)$alkenyl, $(C_3\text{-}C_8)$alkynyl, $(C_2\text{-}C_8)$heteroalkyl, halo$(C_1\text{-}C_8)$alkyl or two $R^{12}$ groups attached to the same nitrogen atom are combined to form a five- to eight-membered ring and any alkyl portions of $R^{11}$ are optionally substituted with from one to three substituents independently selected from halogen, $OR^{13}$, $NHSO_2R^{14}$ and $NHC(O)R^{13}$, and any aryl or heteroaryl portions of $R^{11}$ are optionally substituted with from one to five substituents independently selected from halogen, cyano, nitro, $R^{14}$, $OR^{13}$, $SR^{13}$, $N(R^{13})_2$, $NHSO_2R^{14}$, $NHC(O)R^{13}$, phenyl, phenyl$(C_1\text{-}C_8)$alkyl, and phenyl$(C_2\text{-}C_8)$heteroalkyl; wherein each $R^{13}$ is independently selected from H, $(C_1\text{-}C_8)$alkyl, $(C_3\text{-}C_8)$alkenyl, $(C_3\text{-}C_8)$alkynyl, $(C_2\text{-}C_8)$heteroalkyl and halo$(C_1\text{-}C_8)$alkyl and each $R^{14}$ is independently selected from $(C_1\text{-}C_8)$alkyl, $(C_3\text{-}C_8)$alkenyl, $(C_3\text{-}C_8)$alkynyl, $(C_2\text{-}C_8)$heteroalkyl and halo$(C_1\text{-}C_8)$alkyl. Optionally, $R^{11}$ is combined with either X or Y to form a five- to six-membered monocyclic or fused bicyclic ring containing from 0 to 3 heteroatoms selected from N, O and S.

Each $R^{18}$ is independently selected from H, $(C_1\text{-}C_8)$alkyl, $(C_2\text{-}C_8)$heteroalkyl, halo$(C_1\text{-}C_8)$alkyl, aryl and heteroaryl.

In each of the $R^1$ groups above, the component X represents H, $NH_2$, $NHR^{15}$, $NHSO_2R^{15}$, OH or $OR^{15}$, wherein $R^{15}$ is $(C_1\text{-}C_8)$alkyl, $(C_3\text{-}C_8)$alkenyl, $(C_3\text{-}C_8)$alkynyl, $(C_2\text{-}C_8)$heteroalkyl or halo$(C_1\text{-}C_8)$alkyl; and the component Y is fluoro$(C_1\text{-}C_4)$alkyl.

Returning to formula I, $R^2$ is selected from H, $(C_1\text{-}C_8)$alkyl, $(C_2\text{-}C_8)$heteroalkyl, $(C_3\text{-}C_8)$alkenyl, $(C_3\text{-}C_8)$alkynyl, $(C_3\text{-}C_8)$cycloalkyl and $(C_4\text{-}C_8)$cycloalkyl-alkyl, wherein any alkyl portions of $R^2$ are optionally substituted with from one to three substituents independently selected from halogen, nitro, cyano, hydroxy, oxo and amino; and $R^3$ is selected from aryl and heteroaryl, the aryl or heteroaryl group being optionally substituted with from one to five substituents independently selected from halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1\text{-}C_8)$alkyl, and phenyl$(C_2\text{-}C_8)$heteroalkyl; wherein each $R^{16}$ is independently selected from $(C_1\text{-}C_8)$alkyl, $(C_3\text{-}C_8)$alkenyl, $(C_3\text{-}C_8)$alkynyl, $(C_2\text{-}C_8)$heteroalkyl and halo$(C_1\text{-}C_8)$alkyl, or two $R^{16}$ groups attached to the same nitrogen atom are combined to form a five- to eight-membered ring. Optionally, $R^2$ and $R^4$ are combined to form a five- to six-membered fused ring containing from 1 to 3 heteroatoms selected from N, O and S.

The subscript n is an integer of from 0 to 3, indicating the presence or absence of substituents on the phenyl ring core of formula I. Each of the $R^4$ substituents is independently selected from halogen, cyano, nitro, $R^{17}$, $OR^{17}$, $SR^{17}$, $COR^{17}$, $CO_2R^{17}$, $N(R^{17})_2$ and $CON(R^{17})_2$, wherein each $R^{17}$ is independently selected from H, $(C_1\text{-}C_8)$alkyl, $(C_3\text{-}C_8)$alkenyl, $(C_3\text{-}C_8)$alkynyl, $(C_2\text{-}C_8)$heteroalkyl or halo$(C_1\text{-}C_8)$alkyl, or two $R^{17}$ groups attached to the same nitrogen atom are combined to form a five- to eight-membered ring.

In addition to the compounds provided in formula I, pharmaceutically acceptable salts thereof are also provided.

In yet another aspect, the present invention provides methods for modulating LXR in a cell by administering to or contacting the cell with a composition containing a compound of Formula I above.

In still another aspect, the present invention provides methods for treating LXR-responsive diseases by administering to a subject in need of such treatment a composition containing a compound of Formula I. These methods are particularly useful for the treatment of pathology such as obesity, diabetes, hypercholesterolemia, atherosclerosis, and hyperlipoproteinemia. In certain embodiments, the compound can be administered to the subject in combination with an additional anti-hypercholesterolemic agent, for example, bile acid sequestrants, nicotinic acid, fibric acid derivatives or HMG CoA reductase inhibitors.

The present compounds can exert their effects either systemically (the compounds permeate the relevant tissues, such as liver, upon entrance into the bloodstream) or locally (for example, by modulating LXR function of intestinal epithelial cells following oral administration, without necessitating the compounds' entrance into the bloodstream). In some disease states, some preferred compounds will be those with good systemic distribution, while, in other instances, preferred compounds will be those that can work locally on the intestinal track or on the skin without penetrating the bloodstream.

Certain compounds of the present invention are antiproliferative and can be used in compositions for treating diseases associated with abnormal cell proliferation (e.g., cancer). Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

BRIEF DESCRIPTION OF THE DRAWINGS

Not applicable.

DETAILED DESCRIPTION OF THE INVENTION

Definitions

As used herein, the term "heteroatom" is meant to include oxygen (O), nitrogen (N), sulfur (S) and silicon (Si).

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_1\text{-}C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., $C_3$-$C_8$ means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo($C_1$-$C_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo($C_1$-$C_4$)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term "heteroaryl" refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R'", —NR'—SO$_2$NR"R'", —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C$_1$-C$_4$)alkoxy and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl and (unsubstituted aryl)oxy-(C$_1$-C$_4$)alkyl. When the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as derined herein for "cycloalkyl". Typically, an aryl or heteroaryl group will have from zero to three substituents, with those groups having two or fewer substituents being preferred in the present invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C$_1$-C$_4$)alkoxy and perfluoro(C$_1$-C$_4$)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C$_1$-C$_4$)alkoxy and perfluoro(C$_1$-C$_4$)alkyl.

It is to be understood that the substituent —CO$_2$H, as used herein, includes bioisosteric replacements therefor, such as:

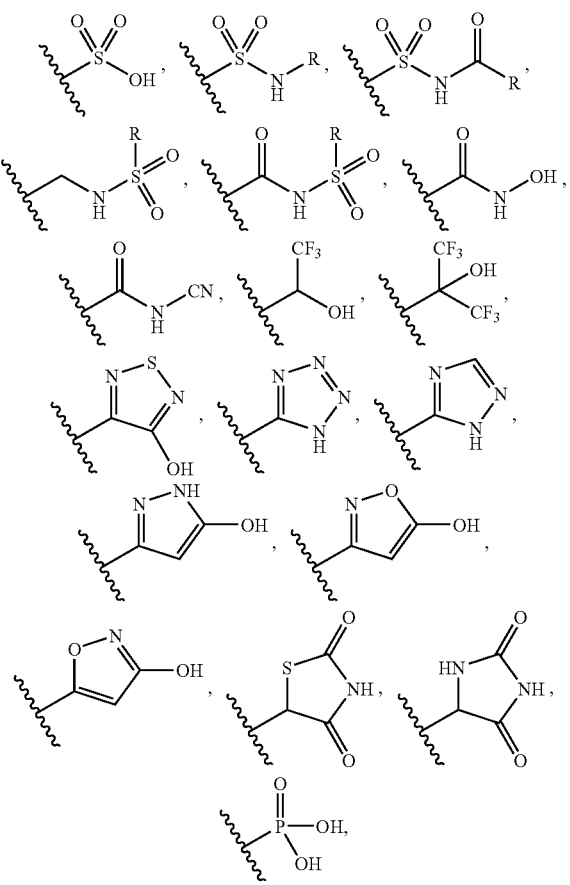

and the like. See, e.g., *The Practice of Medicinal Chemistry*; Wermuth, C. G., Ed.; Academic Press: New York, 1996; p. 203.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)$_s$—X—(CH₂)$_t$—, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted (C₁-C₆)alkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The terms "modulate", "modulation" and the like refer to the ability of a compound to increase or decrease the function and/or expression of LXR, where LXR function may include transcription regulatory activity and/or protein-binding. Modulation may occur in vitro or in vivo. Modulation, as described herein, includes antagonism, agonism, partial antagonism and/or partial agonism of a function or characteristic associated with LXR, either directly or indirectly, and/or the upregulation or downregulation of LXR expression, either directly or indirectly. Agonists are compounds that, e.g., bind to, stimulate, increase, open, activate, facilitate, enhance activation, activate, sensitize or upregulate signal transduction. Antagonists are compounds that, e.g., bind to, partially or totally block stimulation, decrease, prevent, inhibit, delay activation, inactivate, desensitize, or downregulate signal transduction. A modulator preferably inhibits LXR function and/or downregulates LXR expression. More preferably, a modulator inhibits or activates LXR function and/or downregulates or upregulates LXR expression. Most preferably, a modulator activates LXR function and/or upregulates LXR expression. The ability of a compound to modulate LXR function can be demonstrated in a binding assay or a cell-based assay, e.g., a transient transfection assay.

As used herein, "diabetes" refers to type I diabetes mellitus (juvenile onset diabetes, insulin dependent-diabetes mellitus or IDDM) or type II diabetes mellitus (non-insulin-dependent diabetes mellitus or NIDDM), preferably, NIDDM.

As used herein, the term "LXR-mediated condition or disorder" refers to a condition or disorder characterized by inappropriate, e.g., less than or greater than normal, LXR activity. Inappropriate LXR functional activity might arise as the result of LXR expression in cells which normally do not express LXR, decreased LXR expression (leading to, e.g., lipid and metabolic disorders and diseases) or increased LXR expression. An LXR-mediated condition or disease may be completely or partially mediated by inappropriate LXR functional activity. However, an LXR-mediated condition or disease is one in which modulation of LXR results in some effect on the underlying condition or disorder (e.g., an LXR agonist results in some improvement in patient well-being in at least some patients).

As used herein, the term "LXR-responsive condition" or "LXR-responsive disorder" refers to a condition or disorder that responds favorably to modulation of LXR activity. Favorable responses to LXR modulation include alleviation or abrogation of the disease and/or its attendant symptoms, inhibition of the disease, i.e., arrest or reduction of the development of the disease, or its clinical symptoms, and regression of the disease or its clinical symptoms. An LXR-responsive condition or disease may be completely or partially responsive to LXR modulation. An LXR-responsive condition or disorder may be associated with inappropriate, e.g., less than or greater than normal, LXR activity. Inappropriate LXR functional activity might arise as the result of LXR expression in cells which normally do not express LXR, decreased LXR expression (leading to, e.g., lipid and metabolic disorders and diseases) or increased LXR expression. An LXR-responsive condition or disease may include an LXR-mediated condition or disease.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

General

The present invention provides compositions, compounds and methods for modulating LXR function in a cell. The compositions which are useful for this modulation will typically be those which contain an effective amount of an LXR-modulating compound. In general, an effective amount of an LXR-modulating compound is a concentration of the compound that will produce at 50 percent increase/decrease in LXR activity in a cell-based reporter gene assay, or a biochemical peptide-sensor assay such as the assays described in co-pending applications Ser. No. 08/975,614 (filed Nov. 21, 1997) and Ser. No. 09/163,713 (filed Sep. 30, 1998).

EMBODIMENTS OF THE INVENTION

Compounds

In one aspect, the present invention provides compounds having the formula:

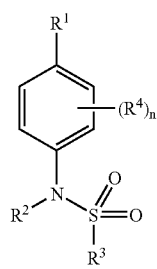

(I)

wherein $R^1$ is selected from:

(Ia)

(Ib)

(Ic)

and (Id)

wherein $R^{11}$ is selected from halogen, nitro, cyano, $R^{12}$, $OR^{12}$, $SR^{12}$, $NHR^{12}$, $N(R^{12})_2$, $(C_4-C_8)$cycloalkyl, $(C_5-C_8)$cycloalkenyl, $COR^{12}$, $CO_2R^{12}$, $CONHR^{12}$, $CON(R^{12})_2$, aryl, aryl$(C_1-C_4)$alkyl, heteroaryl and heteroaryl$(C_1-C_4)$alkyl; wherein each $R^{12}$ is $(C_1-C_8)$alkyl, $(C_3-C_8)$alkenyl, $(C_3-C_8)$alkynyl, $(C_2-C_8)$heteroalkyl, halo$(C_1-C_8)$alkyl or two $R^{12}$ groups attached to the same nitrogen atom are combined to form a five- to eight-membered ring and any alkyl portions of $R^{11}$ are optionally substituted with from one to three substituents independently selected from halogen, $OR^{13}$, $NHSO_2R^{14}$ and $NHC(O)R^{13}$, and any aryl or heteroaryl portions of $R^{11}$ are optionally substituted with from one to five substituents independently selected from halogen, cyano, nitro, $R_{14}$, $OR^{13}$, $SR^{13}$, $N(R^{13})_2$, $NHSO_2R^{14}$, $NHC(O)R^{13}$, phenyl, phenyl$(C_1-C_8)$alkyl, and phenyl$(C_2-C_8)$heteroalkyl; wherein each $R^{13}$ is independently selected from H, $(C_1-C_8)$alkyl, $(C_3-C_8)$alkenyl, $(C_3-C_8)$alkynyl, $(C_2-C_8)$heteroalkyl and halo$(C_1-C_8)$alkyl and each $R^{14}$ is independently selected from $(C_1-C_8)$alkyl, $(C_3-C_8)$alkenyl, $(C_3-C_8)$alkynyl, $(C_2-C_8)$heteroalkyl and halo$(C_1-C_8)$alkyl. Optionally, $R^{11}$ is combined with either X or Y to form a five- to six-membered monocyclic or fused bicyclic ring containing from 0 to 3 heteroatoms selected from N, O and S. Additionally, when $R^1$ is a group of formula Ia, $R^{11}$ is other than $(C_1-C_3)$alkyl and halo$(C_1-C_3)$alkyl.

Each $R^{18}$ is independently selected from the group consisting of H, $(C_1-C_8)$alkyl, $(C_2-C_8)$heteroalkyl, halo$(C_1-C_8)$alkyl, aryl and heteroaryl.

In each of the $R^1$ groups above, the component X represents H, $NH_2$, $NHR^{15}$, $NHSO_2R^{15}$, OH or $OR^{15}$, wherein $R^{15}$ is $(C_1-C_8)$alkyl, $(C_3-C_8)$alkenyl, $(C_3-C_8)$alkynyl, $(C_2-C_8)$heteroalkyl or halo$(C_1-C_8)$alkyl; and Y is fluoro$(C_1-C_4)$alkyl. In particularly preferred embodiments, Y is $CF_3$.

Returning to formula I, $R^2$ is selected from H, $(C_1-C_8)$alkyl, $(C_2-C_8)$heteroalkyl, $(C_3-C_8)$alkenyl, $(C_3-C_8)$alkynyl, $(C_3-C_8)$cycloalkyl and $(C_4-C_8)$cycloalkyl-alkyl, wherein any alkyl portions of $R^2$ are optionally substituted with from one to three substituents independently selected from halogen, nitro, cyano, hydroxy, oxo and amino; and $R^3$ is selected from aryl and heteroaryl, the aryl or heteroaryl group being optionally substituted with from one to five substituents independently selected from halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{16}$ groups attached to the same nitrogen atom are combined to form a five- to eight-membered ring. Optionally, $R^2$ and $R^4$ are combined to form a five- to six-membered fused ring containing from 1 to 3 heteroatoms selected from N, O and S.

The subscript n is an integer of from 0 to 3, indicating the presence or absence of substituents on the phenyl ring core of formula I. Each of the $R^4$ substituents is independently selected from halogen, cyano, nitro, $R^{17}$, $OR^{17}$, $SR^{17}$, $COR^{17}$, $CO_2R^{17}$, $N(R^{17})_2$ and $CON(R^{17})_2$, wherein each $R^{17}$ is independently selected from H, ($C_1$-$C_8$)alkyl, ($C_3$-$C_8$)alkenyl, ($C_3$-$C_8$)alkynyl, ($C_2$-$C_8$)heteroalkyl or halo($C_1$-$C_8$)alkyl, or two $R^{17}$ groups attached to the same nitrogen atom are combined to form a five- to eight-membered ring.

In addition to the compounds provided in formula I, pharmaceutically acceptable salts thereof are also provided.

In one group of preferred embodiments, $R^1$ is selected from

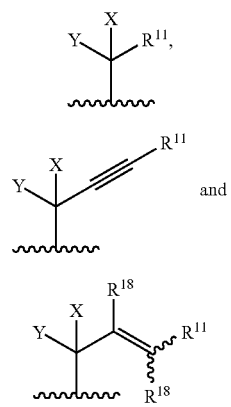

and X is OH.

In another group of preferred embodiments, $R^1$ is selected from

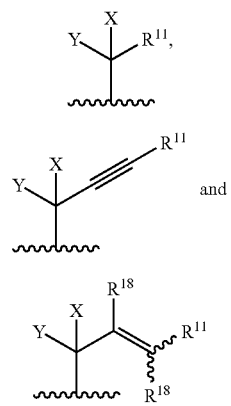

and X is H.

Within each of these groups of preferred embodiments are several further preferred groups. Accordingly, in the discussion below, preferred embodiments are provided in which X is H or X is OH.

In one of these groups, $R^1$ is

wherein $R^{11}$ is selected from phenyl, pyridyl, pyridazinyl, imidazolyl, thiazolyl, oxazolyl, pyrrolyl, tetrazolyl, indolyl, benzimidazolyl, benzothienyl and benzothiazolyl, each of these $R^{11}$ groups being optionally substituted with from one to five substituents independently selected from halogen, cyano, nitro, ($C_1$-$C_8$)alkyl, ($C_3$-$C_8$)alkenyl, ($C_3$-$C_8$)alkynyl, ($C_2$-$C_8$)heteroalkyl, ($C_1$-$C_8$)haloalkyl, phenyl($C_1$-$C_6$)alkyl and phenyl($C_2$-$C_6$)heteroalkyl. In particularly preferred embodiments, Y is $CF_3$.

In still further preferred embodiments, $R^1$ is a group of formula Ia in which $R^{11}$ is phenyl, optionally substituted with from one to two substituents independently selected from the group consisting of halogen, cyano, nitro, ($C_1$-$C_8$)alkyl, ($C_3$-$C_8$)alkenyl, ($C_3$-$C_8$)alkynyl, ($C_2$-$C_8$)heteroalkyl, ($C_1$-$C_8$)haloalkyl, phenyl($C_1$-$C_6$)alkyl and phenyl($C_2$-$C_6$)heteroalkyl. The remaining groups $R^2$, $R^3$ and $R^4$ also have certain preferred members. In particular, $R^2$ is preferably selected from H, ($C_1$-$C_8$)alkyl, ($C_3$-$C_8$)cycloalkyl and ($C_4$-$C_8$)cycloalkyl-alkyl, wherein any alkyl portions of $R^2$ are optionally substituted with from one to three substituents independently selected from halogen, nitro, cyano, hydroxy, oxo and amino. $R^3$ is preferably selected from phenyl, pyridyl, thienyl and thiazolyl, optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{16}$ groups attached to the same nitrogen atom are combined to form a five- to eight-membered ring. The subscript n is preferably 0, 1, or 2 and each $R^4$ is preferably selected from halogen, ($C_1$-$C_8$)alkyl and halo($C_1$-$C_8$)alkyl.

In another group of still further preferred embodiments, $R^1$ is a group of formula Ia in which $R^{11}$ is pyrrolyl, optionally substituted with from one to two substituents independently selected from halogen, nitro, cyano, ($C_1$-$C_8$)alkyl, ($C_3$-$C_8$)alkenyl, ($C_3$-$C_8$)alkynyl, ($C_2$-$C_8$)heteroalkyl, ($C_1$-$C_8$)haloalkyl, phenyl($C_1$-$C_6$)alkyl and phenyl($C_2$-$C_6$)heteroalkyl. Preferred members of the remaining groups $R^2$, $R^3$ and $R^4$ are the same as have been described above for the embodiments in which $R^{11}$ is phenyl.

Another group of preferred embodiments are those compounds of formula I in which $R^1$ is

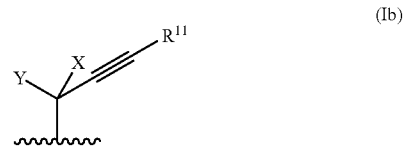

wherein $R^{11}$ is selected from phenyl, pyridyl, pyridazinyl, imidazolyl, thiazolyl, oxazolyl, pyrrolyl, tetrazolyl, indolyl, benzimidazolyl, benzothienyl and benzothiazolyl, each of these $R^{11}$ groups being optionally substituted with from one to five substituents independently selected from halogen, cyano, nitro, $(C_1\text{-}C_8)$alkyl, $(C_3\text{-}C_8)$alkenyl, $(C_3\text{-}C_8)$alkynyl, $(C_2\text{-}C_8)$heteroalkyl, $(C_1\text{-}C_8)$haloalkyl, phenyl$(C_1\text{-}C_6)$alkyl and phenyl$(C_2\text{-}C_6)$heteroalkyl. In particularly preferred embodiments, Y is $CF_3$.

In still further preferred embodiments, $R^1$ is a group of formula Ib in which $R^{11}$ is phenyl, optionally substituted with from one to two substituents independently selected from the group consisting of halogen, cyano, nitro, $(C_1\text{-}C_8)$ alkyl, $(C_3\text{-}C_8)$alkenyl, $(C_3\text{-}C_8)$alkynyl, $(C_2\text{-}C_8)$heteroalkyl, $(C_1\text{-}C_8)$haloalkyl, phenyl$(C_1\text{-}C_6)$alkyl and phenyl$(C_2\text{-}C_6)$heteroalkyl. The remaining groups $R^2$, $R^3$ and $R^4$ also have certain preferred members. In particular, $R^2$ is preferably selected from H, $(C_1\text{-}C_8)$alkyl, $(C_3\text{-}C_8)$cycloalkyl and $(C_4\text{-}C_8)$cycloalkyl-alkyl, wherein any alkyl portions of $R^2$ are optionally substituted with from one to three substituents independently selected from halogen, nitro, cyano, hydroxy, oxo and amino. $R^3$ is preferably selected from phenyl, pyridyl, thienyl and thiazolyl, optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1\text{-}C_8)$ alkyl, and phenyl$(C_2\text{-}C_8)$heteroalkyl; wherein each $R^{16}$ is independently selected from $(C_1\text{-}C_8)$alkyl, $(C_3\text{-}C_8)$alkenyl, $(C_3\text{-}C_8)$alkynyl, $(C_2\text{-}C_8)$heteroalkyl and halo$(C_1\text{-}C_8)$alkyl, or two $R^{16}$ groups attached to the same nitrogen atom are combined to form a five- to eight-membered ring. The subscript n is preferably 0, 1, or 2 and each $R^4$ is preferably selected from halogen, $(C_1\text{-}C_8)$alkyl and halo$(C_1\text{-}C_8)$alkyl.

In another group of still further preferred embodiments, $R^1$ is a group of formula Ib in which $R^{11}$ is pyridyl, optionally substituted with from one to two substituents independently selected from halogen, cyano, nitro, $(C_1\text{-}C_8)$alkyl, $(C_3\text{-}C_8)$ alkenyl, $(C_3\text{-}C_8)$alkynyl, $(C_2\text{-}C_8)$heteroalkyl, $(C_1\text{-}C_8)$haloalkyl, phenyl$(C_1\text{-}C_6)$alkyl and phenyl$(C_2\text{-}C_6)$heteroalkyl. Preferred members of the remaining groups $R^2$, $R^3$ and $R^4$ are the same as have been described above for the embodiments in which $R^{11}$ is phenyl.

In yet another group of still further preferred embodiments, $R^1$ is a group of formula Ib in which $R^{11}$ is pyridazinyl or pyrrolyl, optionally substituted with from one to two substituents independently selected from halogen, cyano, nitro, $(C_1\text{-}C_8)$alkyl, $(C_3\text{-}C_8)$alkenyl, $(C_3\text{-}C_8)$alkynyl, $(C_2\text{-}C_8)$heteroalkyl, $(C_1\text{-}C_8)$haloalkyl, phenyl$(C_1\text{-}C_6)$alkyl and phenyl$(C_2\text{-}C_6)$heteroalkyl. Preferred members of the remaining groups $R^2$, $R^3$ and $R^4$ are the same as have been described above for the embodiments in which $R^{11}$ is phenyl.

Still another group of preferred embodiments are those compounds of formula I in which $R^1$ is

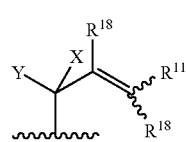

(Ic)

wherein $R^{11}$ is selected from phenyl, pyrrolyl, pyridyl and pyridazinyl, each of these $R^{11}$ groups being optionally substituted with from one to five substituents independently selected from halogen, cyano, nitro, $(C_1\text{-}C_8)$alkyl, $(C_3\text{-}C_8)$ alkenyl, $(C_3\text{-}C_8)$alkynyl, $(C_2\text{-}C_8)$heteroalkyl, $(C_1\text{-}C_8)$haloalkyl, phenyl$(C_1\text{-}C_6)$alkyl and phenyl$(C_2\text{-}C_6)$heteroalkyl. In particularly preferred embodiments, Y is $CF_3$.

In still further preferred embodiments, $R^1$ is a group of formula Ic in which $R^{11}$ is phenyl, optionally substituted with from one to two substituents independently selected from the group consisting of halogen, cyano, nitro, $(C_1\text{-}C_8)$ alkyl, $(C_3\text{-}C_8)$alkenyl, $(C_3\text{-}C_8)$alkynyl, $(C_2\text{-}C_8)$heteroalkyl, $(C_1\text{-}C_8)$haloalkyl, phenyl$(C_1\text{-}C_6)$alkyl and phenyl$(C_2\text{-}C_6)$heteroalkyl. The remaining groups $R^2$, $R^3$ and $R^4$ also have certain preferred members. In particular, $R^2$ is preferably selected from H, $(C_1\text{-}C_8)$alkyl, $(C_3\text{-}C_8)$cycloalkyl and $(C_4\text{-}C_8)$cycloalkyl-alkyl, wherein any alkyl portions of $R^2$ are optionally substituted with from one to three substituents independently selected from halogen, nitro, cyano, hydroxy, oxo and amino. $R^3$ is preferably selected from phenyl, pyridyl, thienyl and thiazolyl, optionally substituted with from one to five substituents independently selected from the group consisting of halogen, cyano, nitro, $R^{16}$, $OR^{16}$, $SR^{16}$, $COR^{16}$, $CO_2R^{16}$, $NHR^6$, $N(R^{16})_2$, $CONHR^{16}$, $CON(R^{16})_2$, $NHSO_2R^{16}$, $NHC(O)R^{16}$, phenyl, phenyl$(C_1\text{-}C_8)$ alkyl, and phenyl$(C_2\text{-}C_8)$heteroalkyl; wherein each $R^{16}$ is independently selected from $(C_1\text{-}C_8)$alkyl, $(C_3\text{-}C_8)$alkenyl, $(C_3\text{-}C_8)$alkynyl, $(C_2\text{-}C_8)$heteroalkyl and halo$(C_1\text{-}C_8)$alkyl, or two $R^{16}$ groups attached to the same nitrogen atom are combined to form a five- to eight-membered ring. The subscript n is preferably 0, 1, or 2 and each $R^4$ is preferably selected from halogen, $(C_1\text{-}C_8)$alkyl and halo$(C_1\text{-}C_8)$alkyl.

The most preferred compounds of the present invention are those provided in the Examples below.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3$H (tritium) and $^{14}$C (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

In another aspect of the invention, pharmaceutical compositions are provided in which a compound of formula I is combined with a pharmaceutically acceptable carrier or diluent. Particular compositions and methods for their use are provided in more detail below.

In yet another aspect, the present invention provides a method for modulating the action of an LXR receptor, preferably LXRα, in a cell. According to this method, the cell is contacted with a sufficient concentration of a composition containing a compound of formula I for either an agonistic or antagonistic effect to be detected. In preferred embodiments, the composition contains an amount of the compound which has been determined to provide a desired therapeutic or prophylactic effect for a given LXR-mediated condition.

In still another aspect, the present invention provides methods for the treatment of pathology such as hypercholesterolemia, atherosclerosis, and hyperlipoproteinemia using pharmaceutical compositions containing compounds of the foregoing description of the general Formula 1. Briefly, this aspect of the invention involves administering to a patient an effective formulation of one or more of the subject compositions. In other embodiments, the compound of Formula I can be administered in combination with other anti-hypercholesterolemic agents (e.g., a bile acid sequestrant, nicotinic acid, fibric acid derivatives or HMG CoA reductase inhibitors), or in combination with other agents that affect cholesterol or lipid metabolism.

Preparation of the Compounds

Several methods for preparing the compounds of the present invention are illustrated in the following schemes and examples. Starting materials are made by known procedures or as illustrated. One of skill in the art will understand that similar methods can be used for the synthesis of the compounds.

As shown in Scheme 1, compounds of the present invention can be prepared beginning with commercially available 1',1',1',4-tetrafluoroacetophenone (1-1). Treatment of 1-1 with an N-substituted arylsulfonamide (1-2) in the presence of a base such as potassium carbonate, cesium carbonate, or sodium hydride in a suitable solvent such as DMF or DMSO provides adduct 1-3. Treatment of 1-3 with organometal species 1-4 provides compounds of formula 1-5.

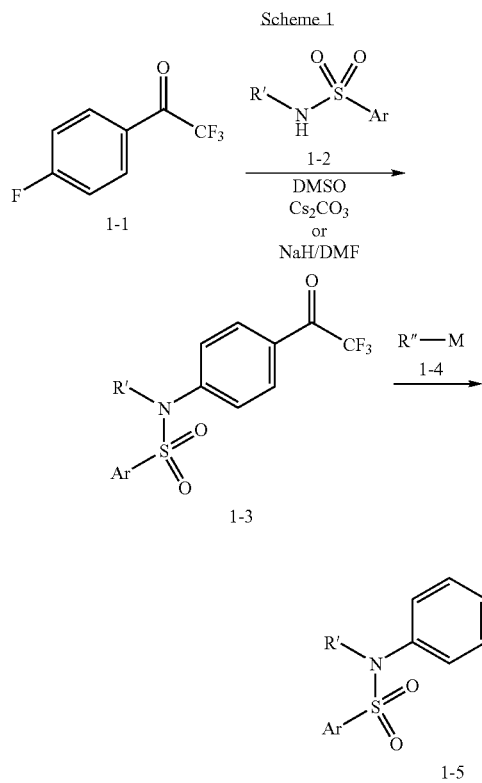

Examples of suitable organometal compounds are shown in Scheme 2. As illustrated in Scheme 2, a heterocycle, for example, 1-alkylimidazole 2-1, can be lithiated with n-butyllithium in THF or diethylether to give derivative 2-2. Also, bromodifluoroacetate or iododifluoroacetate can be converted into zinc species 2-4 by heating in the presence of zinc powder. An arylhalide or heteroarylhalide (2-5) can be converted to organomagnesium species 2-6 by reaction with magnesium in THF or diethylether or reaction with isopropylmagnesium bromide. In addition, an alkyne can be lithiated with, for example, n-butyllithium in THF, or metalated with isopropylmagnesium bromide in THF.

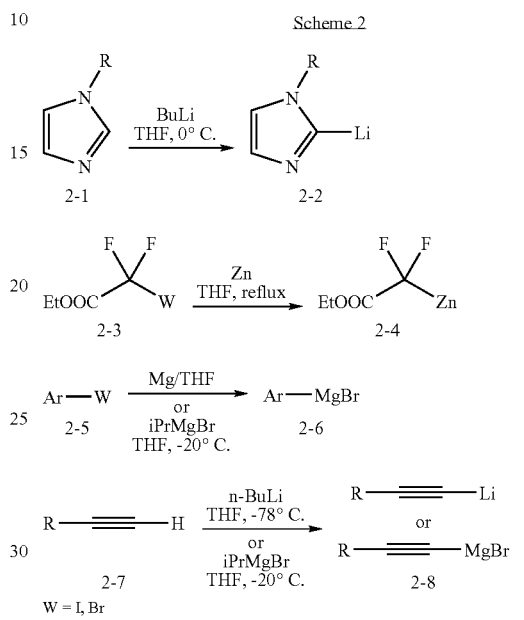

The preparation of intermediate alkynes 2-7 is illustrated in Scheme 3. An alkyl, aryl or heteroaryl halide (3-1) can be coupled to 2-methyl-3-butyn-2-ol according to the procedure described in Bleicher et al. (1995) *Synlett* 1115-1116. Resulting alcohol 3-2, can be converted to alkyne 2-7 using a base such as sodium hydride in a suitable solvent such as toluene, according to the procedure described in Havens et al. (1985) *J. Org. Chem.*, 50:1763-1765.

Alternatively an alkyl, aryl or heteroaryl halide can be coupled to ethynyltrimethylsilane via a Palladium mediated reaction to afford 3-4 (see, e.g., R. C. Larock; *Comprehensive Organic Transformations*, 2$^{nd}$ ed., John Wiley & Sons, New York, pp. 596-599, (1999)). Subsequent treatment of 3-4 with, for example, potassium carbonate in anhydrous methanol gives alkyne 2-7.

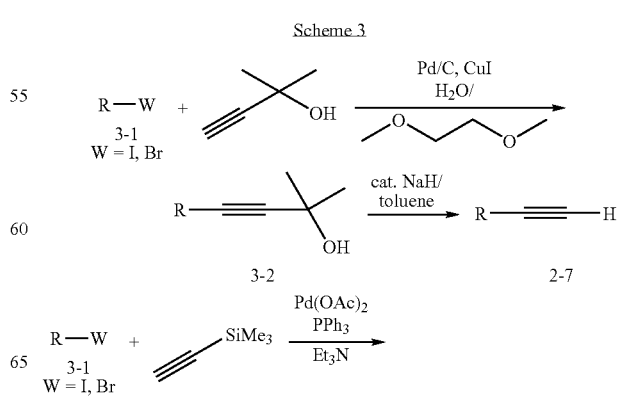

-continued

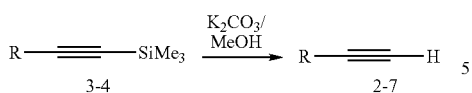

An alternative preparation of the compounds of the present invention is shown in Scheme 4.

Scheme 4

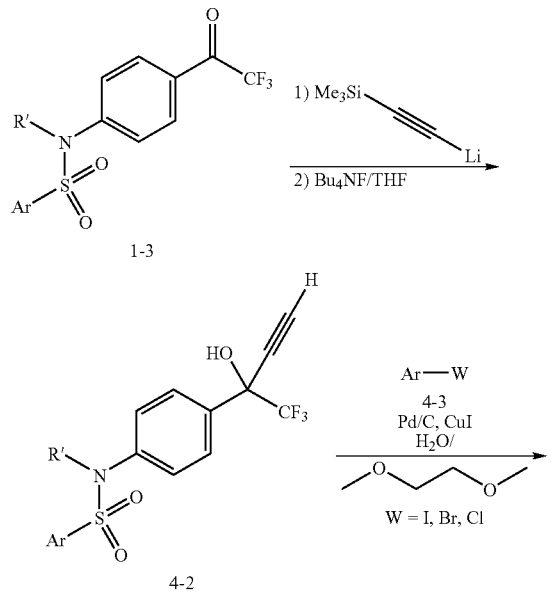

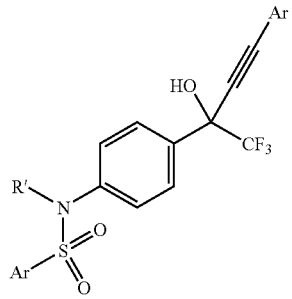

Trimethylsilyl-ethynyl lithium is added to 1-3 and the adduct subsequently treated with tetrabutyl ammonium fluoride in THF to give ethynyl derivative 4-2. This derivative can be reacted with an alkyl, aryl or heteroaryl halide using the procedure described by Bleicher et al. (1995) *Synlett*, 1115-1116 or a similar Palladium mediated coupling reaction (see, e.g., R. C. Larock; Comprehensive Organic Transformations, $2^{nd}$ ed., John Wiley & Sons, New York, pp. 596-599, (1999)) to afford 4-4.

Another alternative synthesis of the compounds of the present invention is shown in Scheme 5. A haloaniline (5-1) can be alkylated, acylated or arylated (general addition of R-group) to form 5-2. 5-2 can be sulfonylated with, for example, an appropriate sulfonyl halide (5-3) to form 5-4. Halo-substituted arylsulfonamide 5-4 can be converted to alcohol 5-7 upon treatment with t-butyllithium followed by ketone 5-5. Alternatively, 5-2 can be converted to 5-6 upon treatment with t-butyllithium followed by ketone 5-5. Alcohol 5-6 can be sulfonylated to form compounds of formula 5-7.

Scheme 5

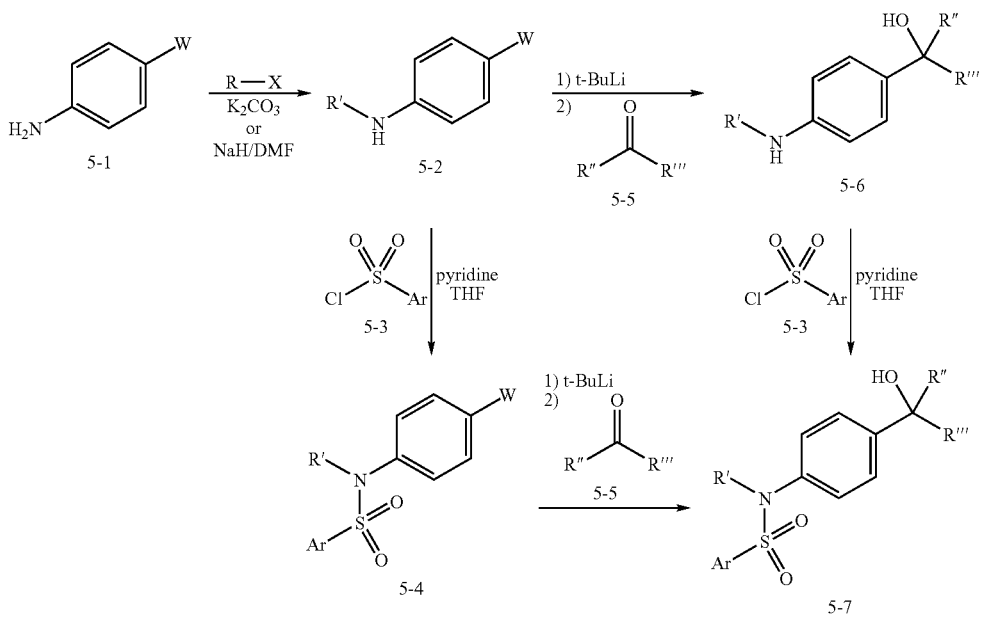

The synthesis of compounds possessing the general formula 6-4 is shown in Scheme 6. Halo-substituted arylsulfonamide 5-4 can be converted into fluoroketone 6-3 upon treatment with t-butyllithium followed by addition of α,α-difluoroester 6-2. Subsequent treatment of 6-3 with $CF_3$-TMS in the presence of tetrabutylammonium fluoride in THF (see, e.g., G. K. S. Prakash in *Synthetic Fluorine Chemistry*; G. A. Olah et al., Eds. John Wiley; New York, 1992; Chapter 10) provides compounds of formula 6-4.

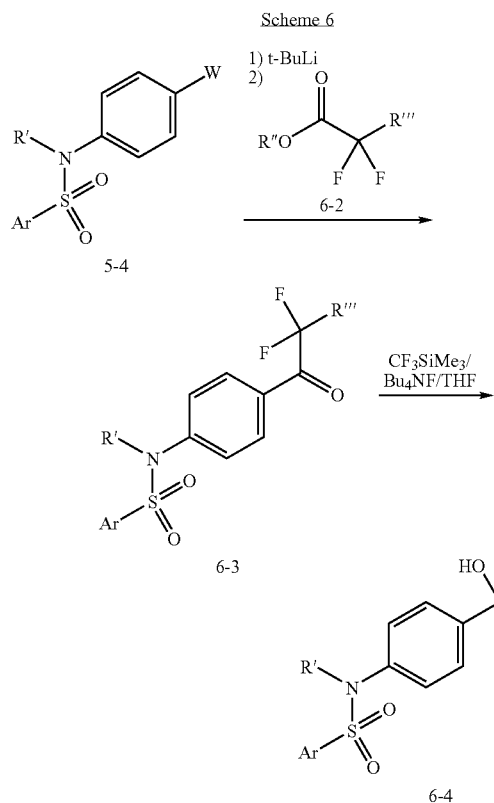

Preparation of intermediate α,α-difluoroester 6-2 can be accomplished by a variety of methods, including the methods illustrated in Scheme 7. Ketoester 7-1 can be fluorinated with diethylaminosulfur trifluoride (DAST), as reviewed in Middleton (1975) *J. Org. Chem.* 40:574. Acetic acid ester 7-3 can be fluorinated by treatment with a strong base, such as potassium hexamethyldisalazide, followed by addition of a suitable fluorinating agent, such as 7-4 (see, e.g., Differding et al. (1991) *Tetrahedron Lett.* 32:1779). Alternatively, an aryl iodide or aryl bromide can be treated with ethyl bromodifluoroacetate (7-5) in the presence of copper metal to provide 7-6 (see, e.g., Eto et al. (2000) *Chem. Pharm. Bull.* 48:982).

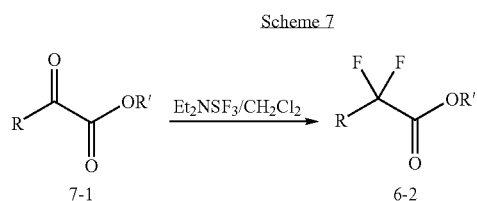

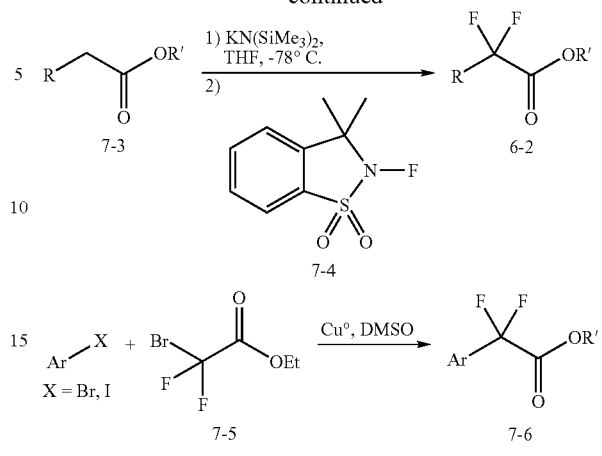

As shown in Scheme 8, alcohols 5-7 can be alkylated in the presence of a base such as sodium hydride in a suitable solvent such as THF or DMF to give ethers 8-2 or deoxygenated to give 8-3 by using, e.g., triethylsilane and $BF_3 \cdot OEt_2$.

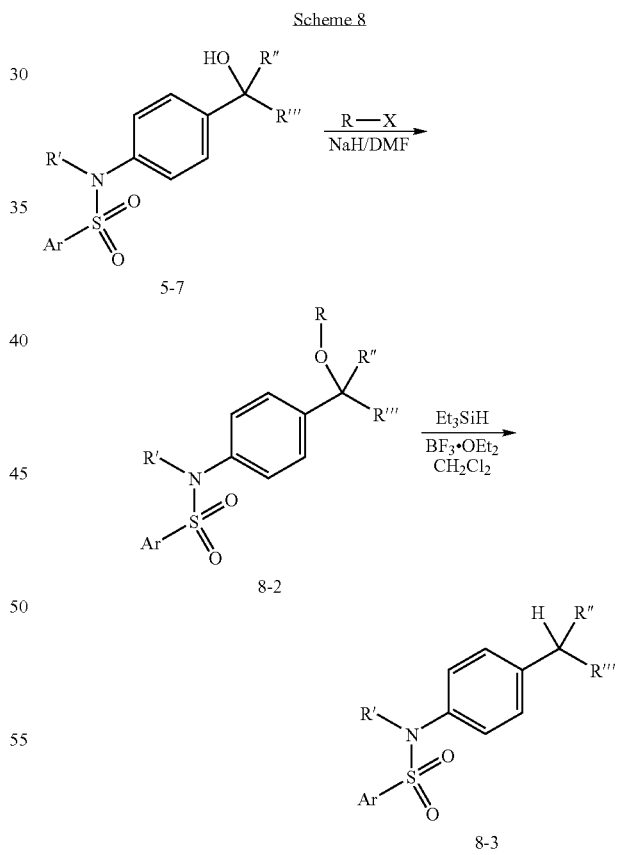

Analysis of Compounds

Representative compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically regulating LXR. Compounds may be evaluated in vitro for their ability to activate LXR receptor function using biochemical assays (see co-pending application Ser. No. 08/975,614 (filed Nov. 21, 1997) and Ser. No. 09/163,713 (filed Sep. 30, 1998)), or in cell-based assays such as that described in Lehmann, et al. (*J. Biol. Chem.* 1997, 272(6), 3137-3140). Alternatively, the compounds and compositions can be evaluated for their ability to increase or decrease gene expression modulated by LXR, using western-blot analysis. Established animal models to evaluate hypocholesterolemic effects of the compounds are also known in the art. For example, compounds disclosed herein can lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med. Chem.* 1995, 38, 277). Still further, LXRα animal models (e.g., LXRα (+/−) and (−/−) mice) can be used for evaluation of the present compounds and compositions (see, for example, Peet, et al. *Cell* 1998, 93, 693-704).

Accordingly, as used herein, the term "LXR-modulating amount" refers to that amount of a compound that is needed to produce a desired effect in any one of the cell-based assays, biochemical assays or animal models described above. Typically, an LXR-modulating amount of a compound will be at least that amount which exhibits an $EC_{50}$ in a reporter-gene cell-based assay (relative to an untreated control).

Formulation and Administration of Compounds and Pharmaceutical Compositions

The invention provides methods of using the subject compounds and compositions to treat disease or provide medicinal prophylaxis, to activate LXR receptor function in a cell, to reduce blood cholesterol concentration in a host, to slow down and/or reduce the abnormal cellular proliferation including the growth of tumors, etc. These methods generally involve contacting the cell or cells with or administering to a host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic therapeutic or prophylactic agents, different from the subject compounds. In many instances, administration in conjunction with the subject compositions enhances the efficacy of such agents. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to use labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated and typically include: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). Starting materials in the synthesis examples below are either available from commercial sources such as Aldrich Chemical Co., Milwaukee, Wis., USA, or via literature procedures. Abbreviations used in the examples below have their accepted meanings in the chemical literature. For example, THF (tetrahydrofuran), $Et_2O$ (diethyl ether), MeOH (methanol), $CH_2Cl_2$ (methylene chloride), LDA (lithium diisopropylamide), MeCN (acetonitrile), and DMAP (4-dimethyaminopyridine).

Example 1

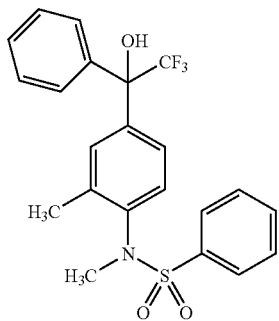

N-Methyl-N-[2-methyl-4-(2,2,2-trifluoro-1-hydroxy-1-phenethyl)]-benzenesulfonamide

Step A. N-Methyl-4-bromo-2-methylaniline

To a solution of 2.03 g (10.91 mmol) of 4-bromo-2-methylaniline in 40 ml of DMF was added 2.07 g (14.98 mmol) of $K_2CO_3$ and 0.63 ml (10.12 mmol) of iodomethane, and the mixture was stirred at room temperature for 14 hours. After this time, the reaction mixture was quenched by the addition of a saturated aqueous solution of ammonium chloride and extracted with EtOAc. The combined organic layers were washed with brine, dried over $MgSO_4$, filtered and the filtrate was concentrated. The residue was purified by chromatography on silica gel (hexanes:EtOAc, 20:1) to give the title compound. $^1$H-NMR (CDCl$_3$) δ 2.18 (s, 3H), 2.90 (s, 3H), 3.60 (brs, 1H), 6.49 (d, J=8.6 Hz, 1H), 7.19 (s, 1H), 7.29 (d, J=8.5 Hz, 1H).

Step B. N-Methyl-N-(4-methoxybenzyl)-4-bromo-2-methylaniline

To a solution of 2.7 g (13.57 mmol) of N-methyl-4-bromo-2-methylaniline in 20 ml of DMF at room temperature was added 608 mg (15.2 mmol) of NaH and the mixture was stirred at room temperature for 0.5 h. After this time, 2.05 ml (15.1 mmol) of 4-methoxybenzyl chloride was added and the reaction mixture was heated to 60° C. for 12 hours. After this time, the reaction mixture was allowed to cool to room temperature and was quenched by the addition of a saturated aqueous solution of ammonium chloride and extracted with EtOAc. The combined organic layers were washed with brine, dried over $MgSO_4$, filtered and the filtrate was concentrated. The residue was purified by chromatography (silica, hexanes:EtOAc, 20:1) to give the title compound. $^1$H-NMR (CDCl$_3$) δ 2.41 (s, 3H), 2.58 (s, 3H), 3.84 (s, 3H), 3.98 (s, 2H), 6.89-6.94 (m, 3H), 7.26-7.36 (m, 4H).

Step C. 2,2,2-Trifluoro-1-(3-methyl-4-methylaminophenyl)-1-phenyl-ethanol

To a solution of 1.03 g (3.23 mmol) of N-(4-bromo-2-methylphenyl)-N-methyl-benzenesulfonamide in 30 ml THF at −78° C. was added dropwise 3.9 ml (6.63 mmol) of a 1.7M solution of tert-BuLi in hexanes and the resultant mixture was stirred at −78° C. for 0.5 h. To this mixture was then added 0.66 ml (4.7 mmol) of 2,2,2-trifluoroacetophenone and the mixture stirred at −78° C. for an additional 0.5 h. The reaction was quenched by the addition of a saturated aqueous solution of ammonium chloride, allowed to warm to room temperature, and extracted with EtOAc. The combined organic layers were washed with brine, dried over $MgSO_4$, filtered and the filtrate was concentrated. 253 mg (0.61 mmol) of this material and 3 ml of TFA was heated to 50° C. for 4 hours. After this time, excess TFA was removed in vacuo, water was added and the mixture was neutralized by the addition of a saturated aqueous solution of NaHCO$_3$. The mixture was extracted with EtOAc and combined organic layers were washed with brine, dried over $MgSO_4$, filtered and the filtrate was concentrated. The residue was purified by chromatography (silica, hexanes:EtOAc, 3:1) to give the title compound. $^1$H-NMR (CDCl$_3$) δ 2.12 (s, 3H), 2.92 (s, 3H), 6.57 (d, J=8.5 Hz, 1H), 7.16 (s, 1H), 7.16 (brs, 1H), 7.37-7.41 (m, 3H), 7.54-7.56 (m, 2H). Mass Spectrum (CI+) m/e=296.1 (M+1).

Step D. N-Methyl-N-[2-methyl-4-(2,2,2-trifluoro-1-hydroxy-1-phenethyl)]-benzenesulfonamide A mixture of 27 mg (0.09 mmol) of 2,2,2-trifluoro-1-(3-methyl-4-methylaminophenyl)-1-phenyl-ethanol and 15 µl (0.12 mmol) of benzenesulfonyl chloride in 0.2 ml of pyridine was heated to 70° C. for 13 hours. After this time the reaction mixture was allowed to cool to room temperature, quenched by the addition of a saturated aqueous solution of ammonium chloride, and extracted with EtOAc. The combined organic layers were washed with brine, dried over $MgSO_4$, filtered and the filtrate was concentrated. The residue was purified by chromatography (silica, hexanes:EtOAc, 4:1) to give the title compound. $^1$H-NMR (CDCl$_3$) δ 2.39 (s, 3H), 3.14 (s, 3H), 6.62 (d, J=8.4 Hz, 1H), 7.13-7.26 (m, 1H), 7.39-7.42 (m, 4H), 7.50-7.56 (m, 4H), 7.62-7.65 (m, 1H), 7.74 (d, J=8.5 Hz, 2H). Mass Spectrum (CI+) m/e=458.0 (M+23).

The compounds of Examples 2-4 were prepared from 2,2,2-trifluoro-1-(3-methyl-4-methylaminophenyl)-1-phenyl-ethanol as described in Example 1, Step D, using an appropriate sulfonylchloride.

Example 2

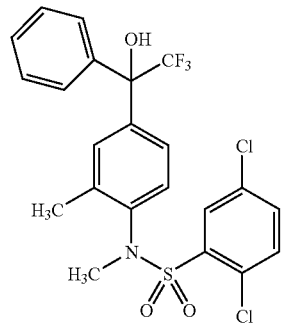

2,5-Dichloro-N-Methyl-N-[2-methyl-4-(2,2,2-trifluoro-1-hydroxy-1-phenethyl)]-benzenesulfonamide $^1$H-NMR (CDCl$_3$) δ 2.33 (s, 3H), 3.39 (s, 3H), 6.84 (d, J=8.4 Hz, 1H), 7.14-7.25 (m, 1H), 7.38-7.40 (m, 4H), 7.45-7.51 (m, 4H), 7.85 (s, 1H). Mass Spectrum (CI+) m/e=526.0 (M+23).

Example 3

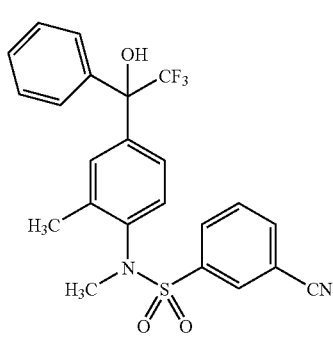

3-Cyano-N-Methyl-N-[2-methyl-4-(2,2,2-trifluoro-1-hydroxy-1-phenethyl)]-benzenesulfonamide $^1$H-NMR (CDCl$_3$) δ 2.37 (s, 3H), 3.18 (s, 3H), 6.58 (d, J=8.4 Hz, 1H), 7.16-7.27(m, 1H), 7.40-7.44 (m, 3H), 7.50-7.52 (m,3H), 7.67-7.71 (m, 1H), 8.02 (s, 1H). Mass Spectrum (CI−) m/e=459.0 (M−1).

Example 4

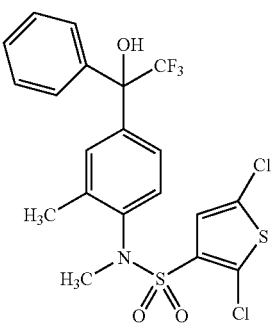

2,5-Dichlorothiophene-3-sulfonic acid-N-methyl-N-[2-methyl-4-(2,2,2-trifluoro-1-hydroxy-1-phenethyl)-phenyl]-amide $^1$H-NMR (CDCl$_3$) δ 2.39 (s, 3H), 3.29 (s, 3H), 6.88 (d, J=8.4 Hz, 1H), 6.96 (s, 1H), 7.28-7.50 (m, 7H). Mass Spectrum (CI+) m/e=532.0 (M+23).

Example 5

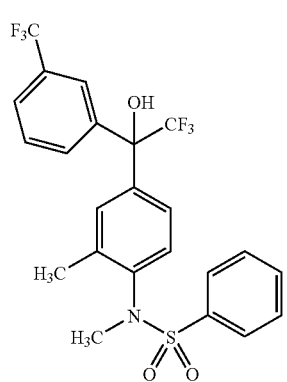

N-Methyl-N-{2-methyl-4-[2,2,2-trifluoro-1-hydroxy-1-(3-trifluoromethyl-phenyl)-ethyl]-phenyl}-benzenesulfonamide Step A. 2,2,2-Trifluoromethyl-1-(3-methyl-4-methylaminophenyl)-1-(3-trifluoromethyl-phenyl)-ethanol To a solution of 1.03 g (5.17 mmol) of N-methyl-4-bromo-2-methylaniline (Example 1, Step A) in 40 ml of THF at −78° C. was added dropwise 9.4 ml (15.98 mmol) of a 1.7M solution of tert-BuLi in hexanes and the resultant mixture was stirred at −78° C. for 30 min. To this mixture was then added 0.85 ml (4.98 mmol) of 3-(trifluoromethyl)-α,α,α-trifluoroacetophenone and the mixture was stirred at −78° C. for a 1.5 h. The reaction was quenched by the addition of a saturated aqueous solution of ammonium chloride, allowed to warm to room temperature, and extracted with EtOAc. The combined organic layers were washed with brine, dried over MgSO$_4$, filtered and the filtrate was concentrated to give the title compound which was used without further purification.

Step B. N-Methyl-N-{2-methyl-4-[2,2,2-trifluoro-1-hydroxy-1-(3-trifluoromethyl-phenyl)-ethyl]-phenyl}-benzenesulfonamide The title compound was prepared from 2,2,2-trifluoromethyl-1-(3-methyl-4-methylaminophenyl)-1-(3-trifluoromethyl-phenyl)-ethanol (Step A) and benzenesulfonyl chloride using the procedure described in Example 1, Step D. $^1$H-NMR (CDCl$_3$) δ 2.41 (s, 3H), 3.15 (s, 3H), 6.64 (d, J=8.4 Hz, 1H), 7.18 (brs, 1H), 7.42 (brs, 1H), 7.52-7.56 (m, 3H), 7.63-7.67 (m, 3H), 7.73 (d, J=8.5 Hz, 2H), 7.82 (s, 1H). Mass Spectrum (CI+) m/e 526.0 (M+23).

The compounds of Examples 6, 7 and 8 were prepared from 2,2,2-trifluoromethyl-1-(3-methyl-4-methylaminophenyl)-1-(3-trifluoromethyl-phenyl)-ethanol and an appropriate sulfonyl chloride using the methods described in Example 1, Step D.

Example 6

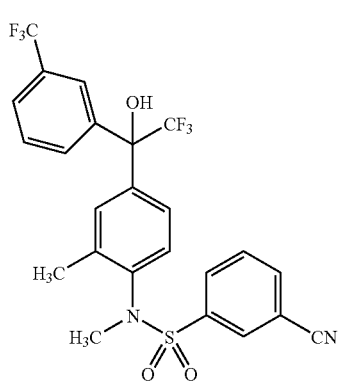

3-Cyano-N-methyl-N-{2-methyl-4-[2,2,2-trifluoro-1-hydroxy-1-(3-trifluoromethyl-phenyl)-ethyl]-phenyl}-benzenesulfonamide $^1$H-NMR (CDCl$_3$) δ 2.39 (s, 3H), 3.19 (s, 3H), 6.62 (d, J=8.4 Hz, 1H), 7.23 (brs, 1H), 7.45 (brs, 1H), 7.52-7.56 (m, 1H), 7.64-7.70 (m, 3H), 7.83 (s, 1H), 7.91-7.93 (m, 2H), 7.99-8.02 (m, 1H). Mass Spectrum (CI−) m/e=527.2 (M−1).

Example 7

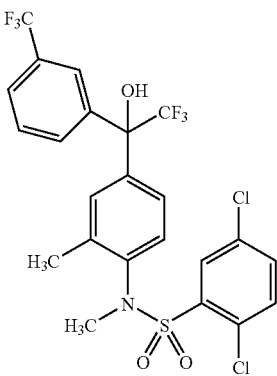

2,5-Dichloro-N-methyl-N-{2-methyl-4-[2,2,2-trifluoro-1-hydroxy-1-(3-trifluoromethyl-phenyl)-ethyl]-phenyl}-benzenesulfonamide $^1$H-NMR (CDCl$_3$) δ2.35 (s, 3H), 3.39 (s, 3H), 6.89 (d, J=8.4 Hz, 1H), 7.18-7.22 (m, 1H), 7.41 (brs, 1H), 7.48-7.53 (m, 3H), 7.60-7.66 (m, 2H), 7.83-7.86 (m, 2H0. Mass Spectrum (CI+) m/e=594.0 (M+23).

Example 8

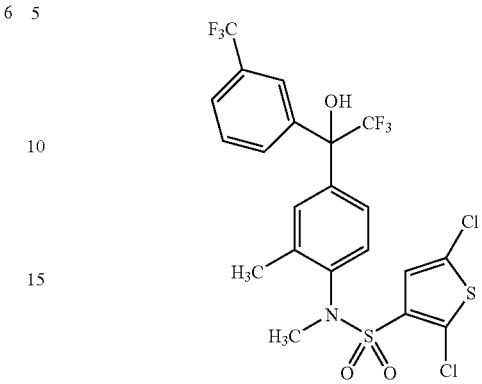

2,5-Dichloro-thiophene-3-sulfonic acid-N-methyl-N-{2-methyl-4-[2,2,2-trifluoro-1-hydroxy-1-(3-trifluoromethyl-phenyl)-ethyl]-phenyl}-amide $^1$H-NMR (CDCl$_3$) δ 2.40 (s, 3H), 3.29 (s, 3H), 6.91 (d, J=8.4 Hz, 1H), 6.96 (s, 1H), 7.26-7.28 (m, 1H), 7.44-7.54 (m, 2H), 7.65 (d, J=7.6 Hz, 2H), 7.81 (s, 1H). Mass Spectrum (CI+) m/e=600.0 (M+23).

The compounds of Examples 9-12 were prepared from N-methyl-4-bromo-2-methylaniline (Example 1, Step A) and trans-1,1,1-trifluoro-4-phenyl-3-buten-2-one (Aldrich Chemical Co.) as described in Example 5, Step A. Treatment of the resultant intermediate compounds with an appropriate sulfonyl chloride was carried out using methods described in Example 1, Step D.

Example 9

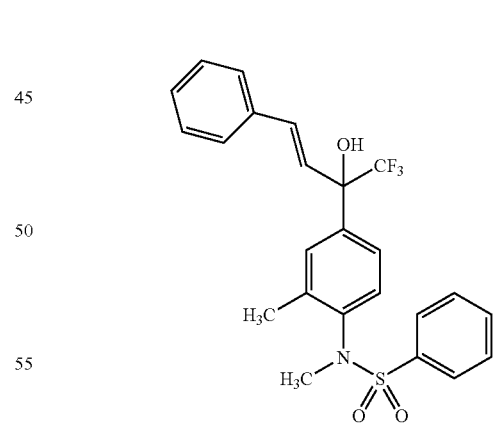

N-[4-(1-Hydroxy-3-phenyl-1-trifluoromethyl-allyl)-2-methyl-phenyl]-N-methyl-benzenesulfonamide $^1$H-NMR (CDCl$_3$) δ 2.44 (s, 3H), 3.15 (s, 3H), 6.65 (d, J=8.4 Hz, 1H), 6.68 (d, J=16 Hz, 1H), 6.91 (d, J=16 Hz, 1H), 7.33-7.46 (m, 4H), 7.59-7.76 (m, 6H), 7.93-7.96 (m, 2H). Mass Spectrum (CI−) m/e=460.1 (M−1).

Example 10

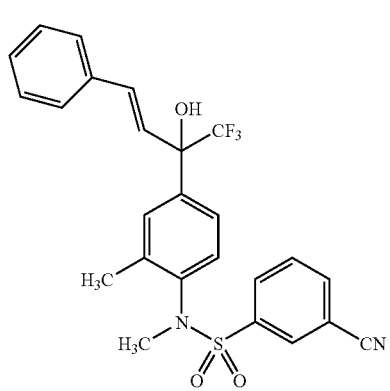

3-Cyano-N-[4-(1-hydroxy-3-phenyl-1-trifluoromethyl-allyl)-2-methyl-phenyl]-N-methyl-benzenesulfonamide $^1$H-NMR (CDCl$_3$) δ 2.43 (s, 3H), 3.20 (s, 3H), 6.63 (d, J=8.4 Hz, 1H), 6.69 (d, J=16 Hz, 1H), 6.92 (d, J=16 Hz, 1H), 7.28-7.47 (m, 5H), 7.60 (s, 1H), 7.69 (t, J=7.9 Hz, 1H), 7.91-7.95 (m, 2H), 8.06 (s, 1H). Mass Spectrum (CI−) m/e=485.1 (M−1).

Example 11

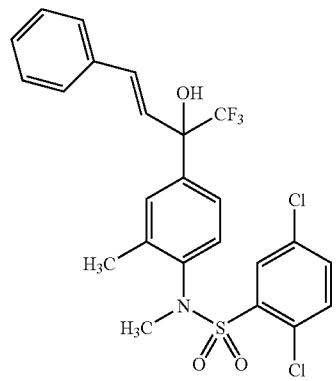

2,5-Dichloro-N-[4-(1-hydroxy-3-phenyl-1-trifluoromethyl-allyl)-2-methyl-phenyl]-N-methyl-benzenesulfonamide $^1$H-NMR (CDCl$_3$) δ 2.38 (s, 3H), 3.41 (s, 3H), 6.66 (d, J=16 Hz, 1H), 6.88 (d, J=16 Hz, 1H), 6.90 (d, J=8.4 Hz, 1H), 7.34-7.39 (m, 4H), 7.43-7.55 (m, 5H), 7.87 (s, 1H). Mass Spectrum (CI−) m/e=528.0 (M−1).

Example 12

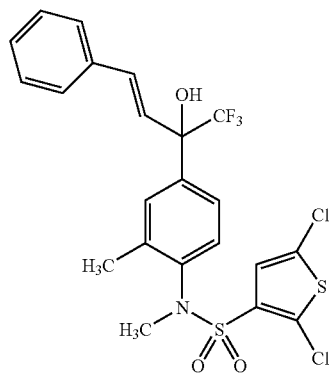

2,5-Dichloro-thiophene-3-sulfonic acid [4-(1-hydroxy-3-phenyl-1-trifluoromethyl-allyl)-2-methyl-phenyl]-methyl-amide $^1$H-NMR (CDCl$_3$) δ 2.44 (s, 3H), 3.30 (s, 3H), 6.69 (d, J=16.1 Hz, 1H), 6.88-6.97 (m, 3H), 7.33-7.47 (m, 6H), 7.59 (s, 1H). Mass Spectrum (CI−) m/e=534.0 (M−1).

The compounds of Examples 13-15 were prepared from N-methyl-4-bromoaniline and 2,2,2-trifluoroacetophenone (Aldrich Chemical Co.) using methods similar to those of Example 5, Step A. Treatment of the resultant intermediate compounds with an appropriate sulfonyl chloride was carried out using methods described in Example 1, Step D.

Example 13

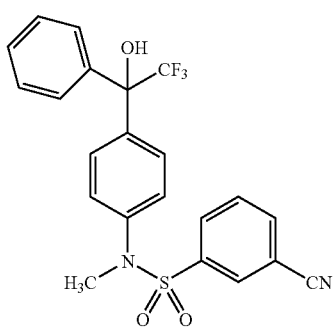

3-Cyano-N-methyl-N-[4-(2,2,2-trifluoro-1-hydroxy-1-phenethyl)]-benzenesulfonamide $^1$H-NMR (CDCl$_3$) δ 3.23 (s, 3H), 7.10 (d, J=8.4 Hz, 2H), 7.41-7.49 (m, 7H), 7.62 (t, J=7.8 Hz, 1H), 7.76-7.88 (m, 3H). Mass Spectrum (CI−) m/e=445.1 (M−1).

Example 14

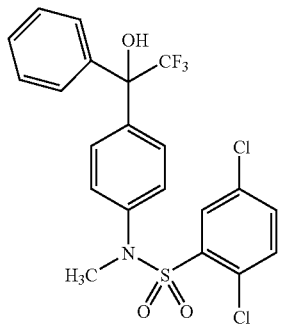

2,5-Dichloro-N-methyl-N-[4-(2,2,2-trifluoro-1-hydroxy-1-phenethyl)]-benzenesulfonamide $^1$H-NMR (CDCl$_3$) δ 3.42 (s, 3H), 7.23 (d, J=8.2 Hz, 2H), 7.37-7.46 (m, 9H), 7.88 (s, 1H). Mass Spectrum (CI−) m/e=488.1 (M−1).

Example 15

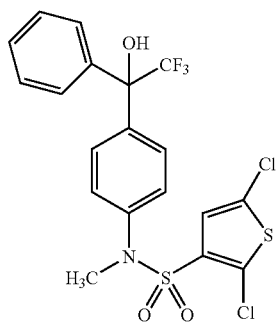

2,5-Dichlorothiophene-3-sulfonic acid methyl-[4-(2,2,2-trifluoro-1-hydroxy-1-phenyl-ethyl)-phenyl]-amide $^1$H-NMR (CDCl$_3$) δ 3.34 (s, 3H), 6.86 (s, 1H), 7.23 (d, J=8.4 Hz, 2H), 7.39-7.51 (m, 7H). Mass Spectrum (CI−) m/e=494.0 (M−1).

The compounds of Examples 16-18 were prepared from N-methyl-4-bromoaniline and 2,2,2-trifluoro-3'-(trifluoromethyl)acetophenone (Aldrich Chemical Co.) using methods similar to those of Example 5, Step A. Treatment of the resultant intermediate compounds with an appropriate sulfonyl chloride was carried out using methods described in Example 1, Step D.

Example 16

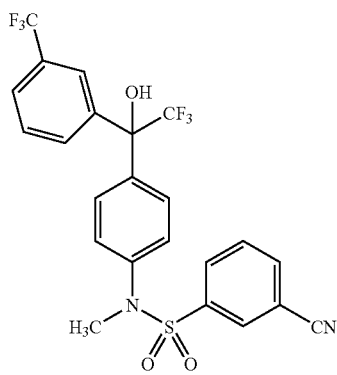

3-Cyano-N-methyl-N-{4-[2,2,2-trifluoro-1-hydroxy-1-(3-trifluoromethyl-phenyl)-ethyl]}-benzenesulfonamide $^1$H-NMR (CDCl$_3$) δ 3.23 (s, 3H), 7.14 (d, J=8.6 Hz, 2H), 7.15-7.88 (m, 10 H). Mass Spectrum (CI−) m/e=513.2 (M−1).

Example 17

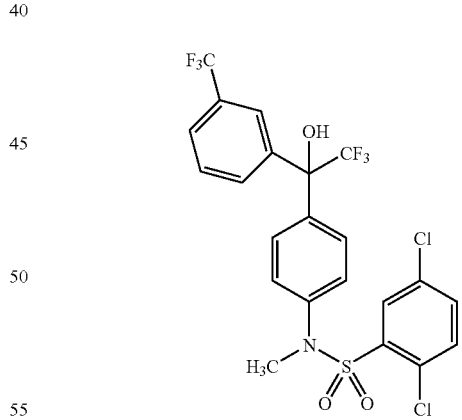

2,5-Dichloro-N-methyl-N-{4-[2,2,2-trifluoro-1-hydroxy-1-(3-trifluoromethyl-phenyl)-ethyl]}-benzenesulfonamide $^1$H-NMR (CDCl$_3$) δ 3.43 (s, 3H), 7.27-7.29 (m, 2H), 7.41-7.92 (m, 9H). Mass Spectrum (CI−) m/e=556.1 (M−1).

Example 18

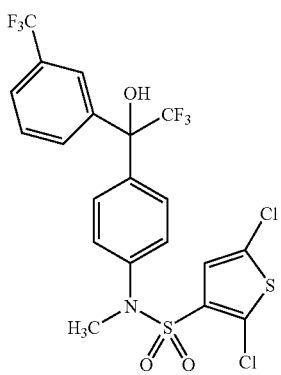

2,5-Dichlorothiophene-3-sulfonic acid methyl-{4-[2,2,2-trifluoro-1-hydroxy-1-(3-trifluoromethyl-phenyl)-ethyl]-phenyl}-amide $^1$H-NMR (CDCl$_3$) δ 6.34 (s, 3H), 6.89 (s, 1H), 7.27-7.29 (m, 2H), 7.48-7.55 (m, 3H), 7.66 (d, J=7.7 Hz, 2H), 7.78 (s, 1H). Mass Spectrum (CI−) m/e=562.1 (M−1).

The compounds of Examples 19-21 were prepared from N-methyl-4-bromoaniline and trans-1,1,1-trifluoro-4-phenyl-3-buten-2-one (Aldrich Chemical Co.) using methods similar to those of Example 5, Step A. Treatment of the resultant intermediate compound with an appropriate sulfonyl chloride was carried out using methods described in Example 1, Step D.

Example 19

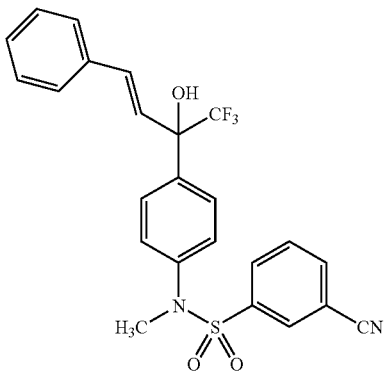

3-Cyano-N-[4-(1-hydroxy-3-phenyl-1-trifluoromethyl-allyl)-phenyl]-N-methyl-benzenesulfonamide $^1$H-NMR (CDCl$_3$) δ 3.24 (s, 3H), 6.71 (d, J=16 Hz, 1H), 6.91 (d, J=16 Hz, 1H), 7.15 (d, J=8.6 Hz, 2H), 7.34-7.47 (m, 5H), 7.61-7.65 (m, 3H), 7.74-7.76 (m, 1H), 7.86-7.89 (m, 2H). Mass Spectrum (CI−) m/e=471.2 (M−1).

Example 20

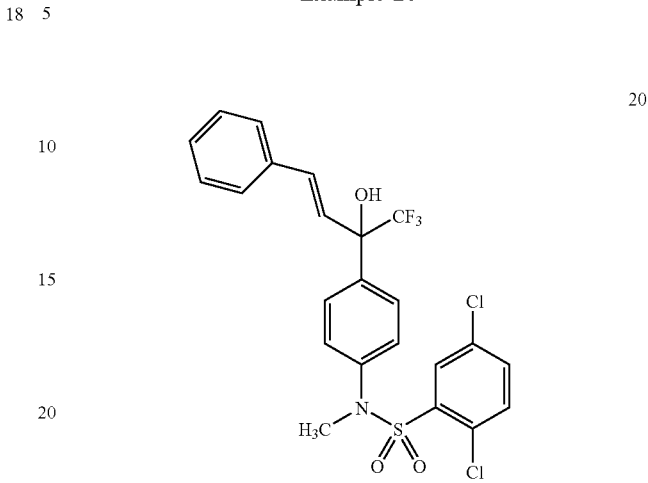

2,5-Dichloro-N-[4-(1-hydroxy-3-phenyl-1-trifluoromethyl-allyl)-phenyl]-N-methyl-benzenesulfonamide $^1$H-NMR (CDCl$_3$) δ 3.44 (s, 3H), 6.68 (d, J=16.1 Hz, 1H), 6.85 (d, J=16.1 Hz, 1H), 7.27-7.44 (m, 9H), 7.61 (d, J=8.6 Hz, 2H), 7.91 (s, 1H). Mass Spectrum (CI−) m/e=514.1 (M−1).

Example 21

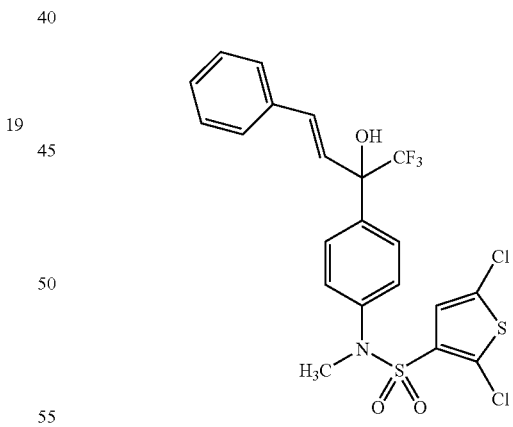

2,5-Dichlorothiophene-3-sulfonic acid [4-(1-hydroxy-3-phenyl-1-trifluoromethyl-allyl)-phenyl]-methyl-amide $^1$H-NMR (CDCl$_3$) δ 3.36 (s, 3H), 6.71 (d, J=16.2 Hz, 1H), 6.87 (d, J=15.9 Hz, 1H), 6.88 (s, 1H), 7.28-7.45 (m, 7H), 7.65 (d, J=8.6 Hz, 2H). Mass Spectrum (CI−) m/e=520.0 (M−1).

Example 22

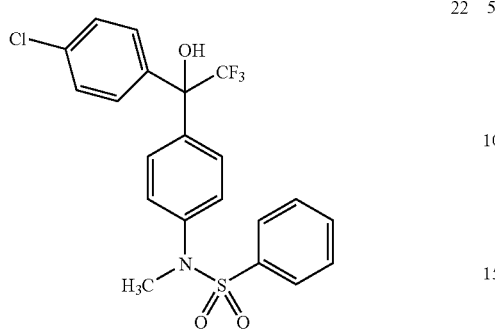

N-{4-[1-(4-Chlorophenyl)-2,2,2-trifluoro-1-hydroxy-ethyl]-phenyl}-N-methyl-benzenesulfonamide Step A. N-Methyl-N-(4-trifluoroacetyl-phenyl)-benzenesulfonamide To a suspension of 0.26 g of NaH 60% in mineral oil) in 5 mL of DMF was slowly added a solution of 0.98 g of N-methyl benzenesulfonamide in 4 mL of DMF at 0° C. After the addition, the reaction mixture was allowed to warm to room temperature. After 1 h a solution of 1 g of 1,1,1,4'-tetraflouroacetophenone in 1 mL of DMF was added and the reaction mixture was stirred at 60° C. for 12 h. The solvent was removed under reduced pressure, the residue was dissolved in AcOEt (80 mL) and washed with sat. NaHCO$_3$ solution (2×20 mL) and brine (20 mL). The organic layer was dried over MgSO$_4$, filtered and the filtrate was concentrated. The residue was purified by flash chromatography on silica (ethyl acetate/hexane=1/1) to give the title compound. $^1$H-NMR (CDCl$_3$) δ 3.27 (s, 3 H), 7.37 (d, J=6.0 Hz, 2 H), 7.48-7.63 (m, 5 H), 8.04 (d, J=6 Hz, 2 H). Mass Spectrum (CI+) m/e=344 (M+1).

Step B. N-{4-[1-(4-Chlorophenyl)-2,2,2-trifluoro-1-hydroxy-ethyl]-phenyl}-N-methyl-benzenesulfonamide To a solution of 0.2 g of N-methyl-N-(4-trifluoroacetyl-phenyl)-benzenesulfonamide in 10 mL of THF were added 0.7 mL of a 1 M solution 4-chlorophenyl magnesium bromide at −78° C. The resulting mixture was stirred at −78° C. for 4 hr. After this time, the reaction mixture was quenched by the addition of a saturated aqueous solution of ammonium chloride and extracted with EtOAc. The combined organic layers were washed with brine, dried over MgSO$_4$, filtered and the filtrate was concentrated. The residue was purified by chromatography on silica gel (hexanes:EtOAc, 7:1) to give the title compound. $^1$H-NMR (CDCl$_3$) δ 2.96 (br s, 1 H), 3.17 (s, 3 H), 7.10-7.59 (m, 13 H). Mass Spectrum (CI+) m/e=456 (M+1).

Example 23

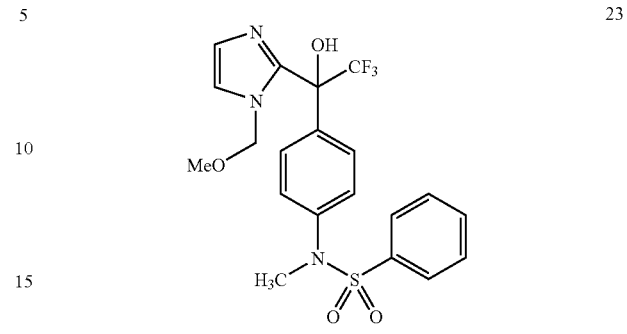

N-Methyl-N-{4-[2,2,2-trifluoro-1-hydroxy-1-(1-methoxymethyl-1H-imidazol-2-yl)-ethyl]-phenyl}-benzenesulfonamide Step A. 1-Methoxymethyl-1H-imidazole To a solution of 1.06 g of imidazole (15.56 mmol) in 20 ml of THF at 0° C. was added 658 mg (16.45 mmol) of NaH (40% dispersion in oil) and the mixture was stirred at 0° C. for 30 mins. After this time, 1.2 ml (15.7 mmol) of chloromethyl methyl ether were added and the mixture was allowed to warm to room temperature and stirred for 14 h. After this time the reaction was quenched by the addition of a saturated aqueous solution of ammonium chloride, allowed to warm to room temperature, and extracted with EtOAc. The combined organic layers were washed with brine, dried over MgSO$_4$, filtered and the filtrate was concentrated. The residue was purified by chromatography on silica gel (hexanes:EtOAc, 1:1) to give the title compound. $^1$H-NMR (CDCl$_3$) δ 3.21 (s, 3H), 5.18 (s, 2H), 7.00 (d, J=19 Hz, 2H0, 7.54 (s, 1H).

Step B. N-Methyl-N-{4-[2,2,2-trifluoro-1-hydroxy-1-(1-methoxymethyl-1H-imidazol-2-yl)-ethyl]-phenyl}-benzenesulfonamide To a solution of 55 mg (0.49 mmol) of 1-methoxymethyl-1H-imidazole in 5 ml of THF at −78° C. was added 0.20 ml (0.50 mmol) of a 2.5 M solution of n-butyllithium in hexanes and the resultant mixture was stirred at −78° C. for 30 mins. After this time, a solution of 160 mg (0.47 mmol) of N-methyl-N-(4-trifluoroacetyl-phenyl)benzenesulfonamide (Example 22, Step A) in 2 ml of THF was added and the resultant mixture stirred at −78° C. for a further 2 h, and then at room temperature for 14 h. After this time the reaction was quenched by the addition of a saturated aqueous solution of ammonium chloride and extracted with EtOAc. The combined organic layers were washed with brine, dried over MgSO$_4$, filtered and the filtrate was concentrated. The residue was purified by chromatography on silica gel (hexanes:EtOAc, 4:1) to give the title compound. $^1$H-NMR (CDCl$_3$) δ 3.09 (s, 3H), 3.19 (s, 3H), 4.90 (s, 2H), 5.16 (brs, 1H), 7.07-7.16 (m, 4H), 7.42-7.62 (m, 7H). Mass Spectrum (CI+) m/e=456.1 (M+1).

Example 24 was prepared from benzimidazole and N-methyl-N-(4-trifluoroacetyl-phenyl)-benzenesulfonamide (Example 22, Step A) following procedures described in Example 23.

Example 24

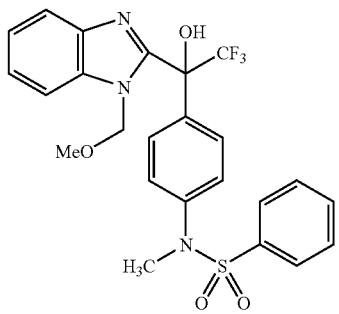

N-Methyl-N-{4-[2,2,2-trifluoro-1-hydroxy-1-(1-methoxymethyl-1H-benzoimidazol-2-yl)-ethyl]-phenyl}-benzenesulfonamide $^1$H-NMR (CDCl$_3$) δ 3.12 (s, 3H), 3.19 (s, 3H), 5.10 (d, J=10.8 Hz, 1H), 5.26 (d, J=10.9 Hz, 1H), 7.15-7.17 (m, 2H), 7.36-7.59 (m, 1H). Mass Spectrum (CI+) m/e=506.0 (M+1).

Examples 25-28 were prepared from the appropriate heterocycle and N-methyl-N-(4-trifluoroacetyl-phenyl)-benzenesulfonamide (Example 22, Step A) following procedures described in Example 23, Step B.

Example 25

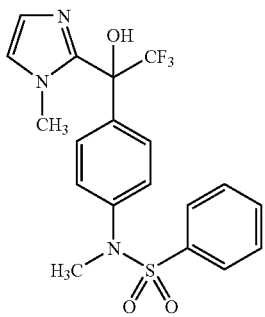

N-Methyl-N-{4-[2,2,2-trifluoro-1-hydroxy-1-(1-methyl-1H-imidazol-2-yl)-ethyl]-phenyl}-benzenesulfonamide $^1$H-NMR (CDCl$_3$) δ 3.19 (s, 3H), 3.22 (s, 3H), 6.87 (s, 1H), 6.98 (s, 1H), 7.14 (d, J=8.6 Hz, 2H), 7.37 (d, J=8.5 Hz, 2H), 7.43-7.61 (m, 5H). Mass Spectrum (CI+) m/e=426.0 (M+1).

Example 26

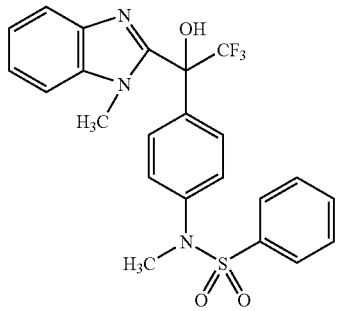

N-Methyl-N-{4-[2,2,2-trifluoro-1-hydroxy-1-(1-methyl-1H-benzoimidazol-2-yl)-ethyl]-phenyl}-benzenesulfonamide $^1$H-NMR (CDCl$_3$) δ 3.20 (s, 3H), 3.33 (s, 3H), 7.17-7.55 (m, 12H), 7.81 (d, J=7.5 Hz, 1H). Mass Spectrum (CI+) m/e=476.0 (M+1).

Example 27

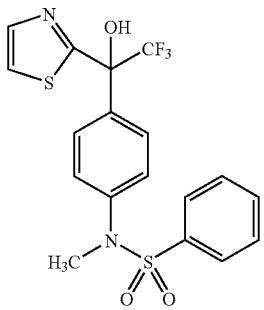

N-Methyl-N-{4-[2,2,2-trifluoro-1-hydroxy-1-(1-thiazol-2-yl)-ethyl]-phenyl}-benzenesulfonamide $^1$H-NMR (CDCl$_3$) δ 3.20 (s, 3H), 5.34 (brs, 1H), 7.18 (d, J=8.6 Hz, 2H), 7.46-7.59 (m, 6H), 7.75 (d, J=8.5 Hz, 2H), 7.85 (d, J=3.2 Hz, 1H). Mass Spectrum (CI+) m/e=429.0 (M+1).

Example 28

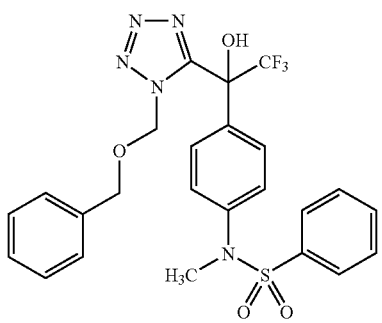

N-{4-[1-Benzyloxymethyl-1-H-tetrazol-5-yl)-2,2,2-trifluoro-1-hydroxy-ethyl]-phenyl}-N-methyl-benzenesulfonamide $^1$H-NMR (CDCl$_3$) δ 3.20 (s, 3H), 4.73 (s, 2H), 6.01 (s, 2H), 7.18-7.21 (m, 2H), 7.32-7.61 (m, 10H, 7.84 (d, J=8.7 Hz, 2H). Mass Spectrum (CI+) m/e=534.1 (M+1).

Example 29

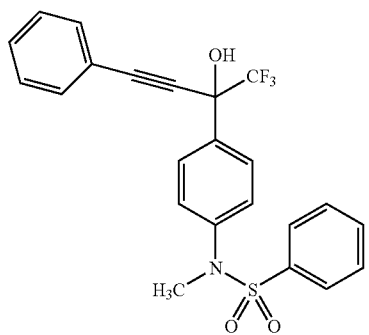

N-[4-(1-Hydroxy-3-phenyl-1-trifluoromethyl-prop-2-ynyl)-phenyl]-N-methyl-benzenesulfonamide To a solution of 0.18 g of phenylacetylene (1.75 mmol) in 5 mL of THF was added dropwise 0.76 mL of n-BuLi (2.5M in hexane) at −78° C. The color of the solution turned dark blue and the mixture was stirred at −78° C. for 30 min. Then 0.5 g of N-methyl-N-(4-trifluoroacetyl-phenyl)-benzenesulfonamide (Example 22, Step A) in 5 ml of THF was added and the resultant mixture stirred at −78° C. for 2 h. After this time the reaction was quenched by the addition of a saturated aqueous solution of ammonium chloride and extracted with EtOAc. The combined organic layers were washed with brine, dried over MgSO$_4$, filtered and the filtrate was concentrated. The residue purified by chromatography on silica gel (hexanes:EtOAc, 7:3) to give the title compound. $^1$H NMR (CDCl$_3$) δ 3.19 (s, 3 H), 3.26 (br s, 1 H), 7.17 (d, J=8.7 Hz, 2 H), 7.34-7.60 (m, 10 H), 7.74 (d, J=8.7 Hz, 2 H). Mass Spectrum (CI+) m/e=446.0 (M+1).

Example 30

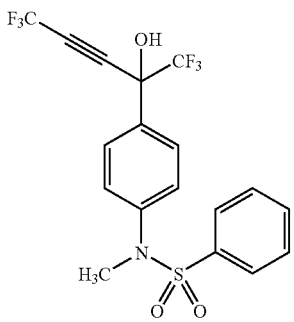

N-Methyl-N-[4-(4,4,4-trifluoro-1-hydroxy-1-trifluoromethyl-but-2-ynyl)-phenyl]-benzenesulfonamide The compound was prepared from N-methyl-N-(4-trifluoroacetyl-phenyl)-benzenesulfonamide (Example 22, Step A) and 3,3,3-trifluoroprop-1-yne following the procedure described in Example 29. $^1$H NMR (CDCl$_3$) δ 3.19 (s, 3 H), 4.30 (br s, 1H), 7.11-7.63 (m, 9 H). Mass Spectrum (CI+) m/e=438 (M+1).

Example 31

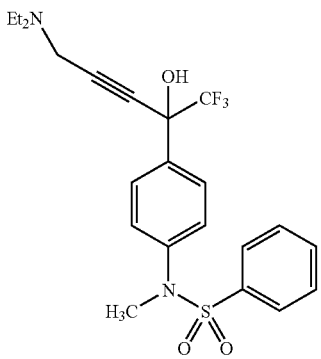

N-[4-(4-Diethylamino-1-hydroxy-1-trifluoromethyl-but-2-ynyl)-phenyl]-N-methyl-benzenesulfonamide The compound was prepared from N-methyl-N-(4-trifluoroacetyl-phenyl)-benzenesulfonamide (Example 22, Step A) and 3-(diethylamino)-propy-1-yne following the procedure described in Example 29. $^1$H NMR (CDCl$_3$) δ 1.09 (t, J=7.1 Hz, 6 H), 2.59 (q, J=7.1 Hz, 4 H), 3.17 (s, 3 H), 3.52 (s, 2 H), 5.34 (brs, 1H), 7.13 (d, J=8.5 HZ, 2 H), 7.41-7.58 (m, 5 H), 7.66 (d, J=8.5 Hz, 2 H). Mass Spectrum (CI+) m/e=455 (M+1).

Example 32

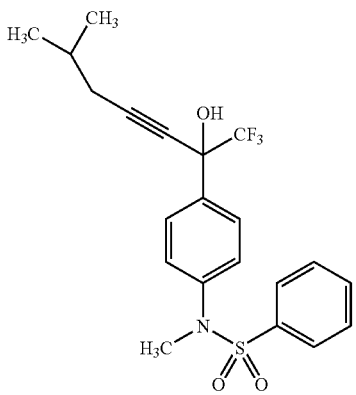

N-[4-(1-Hydroxy-5-methyl-1-trifluoromethyl-hex-2-ynyl)-phenyl]-N-methyl-benzenesulfonamide The compound was prepared from N-methyl-N-(4-trifluoroacetyl-phenyl)-benzenesulfonamide (Example 22, Step A) and 4-methyl-pent-1-yne following the procedure described in Example 29. $^1$H NMR (CDCl$_3$) δ 1.01 (d, J=6.6 Hz, 6 H), 1.90 (sept, J=6.6 Hz, 1 H), 2.21 (d, J=7.7 Hz, 2 H), 3.17 (s, 3 H), 3.24 (br s, 1 H), 7.12-7.68 (m, 9 H). Mass Spectrum (CI+) m/e=426 (M+1).

Example 33

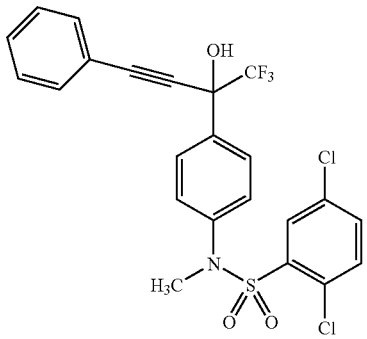

2,5-Dichloro-N-[4-(1-hydroxy-3-phenyl-1-trifluoromethyl-prop-2-ynyl)-phenyl]-N-methyl-benzenesulfonamide Step A. N-Methyl-N-(4-trifluoroacetyl-phenyl)-benzenesulfonamide The title compound was prepared from 1,1,1,4'-tetrafluoroacetophenone and 2,5-dichloro-N-methyl-benzenesulfonamide using methods similar to those described in Example 22 Step A. $^1$H NMR (400 MHz, CDCl$_3$) δ 3.48 (s, 3 H), 7.41-8.05 (m, 7 H).

Step B. 2,5-Dichloro-N-[4-(1-hydroxy-3-phenyl-1-trifluoromethyl-prop-2-ynyl)-phenyl]-N-methyl-benzenesulfonamide The title compound was prepared from N-methyl-N-(4-trifluoroacetyl-phenyl)-benzenesulfonamide using methods as described in Example 29. $^1$H NMR (400 MHz, CDCl$_3$) δ=3.21 (brs, 1H), 3.43 (s, 3 H), 7.3 (d, J=8.8 Hz, 2 H), 7.34-7.53 (m, 7 H), 7.75 (d, J=8.8 Hz, 2 H), 7.91 (s, 1 H). Mass Spectrum (CI+) m/e=516 (M+1).

Example 34

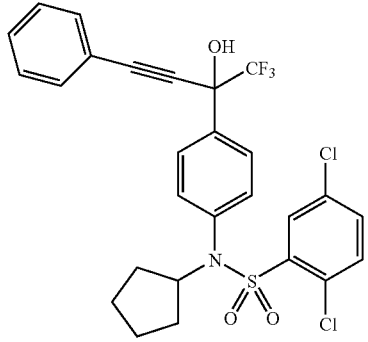

N-Cyclopentyl-2,5-dichloro-N-[4-(1-hydroxy-3-phenyl-1-trifluoromethyl-prop-2-ynyl)-phenyl]-benzenesulfonamide Step A. 1-(4-Cyclopentylamino-phenyl)-2,2,2-trifluoro-ethanone To a mixture of 3.94 g of 2,2,2,4'-tetrafluoroacetophenone (20.5 mmol) and 3.35 ml triethylamine (24.0 mmol) in 40 ml of acetonitrile at 0° C. were added 5.9 ml of cyclopentylamine (59.8 mmol). The reaction was allowed to warm to room temperature and then heated to reflux for 14 h. After this time the reaction mixture was cooled to room temperature, concentrated and partitioned between water and EtOAc. The organic layer was dried over MgSO$_4$, filtered and the filtrate was concentrated. The residue was purified by chromatography on silica (hexanes:EtOAc, 4:1) to give the title compound. $^1$H-NMR (CDCl$_3$) δ 1.53-1.57 (m, 2H), 1.69-1.78 (m, 4H), 2.08-2.13 (m, 2H), 3.88-3.95 (m, 1H), 4.63 (brs, 1H), 6.60 (d, J=8.9 Hz, 2H), 7.92 (d, J=8.9 Hz, 2H). Mass Spectrum (CI+) m/e=258.1 (M+1).

Step B. 2-(4-Cyclopentylamino-phenyl)-1,1,1-trifluoro-4-phenyl-but-3-yn-2-ol

To a solution of 0.4 ml of phenylacetylene (3.6 mmol in 10 ml of THF at −78° C. was added 1.9 ml (4.75 mmol) of a 2.5 M solution of n-butyllithium in hexanes. The color of the solution turned dark blue and the reaction mixture was stirred at −78° C. for 30 min. After this time, a solution of 450 mg of 1-(4-cyclopentylamino-phenyl)-2,2,2-trifluoroethanone (1.75 mmol) in 2 ml of THF was added and the resultant mixture stirred at −78° C. for 1.5 h before being allowed to warm to room temperature and stirred for a further 14 h. After this time, the reaction was quenched by the addition of a saturated aqueous solution of ammonium chloride and extracted with EtOAc. The combined organic layers were washed with brine, dried over MgSO$_4$, filtered and the filtrate was concentrated. The residue was purified by chromatography on silica (hexanes:EtOAc, 3:1) to give the title compound. $^1$H-NMR (CDCl$_3$) δ 1.48-1.56 (m, 2H), 1.68-1.76 (m, 4H), 2.03-2.14 (m, 2H), 3.76-3.85 (m, 1H), 6.65 (d, J=8.6 Hz, 2H), 7.36-7.82 (m, 10H). Mass Spectrum (CI+) m/e=360.1 (M+1).

Step C. 2,5-Dichloro-N-cyclopentyl-N-[4-(1-hydroxy-3-phenyl-1-trifluoromethyl-prop-2-ynyl)-phenyl]-benzenesulfonamide A mixture of 53 mg of 2-(4-cyclopentylamino-phenyl)-1,1,1-trifluoro-4-phenyl-but-3-yn-2-ol (0.15 mmol) and 44 mg of 2,5-dichlorobenzenesulfonyl chloride (0.18 mmol) in 0.2 ml of pyridine was heated to 70° C. for 14 hours. After this time the reaction mixture was allowed to cool to room temperature, quenched by the addition of a saturated aqueous solution of ammonium chloride, and extracted with EtOAc. The combined organic layers were washed with brine, dried over MgSO$_4$, filtered and the filtrate was concentrated. The residue was purified by chromatography on silica (hexanes:EtOAc, 4:1) to give the title compound. $^1$H-NMR (CDCl$_3$) δ 1.36-1.58 (m, 6H), 1.97-2.07 (m, 2H), 4.73-4.78 (m, 1H), 7.18 (d, J=8.4 Hz, 2H), 7.37-7.55 (m, 7H), 7.76 (d, J=8.4 Hz, 2H), 7.84 (d, J=2.4 Hz, 1H). Mass Spectrum (CI+) m/e=590.0 (M+23).

Examples 35 and 36 were prepared from 2-(4-cyclopentylamino-phenyl)-1,1,1-trifluoro-4-phenyl-but-3-yn-2-ol (described in Example 34, Step B) and an appropriate sulfonyl chloride using methodology as described in Example 34, Step C.

Example 35

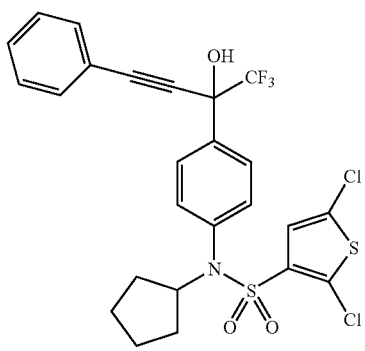

2,5-Dichloro-thiophene-3-sulfonic acid N-cyclopentyl[4-(1-hydroxy-3-phenyl-1-trifluoromethyl-prop-2-ynyl)-phenyl]-amide $^1$H-NMR (CDCl$_3$) δ 1.27-1.53 (m, 6H), 1.93-1.96 (m, 2H), 3.38 (brs, 1H), 4.61-4.68 (m, 1H), 6.95 (s, 1H), 7.20 (d, J=8.2 Hz, 2H), 7.37-7.44 (m, 3H), 7.55 (m, 2H), 7.83 (d, J=8.3 Hz, 2H). Mass Spectrum (CI+) m/e=596.0 (M+23).

Example 36

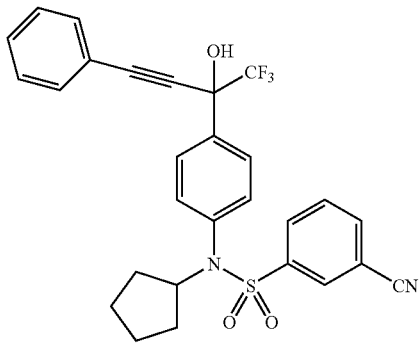

3-Cyano-N-cyclopentyl-N-[4-(1-hydroxy-3-phenyl-1-trifluoromethyl-prop-2-ynyl)-phenyl]-benzenesulfonamide $^1$H-NMR (CDCl$_3$) δ 1.25-1.36 (m, 2H), 1.48-1.52 (m, 4H), 1.86-1.88 (m, 2H), 4.23 (brs, 1H), 4.54-4.60 (m, 1H), 7.08 (d, J=8.6 Hz, 2H), 7.36-7.42 (m, 3H), 7.52-7.64 (m, 3H), 7.82-7.87 (m, 3H), 7.92-7.95 (m, 1H), 8.06 (s, 1H). Mass Spectrum (CI+) m/e=547.1 (M+23).

Example 37

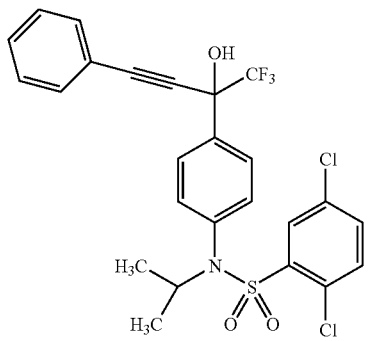

2,5-Dichloro-N-[4-(1-hydroxy-3-phenyl-1-trifluoromethyl-prop-2-ynyl)-phenyl]-N-isopropyl-benzenesulfonamide Step A. 1-(4-Isopropylamino-phenyl)-2,2,2-trifluoro-ethanone The title compound was prepared as described in Example 34, Step A, substituting isopropylamine for cyclopentylamine. $^1$H-NMR (CDCl$_3$) δ 1.29 (d, J=6.3 Hz, 6H), 3.76-3.80 (m, 1H), 4.48 (brs, 1H), 6.58 (d, J=8.6 Hz, 2H), 7.93 (d, J=8.9 Hz, 2H). Mass Spectrum (CI+) m/e=232 (M+1).

Step B. 2-(4-Isopropylamino-phenyl)-1,1,1-trifluoro-4-phenyl-but-3-yn-2-ol

The title compound was prepared as described in Example 34, Step B. $^1$H-NMR (CDCl$_3$) δ 1.25 (d, J=6.3 Hz, 6H), 3.36 (brs, 1H), 3.66-3.70 (m, 1H), 6.63 (d, J=8.6 Hz, 2H), 7.28-7.64 (m, 7H). Mass Spectrum (CI+) m/e=334.1 (M+1).

Step C. 2,5-Dichloro-N-[4-(1-hydroxy-3-phenyl-1-trifluoromethyl-prop-2-ynyl)-phenyl]-N-isopropyl-benzenesulfonamide The title compound was prepared from 2-(4-isopropylamino-phenyl)-1,1,1-trifluoro-4-phenyl-but-3-yn-2-ol using methods as described in Example 34, Step C. $^1$H-NMR (CDCl$_3$) δ 1.20 (m, 6H), 4.73-4.78 (m, 1H), 7.18 (d, J=8.6 Hz, 2H), 7.38-7.55 (m, 7H), 7.78 (d, J=8.4 Hz, 2H), 7.86 (d, J=2.4 Hz, 1H). Mass Spectrum (CI+) m/e=564.0 (M+23).

Examples 38 and 39 were prepared from 2-(4-isopropylamino-phenyl)-1,1,1-trifluoro-4-phenyl-but-3-yn-2-ol and appropriate sulfonyl chlorides using methods as described in Example 34, Step C.

Example 38

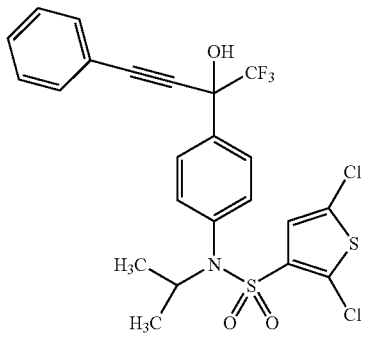

2,5-Dichloro-thiophene-3-sulfonic acid N-[4-(1-hydroxy-3-phenyl-1-trifluoromethyl-prop-2-ynyl)-phenyl]-N-isopropyl-amide $^1$H-NMR (CDCl$_3$) δ 1.16-1.18 (m, 6H), 4.68-4.73 (m, 1H), 6.96 (s, 1H), 7.20-7.22 (m, 2H), 7.39-7.44 (m, 3H), 7.54-7.57 (m, 2H), 7.84 (d, J=8.4 Hz, 2H). Mass Spectrum (CI+) m/e=569.9 (M+23).

Example 39

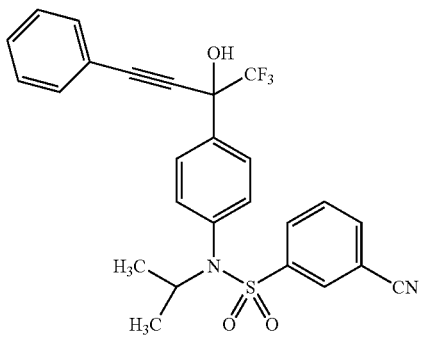

3-Cyano-N-[4-(1-hydroxy-3-phenyl-1-trifluoromethyl-prop-2-ynyl)-phenyl]-N-isopropyl-benzenesulfonamide $^1$H-NMR (CDCl$_3$) δ 1.09-1.12 (m, 6H), 4.62-4.67 (m, 1H), 7.09-7.11 (m, 2H), 7.37-7.44 (m, 3H), 7.54-7.65 (m, 3H), 7.83-7.86 (m, 3H), 7.94-7.97 (m, 1H), 8.06-8.07 (m, 1H). Mass Spectrum (CI+) m/e=521.0 (M+23).

Example 40

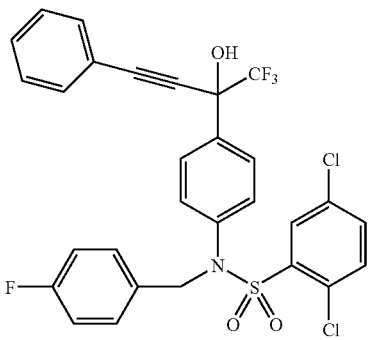

2,5-Dichloro-N-(4-fluorobenzyl)-N-[4-(1-hydroxy-3-phenyl-1-trifluoromethyl-prop-2-ynyl)-phenyl]-benzenesulfonamide

Step A. 1-[4-(4-Fluorobenzylamino)-phenyl]-2,2,2-trifluoro-ethanone

The title compound was prepared as described in Example 34, Step A, substituting 4-fluorobenzylamine for cyclopentylamine. $^1$H-NMR (CDCl$_3$) δ 4.45 (s, 2H), 4.99 (br s, 1H), 6.63-6.67 (m, 2H), 7.07-7.09 (m, 2H), 7.31-7.35 (m, 2H), 7.93 (d, J=8.1 Hz, 2H). Mass Spectrum (CI+) m/e=298.1 (M+1).

Step B. 2-[4-(4-Fluorobenzyl)amino)-phenyl]-1,1,1-trifluoro-4-phenyl-but-3-yn-2-ol The title compound was prepared as described in Example 34, Step B, starting with 1-[4-(4-Fluorobenzylamino)-phenyl]-2,2,2-trifluoro-ethanone and was used without further purification. Mass Spectrum (CI+) m/e=400.1 (M+1).

Step C. 2,5-Dichloro-N-(4-fluorobenzyl)-N-[4-(1-hydroxy-3-phenyl-1-trifluoromethyl-prop-2-ynyl)-phenyl]-benzenesulfonamide The title compound was prepared as described in Example 34, Step C, starting with 2-[4-(4-Fluorobenzyl)amino)-phenyl]-1,1,1-trifluoro-4-phenyl-but-3-yn-2-ol. $^1$H-NMR (CDCl$_3$) δ 4.98-5.08 (m, 2H), 6.98 (t, J=8.6 Hz, 2H), 7.14 (d, J=8.6 Hz, 2H), 7.23-7.26 (m, 2H), 7.34-7.52 (m, 7H), 7.67 (d, J=8.5 Hz, 2H), 7.86 (d, J=2.4 Hz, 1H). Mass Spectrum (CI+) m/e=630.0 (M+23).

Example 41

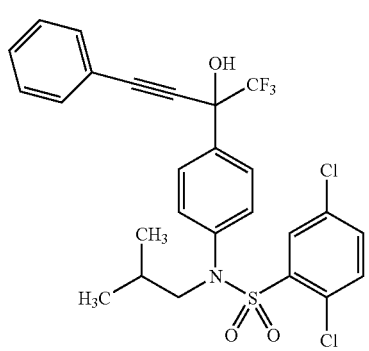

2,5-Dichloro-N-[4-(1-hydroxy-3-phenyl-1-trifluoromethyl-prop-2-ynyl)-phenyl]-N-isobutyl-benzenesulfonamide

Step A. 1-(4-Isobutylamino-phenyl)-2,2,2-trifluoroethanone

The title compound was prepared as described in Example 34, Step A, substituting isobutylamine for cyclopentylamine. $^1$H NMR (CDCl$_3$) δ 1.0 (d, J=6.7 Hz, 6 H), 1.92 (tsept, J=6.7, 6.7 Hz, 1 H), 3.05 (dd, J=6.7, 5.8 Hz, 2 H), 4.69 (br s, 1 H), 6.58 (d, J=9.1 Hz, 2 H), 7.90 (d, J=9.1 Hz, 2 H). Mass Spectrum (CI+) m/e=246 (M+1).

Step B. 2-(4-Isobutylamino-phenyl)-1,1,1-trifluoro-4-phenyl-but-3-yn-2-ol

The title compound was prepared as described in Example 34, Step B, starting with 1-(4-isobutylamino-phenyl)-2,2,2-trifluoro-ethanone. $^1$H NMR (CDCl$_3$) δ 0.99 (d, J=6.7 Hz, 6 H), 1.92 (tsept, J=6.7, 6.0 Hz, 1 H), 2.96 (d, J=6.0 Hz, 2 H), 3.03 (br s, 1 H), 3.90 (br s, 1 H), 6.61 (d, J=8.8 Hz, 2 H), 7.34-7.55 (m, 5 H), 7.58 (d, J=8.8 Hz, 2 H). Mass Spectrum (CI+) m/e=348 (M+1).

Step C. 2,5-Dichloro-N-[4-(1-hydroxy-3-phenyl-1-trifluoromethyl-prop-2-ynyl)-phenyl]-N-isobutyl-benzenesulfonamide The title compound was prepared as described in Example 34, Step C, starting with 2-(4-isobutylamino-phenyl)-1,1,1-trifluoro-4-phenyl-but-3-yn-2-ol. $^1$H NMR (CDCl$_3$) δ 0.96 (m, 6 H), 1.67 (m, 1 H), 3.19 (br s, 1 H), 3.68 (d, J=7.3 Hz, 2 H), 7.31 (d, J=8.5 Hz, 2 H), 7.34-7.52 (m, 7 H), 7.73 (d, J=8.5 Hz, 2 H), 7.80 (d, J=2.4 Hz, 1 H). Mass Spectrum (CI+) m/e=578 (M+23).

Examples 42 and 43 were prepared from 2-(4-isobutylamino-phenyl)-1,1,1-trifluoro-4-phenyl-but-3-yn-2-ol and an appropriate sulfonyl chloride using methods as described in Example 34, Step C.

Example 42

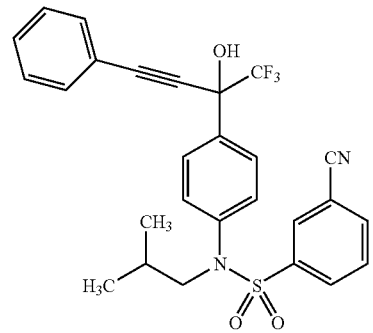

3-Cyano-N-[4-(1-hydroxy-3-phenyl-1-trifluoromethyl-prop-2-ynyl)-phenyl]-N-isobutyl-benzenesulfonamide $^1$H NMR (CDCl$_3$) δ, 0.93 (m, 6 H), 1.61 (m, 1 H), 3.36 (m, 2 H), 3.42 (br s, 1 H), 7.11 (d, J=8.0 Hz, 2 H), 7.35-7.73 (m, 7 H), 7.78 (d, J=8.0 Hz, 2 H), 7.83 (dd, J=7.7, 1.1 Hz, 1 H), 7.89 (s, 1 H). Mass Spectrum (CI+) m/e=535 (M+23).

Example 43

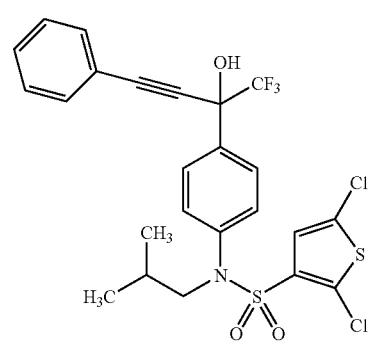

2,5-Dichloro-thiophene-3-sulfonic acid N-isobutyl [4-(1-hydroxy-3-phenyl-1-trifluoromethyl-prop-2-ynyl)-phenyl]-amide $^1$H NMR (CDCl$_3$) δ 0.93 (m, 6 H), 1.65 (m, 1 H), 3.27 (br s, 1 H), 3.52 (d, J=7.4 Hz, 2 H), 6.84 (s, 1 H), 7.27 (d, J=8.5 Hz, 2 H), 7.35-7.54 (m, 5 H), 7.80 (d, J=8.5 Hz, 2 H). Mass Spectrum (CI+) m/e=584 (M+23).

Example 44

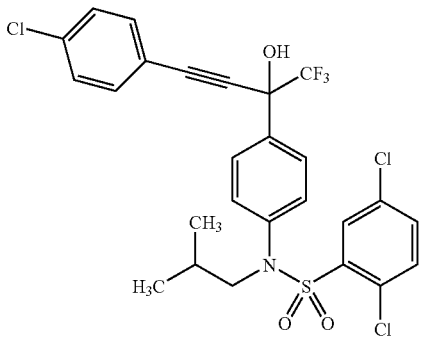

2,5-Dichloro-N-{4-[3-(4-chloro-phenyl)-1-hydroxy-1-trifluoromethyl-prop-2-ynyl]-phenyl}-N-isobutyl-benzenesulfonamide Step A. 4-(4-Chlorophenyl)-1,1,1-trifluoro-2-(4-isobutylamino-phenyl)-but-3-yn-2-ol The title compound was prepared from 1-(4-isobutylamino-phenyl)-2,2,2-trifluoro-ethanone (Example 41, Step A) as described in Example 34, Step B and substituting 4-chlorophenylacetylene for phenylacetylene. $^1$H NMR (400 MHz, CDCl$_3$) δ 0.98 (m, 6 H), 1.90 (m, 1 H), 2.96 (brs, 1 H), 2.96 (m, 2 H), 3.92 (br s, 1 H), 6.59-7.56 (m, 8 H). Mass Spectrum (CI+) m/e=382 (M+1).

Step B. 2,5-Dichloro-N-{4-[3-(4-chloro-phenyl)-1-hydroxy-1-trifluoromethyl-prop-2-ynyl]-phenyl}-N-isobutyl-benzenesulfonamide The title compound was prepared using methods as described in Example 34, Step C. $^1$H NMR (400 MHz, CDCl$_3$) δ 0.96 (m, 6 H), 1.67 (m, 1 H), 3.51 (br s, 1 H), 3.67 (m, 2 H), 7.30-7.45 (m, 8 H), 7.71 (d, J=8.8 Hz, 2 H), 7.80 (d, J=2.4 Hz, 1 H). Mass Spectrum (CI+) m/e=592 (M+1).

Example 45 and 46 were prepared from 4-(4-chlorophenyl)-1,1,1-trifluoro-2-(4-isobutylamino-phenyl)-but-3-yn-2-ol and an appropriate sulfonyl chloride using methods as described in Example 34, Step C.

Example 45

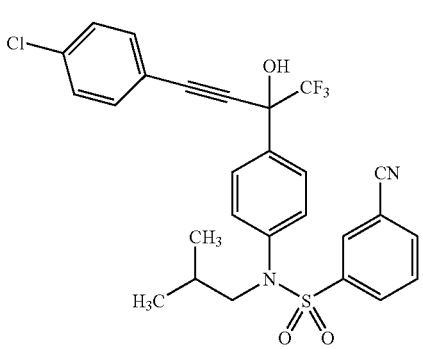

3-Cyano-N-{4-[3-(4-chloro-phenyl)-1-hydroxy-1-trifluoromethyl-prop-2-ynyl]-phenyl}-N-isobutyl-benzenesulfonamide $^1$H NMR (400 MHz, CDCl$_3$) δ 0.931 (m, 6 H), 1.619 (m, 1 H), 3.347 (br s, 1 H), 3.357 (m, 2 H), 7.109 (d, J=8.7 Hz, 2 H), 7.342-7.865 (m, 10 H). Mass Spectrum (CI+) m/e=547 (M+1).

Example 46

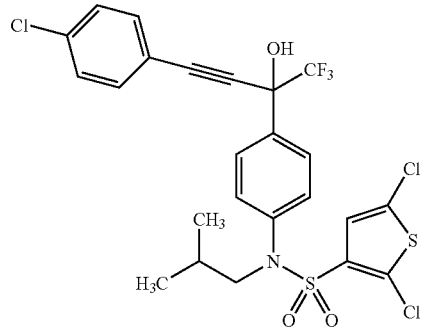

2,5-Dichlorothiophene-3-sulfonic acid {4-[3-(4-chloro-phenyl)-1-hydroxy-1-trifluoromethyl-prop-2-ynyl]-phenyl}-isobutyl-amide $^1$H NMR (CDCl$_3$) δ 0.94 (m, 6 H), 1.65 (m, 1 H), 3.15 (s, 1 H), 3.52 (m 2 H), 6.84 (s, 1 H), 7.20-7.47 (m, 6 H), 7.78 (d, J=8.4 Hz, 2 H). Mass Spectrum (CI+) m/e=598 (M+23).

Example 47

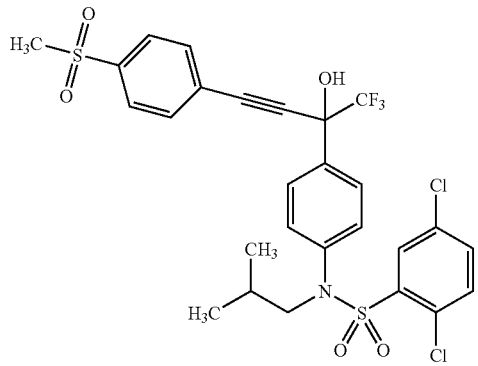

2,5-Dichloro-N-{4-[1-hydroxy-3-(4-methanesulfonyl-phenyl)-1-trifluoromethyl-prop-2-ynyl]-phenyl}-N-isobutyl-benzenesulfonamide Step A. 1-Ethynyl-4-methanesulfonyl-benzene 2-Methyl-3-butyn-2-ol was coupled to 1-bromo-4-methanesulfonyl-benzene according to the procedure described by Bleicher et al. (1995) *Synlett* 1115-1116. The product was converted to 1-ethynyl-4-methanesulfonyl-benzene according to the procedure described by Havens et al. (1985) *J. Org. Chem.* 50:1763-1765.

$^1$H NMR (CDCl$_3$) δ 3.06 (s, 3 H), 3.29 (s, 1 H), 7.67 (d, J=8.1 Hz, 2 H), 7.91 (d, J=8.1 Hz, 2 H).

Step B. 1,1,1-Trifluoro-2-(4-isobutylamino-phenyl)-4-(4-methanesulfonyl-phenyl)-but-3-yn-2-ol The title compound was prepared from 1-(4-isobutylamino-phenyl)-2,2,2-trifluoro-ethanone (Example 41, Step A) as described in Example 34, Step B substituting 1-ethynyl-4-methanesulfonyl-benzene for phenylacetylene.

$^1$H NMR (CDCl$_3$) δ 0.99 (d, J=6.6 Hz, 6 H), 1.90 (m, 1 H), 2.96 (m, 2 H), 3.01 (s, 1 H), 3.07 (s, 3 H), 3.94 (br s, 1 H), 6.62 (d, J=8.7 Hz, 2 H), 7.54 (d, J=8.7 Hz, 2 H), 7.71 (d, J=8.4 Hz, 2 H), 7.94 (d, J=8.4 Hz, 2 H). Mass Spectrum (CI+) m/e=426 (M+1).

Step C. 2,5-Dichloro-N-{4-[1-hydroxy-3-(4-methanesulfonyl-phenyl)-1-trifluoromethyl-prop-2-ynyl]-phenyl}-N-isobutyl-benzenesulfonamide The title compound was prepared as described in Example 34, Step C.

$^1$H NMR (CDCl$_3$) δ 0.95 (m, 6 H), 1.66 (m, 1 H), 3.06 (s, 3 H), 3.55 (br s, 1 H), 3.67 (m, 2 H), 7.32 (d, J=8.7 Hz, 2 H), 7.37-7.42 (m, 2 H), 7.66-7.72 (m, 4 H), 7.80 (d, J=2.2 Hz, 1 H), 7.93 (d, J=8.7 Hz, 2 H). Mass Spectrum (CI+) m/e=652 (M+18).

Example 48 and 49 were prepared from 1,1,1-trifluoro-2-(4-isobutylamino-phenyl)-4-(4-methanesulfonyl-phenyl)-but-3-yn-2-ol and an appropriate sulfonyl chloride using methods as described in Example 34, Step C.

Example 48

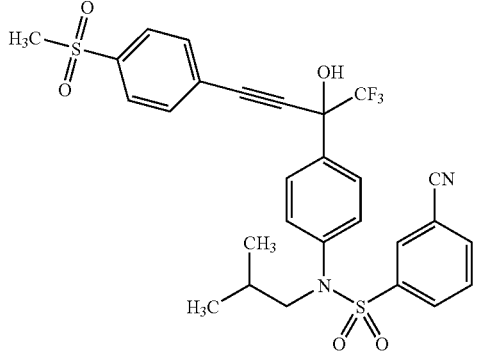

3-Cyano-N-{4-[1-hydroxy-3-(4-methanesulfonyl-phenyl)-1-trifluoromethyl-prop-2-ynyl]-phenyl}-N-isobutyl-benzenesulfonamide $^1$H NMR (CDCl$_3$) δ 0.93 (m, 6 H), 1.62 (m, 1 H), 3.07 (s, 3 H), 3.36 (m, 2 H), 3.45 (s, 1 H), 7.13 (d, J=8.6 Hz, 2 H), 7.59-7.86 (m, 8 H), 7.95 (d, J=8.6 Hz, 2 H). Mass Spectrum (CI+) m/e=613 (M+23).

Example 49

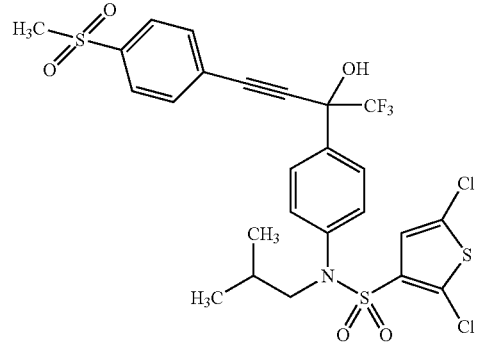

2,5-Dichlorothiophene-3-sulfonic acid {4-[1-hydroxy-3-(4-methanesulfonyl-phenyl)-1-trifluoromethyl-prop-2-ynyl]-phenyl}-isobutyl-amide $^1$H NMR (CDCl$_3$) δ 0.93 (m, 6 H), 1.64 (m, 1 H), 3.06 (s, 3 H), 3.51 (m, 2 H), 4.80 (br s, 1 H), 6.84 (s, 1 H), 7.28 (d, J=8.7 Hz, 2 H), 7.65 (d, J=8.5 Hz, 2 H), 7.79 (d, J=8.5 Hz, 2 H), 7.93 (d, J=8.7 Hz, 2 H). Mass Spectrum (CI+) m/e=640 (M+1).

Example 50

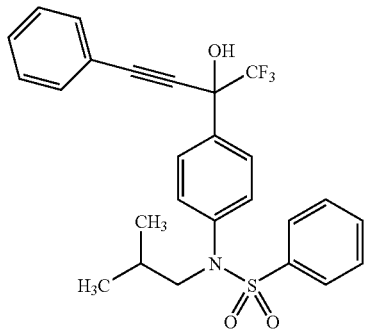

N-[4-(1-Hydroxy-3-phenyl-1-trifluoromethyl-prop-2-ynyl)-phenyl]-N-isobutyl-benzenesulfonamide Step A. N-Isobutyl-benzenesulfonamide To a solution of 4.14 g of isobutylamine (56.6 mmol) and 2.86 g of triethylamine (28.3 mmol) in 40 mL of CH$_2$Cl$_2$ was slowly added 5.0 g of benzenesulfonyl chloride (28.3 mmol) at 0° C. The resulting mixture was stirred at 0° C. for 30 min and then at rt for 1 hr. 150 mL of CH$_2$Cl$_2$ were added, and the organic layer was washed with saturated aqueous solution of NH$_4$Cl and brine (30×2 mL), dried over MgSO$_4$, filtered, and the filtrate was concentrated to give the title compound. ¹H NMR (CDCl₃) δ 0.87 (d, J=6.6 Hz, 6 H), 1.71 (tsept, J=6.7, 6.5 Hz, 1 H), 2.76 (dd, J=6.5, 6.7 Hz, 2 H), 4.61 (t, J=6.5 Hz, 1 H), 7.49-7.88 (m, 5 H). Mass Spectrum (CI+) m/e=214 (M+1).

Step B. N-Isobutyl-N-(4-trifluoroacetyl-phenyl)-benzenesulfonamide

The title compound was prepared from N-Isobutyl-benzenesulfonamide and 1,1,1,4-tetrafluoroacetophenone as described in Example 34, Step A. ¹H NMR (CDCl₃) δ 0.91 (d, J=6.7 Hz, 6 H), 1.60 (tsept, J=7.4, 6.7 Hz, 1 H), 3.38 (d, J=7.4 Hz, 2 H), 7.29 (d, J=8.5 Hz, 2 H), 7.45-7.87 (m, 5 H), 8.03 (d, J=8.5 Hz, 2 H). Mass Spectrum (CI+) m/e=387 (M+1).

Step C. N-[4-(1-Hydroxy-3-phenyl-1-trifluoromethyl-prop-2-ynyl)-phenyl]-N-isobutyl-benzenesulfonamide The title compound was prepared from N-isobutyl-N-(4-trifluoroacetyl-phenyl)-benzenesulfonamide as described in Example 29.

¹H NMR (CDCl₃) δ 0.92 (m, 6 H), 1.59 (m, 1 H), 3.22 (brs. 1 H), 3.33 (m, 2 H), 7.12 (d, J=8.5 Hz, 2 H), 7.35-7.58 (m, 10 H), 7.746 (d, J=8.5 Hz, 2 H). Mass Spectrum (CI+) m/e=487 (M+23).

Examples 51-68 were prepared as described in Example 50, substituting an appropriate acetylene compound for phenylacetylene. The acetylene starting materials are either commercially available or can be synthesized according to methods described herein and referred to below.

Example 51

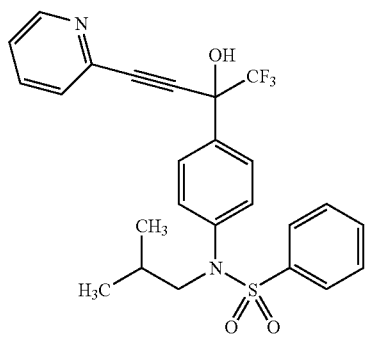

51

N-[4-(1-Hydroxy-2-pyridin-3-yl-1-trifluoromethyl-prop-2-ynyl)-phenyl]-N-isobutyl-benzenesulfonamide ¹H NMR (400 MHz, CDCl₃) δ, 0.91 (m, 6 H), 1.58 (m, 1 H), 3.32 (m, 2 H), 6.03 (br s, 1 H), 7.10 (d, J=8.6 Hz, 2 H), 7.30-7.74 (m, 8 H), 7.77 (d, J=8.6 Hz, 2 H), 8.54 (d, J=4.8 Hz, 1 H). Mass Spectrum (CI+) m/e=489 (M+1).

Example 52

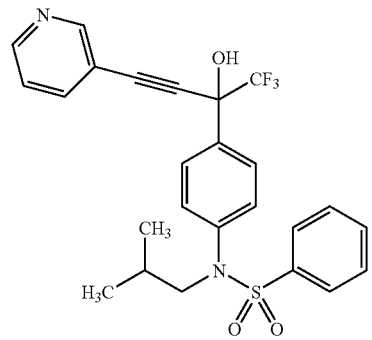

52

N-[4-(1-Hydroxy-3-pyridin-3-yl-1-trifluoromethyl-prop-2-ynyl)-phenyl]-N-isobutyl-benzenesulfonamide ¹H NMR (400 MHz, CDCl₃) δ 0.91 (m, 6 H), 1.59 (m, 1 H), 3.33 (m, 2 H), 7.12 (d, J=8.7 Hz, 2 H), 7.35 (dd, J=8.0, 5.1 Hz, 1 H), 7.42-7.58 (m, 6 H), 7.77 (d, J=8.7 Hz, 2 H), 7.85 (m, 1 H), 8.52 (dd, J=5.1, 2.6, Hz, 1 H), 8.88 (d, J=1.4 Hz, 1 H). Mass Spectrum (CI+) m/e=489 (M+1).

Example 53

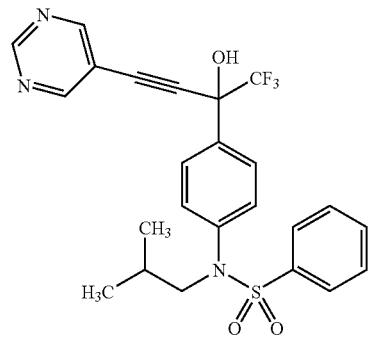

53

N-[4-(1-Hydroxy-3-pyrimidin-5-yl-1-trifluoromethyl-prop-2-ynyl)-phenyl]-N-isobutyl-benzenesulfonamide ¹H NMR (400 MHz, CDCl₃) δ, 0.91 (m, 6 H), 1.58 (m, 1 H), 3.33 (m, 2 H), 5.73 (br s, 1 H), 7.14 (d, J=8.5 Hz, 2 H), 7.43-7.59 (m, 5 H), 7.73 (d, J=8.5 Hz, 2 H), 8.89 (s, 2 H), 9.16 (s, 1 H). Mass Spectrum (CI+) m/e=490 (M+1).

The starting material, 5-ethynyl-pyrimidine was prepared following procedures similar to those described in Example 47, step A. ¹H NMR (CDCl₃) δ 3.41 (s, 1H), 8.81 (s, 2H), 9.16 (s, 1H).

Example 54

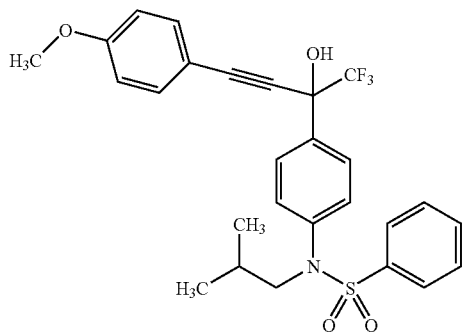

N-[4-(1-Hydroxy-3-(4-methoxy-phenyl)-1-trifluoromethyl-prop-2-ynyl)-phenyl]-N-isobutyl-benzenesulfonamide $^1$H NMR (400 MHz, CDCl$_3$) δ, 0.92 (m, 6 H), 1.58 (m, 1 H), 3.12 (m, 2 H), 3.33 (m, 2 H), 3.84 (s, 3 H), 6.89 (d, J=8.9 Hz, 2 H), 7.11 (d, J=8.7 Hz, 2 H), 7.43-7.57 (m, 7 H), 7.74 (d, J=8.7 Hz, 2 H). Mass Spectrum (CI+) m/e=518 (M+1).

Example 55

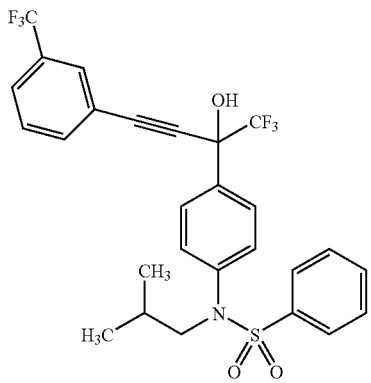

N-[4-(1-Hydroxy-3-(3-trifluoromethyl-phenyl)-1-trifluoromethyl-prop-2-ynyl)-phenyl]-N-isobutyl-benzenesulfonamide $^1$H NMR (400 MHz, CDCl$_3$) δ 0.92 (m, 6 H), 1.59 (m, 1 H), 3.19 (br s, 1 H), 3.33 (m, 2 H), 7.14 (d, J=8.7 Hz, 2 H), 7.34-7.88 (m, 11 H). Mass Spectrum (CI+) m/e=556 (M+1).

The starting material, 1-ethynyl-3-trifluoromethyl-benzene was prepared following procedures similar to those described in Example 47, step A. $^1$H NMR (CDCl$_3$) δ 3.17 (s, 1 H), 7.47 (m, 1 H), 7.61 (m, 1H), 7.67 (m, 1H), 7.77 (s, 1H).

Example 56

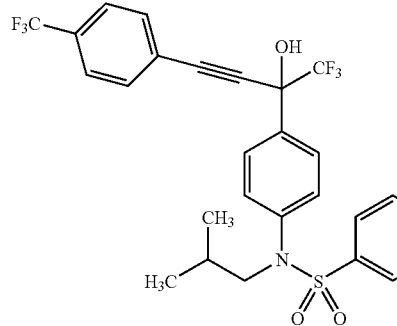

N-[4-(1-Hydroxy-3-(4-trifluoromethyl-phenyl)-1-trifluoromethyl-prop-2-ynyl)-phenyl]-N-isobutyl-benzenesulfonamide $^1$H NMR (400 MHz, CDCl$_3$) δ 0.92 (m, 6 H), 1.59 (m, 1 H), 3.25 (br s, 1 H), 3.33 (m, 2 H), 7.13 (d, J=8.6, 2 H), 7.45-7.57 (m, 5 H), 7.64 (s, 4 H), 7.73 (d, J=8.6 Hz, 2 H). Mass Spectrum (CI+) m/e=578 (M+23).

Example 57

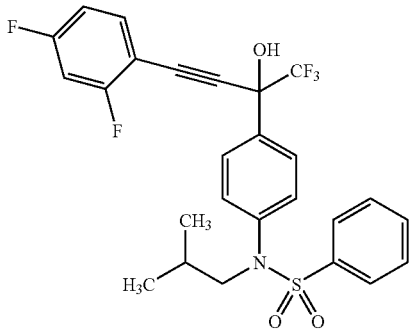

N-[4-(1-Hydroxy-3-(2,4-difluoro-phenyl)-1-trifluoromethyl-prop-2-ynyl)-phenyl]-N-isobutyl-benzenesulfonamide $^1$H NMR (400 MHz, CDCl$_3$) δ 0.91 (m, 6 H), 1.59 (m, 1 H), 3.22 (br s, 1 H), 3.33 (m, 2 H), 6.90 (m, 2 H), 7.12 (d, J=8.0, 2 H), 7.43-7.57 (m, 6 H), 7.73 (d, J=8.0 Hz, 2 H). Mass Spectrum (CI+) m/e=524 (M+23).

Example 58

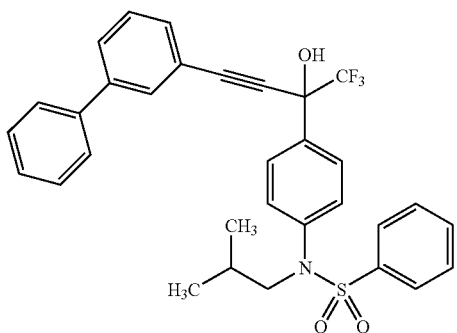

N-[4-(3-Biphenyl-1-1-hydroxy-1-trifluoromethyl-prop-2-ynyl)-phenyl]-N-isobutyl-benzenesulfonamide $^1$H NMR (400 MHz, CDCl$_3$) δ, 0.92 (m, 6 H), 1.60 (m, 1 H), 3.12 (br s, 1 H), 3.33 (m, 2 H), 7.13 (d, J=8.7 Hz, 2 H), 7.39-7.77 (m, 16 H). Mass Spectrum (CI+) m/e=564 (M+1).

The starting material, 3-ethynyl-biphenyl, was prepared following procedures similar to those described in Example 47, step A. $^1$H NMR (CDCl$_3$) δ 3.12 (s, 1 H), 7.36-7.51 (m, 5 H), 7.58-7.62 (m, 3H), 7.75 (m, 1H).

Example 59

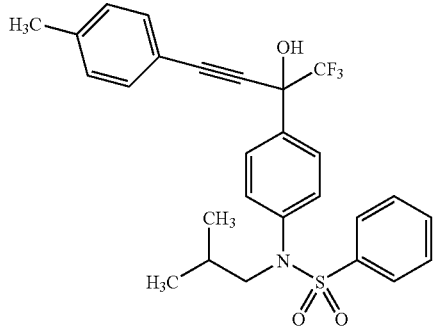

N-[4-(1-Hydroxy-3-(4-tolyl)-1-trifluoromethyl-prop-2-ynyl)-phenyl]-N-isobutyl-benzenesulfonamide $^1$H NMR (400 MHz, CDCl$_3$) δ 0.90 (d, J=6.3 Hz, 6 H), 1.55 (m, 1 H), 2.50 (s, 3 H), 3.26 (br s, 1 H), 3.31 (d, J=7.0 Hz, 2 H), 7.09 (d, J=8.2 Hz, 2 H), 7.41-7.60 (m, 9 H), 7.91 (d, J=8.2 Hz, 2 H). Mass Spectrum (CI+) m/e=566 (M+1).

Example 60

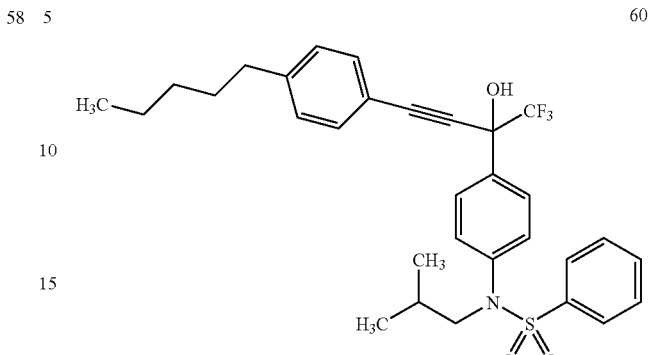

N-[4-(1-Hydroxy-3-(4-pentyl-phenyl)-1-trifluoromethyl-prop-2-ynyl)-phenyl]-N-isobutyl-benzenesulfonamide $^1$H NMR (400 MHz, CDCl$_3$) δ 0.91 (m, 9 H), 1.32 (m, 4 H), 1.61 (m, 3 H), 2.62 (t, J=7.4 Hz, 2 H), 3.26 (s, 1 H), 3.33 (m, 2 H), 7.11 (d, J=8.7 Hz, 2 H), 7.18 (d, J=8.0Hz, 2 H), 7.43-7.57 (m, 7 H), 7.74 (d, J=8.7 HZ, 2 H). Mass Spectrum (CI+) m/e=558 (M+1).

Example 61

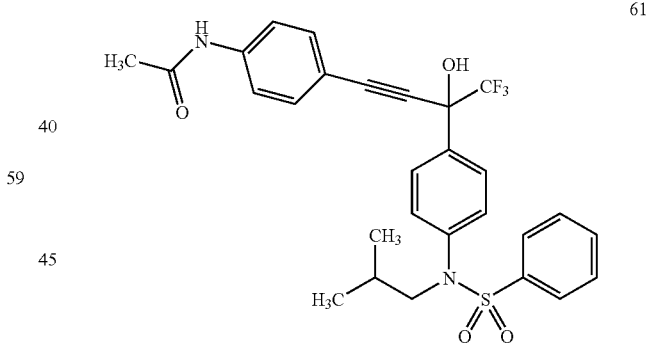

N-[4-(3-(4-Acetamido-phenyl)-1-hydroxy-1-trifluoromethyl-prop-2-ynyl)-phenyl]-N-isobutyl-benzenesulfonamide $^1$H NMR (400 MHz, CDCl$_3$) δ 0.90 (m, 6 H), 1.58 (m, 1 H), 2.16 (s, 3 H), 3.32 (m 2 H), 4.55 (br s, 1 H), 7.10 (d, J=8.7 Hz, 2 H), 7.37-7.58 (m, 9 H), 7.62 (br s, 1 H), 7.74 (d, J=8.7 Hz, 2 H). Mass Spectrum (CI+) m/e=545 (M+1).

The starting material, N-(4-ethynyl-phenyl)-acetamide was prepared as follows:

To a solution of 1 g of 4-ethynyl-aniline (8.5 mmol) and 0.5 mL of pyridine in 5 mL of CH$_2$Cl$_2$ was added 0.95 mL (10.1 mmol) of acetic anhydride. The reaction mixture was stirred for 2 h at rt, quenched by the addition of a saturated aqueous solution of ammonium chloride, and extracted with EtOAc. The combined organic layers were washed with brine, dried over MgSO₄, filtered and the filtrate was concentrated. The residue was purified by chromatography on silica (hexanes:EtOAc, 4:1) to give the title compound.

¹H NMR (CDCl₃) δ 2.18 (s, 3 H), 3.04 (s, 1 H), 7.45-7.49 (m, 5 H).

The starting material, N-(4-ethynyl-phenyl)-methylsulfonamide was prepared in a manner similar to that described in Example 61. ¹H NMR (CDCl₃) δ 3.04 (s, 3 H), 3.41 (s, 1 H), 6.91 (s, 1 H), 7.18 (d, J=8.6 Hz, 2 H), 7.48 9d, J=8.6 Hz, 2 H).

Example 62

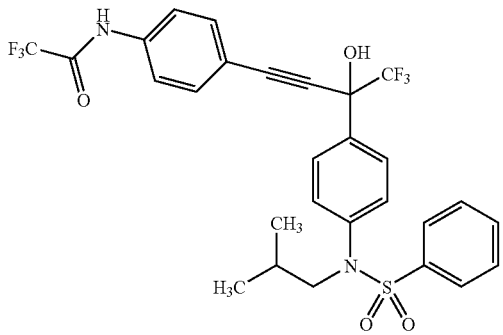

N-[4-(1-Hydroxy-3-(4-trifluoroacetamido-phenyl)-1-trifluoromethyl-prop-2-ynyl)-phenyl]-N-isobutyl-benzenesulfonamide ¹H NMR (400 MHz, CDCl₃) δ 0.91 (m, 6 H), 1.58 (m, 1 H), 3.32 (m, 2 H), 3.39 (br s, 1 H), 7.12 (d, J=8.5 Hz, 2 H), 7.43-7.67 (m, 9 H), 7.77 (d, J=8.5 Hz, 2 H), 8.18 (s, 1 H). Mass Spectrum (CI+) m/e=621 (M+23).

The starting material, N-(4-ethynyl-phenyl)-trifluoroacetamide was prepared in a manner similar to that described in Example 61. ¹H NMR (CDCl₃) δ 3.11 (s, 1 H), 7.50-7.56 (m, 4 H), 8.00 (br s, 1 H).

Example 63

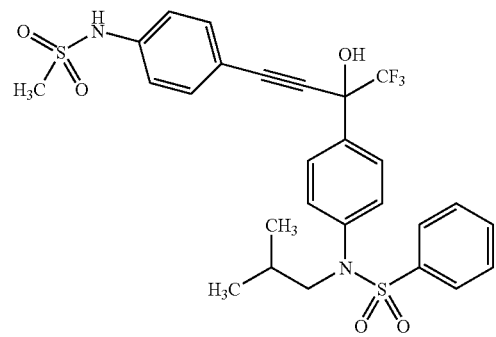

N-[4-(1-Hydroxy-3-(4-methanesulfonamido-phenyl)-1-trifluoromethyl-prop-2-ynyl)-phenyl]-N-isobutyl-benzenesulfonamide ¹H NMR (400 MHz, CDCl₃) δ, 0.91 (m, 6 H), 1.59 (m, 1 H), 2.05 (br s, 1 H), 3.06 (s, 3 H), 3.33 (m, 2 H), 6.79 (s, 1 H), 7.12 (d, J=8.5 Hz, 2 H), 7.21 (d, J=8.4 Hz, 2 H), 7.39-7.59 (m, 7 H), 7.73 (d, J=8.5 Hz, 2 H). Mass Spectrum (CI+) m/e=581 (M+1).

Example 64

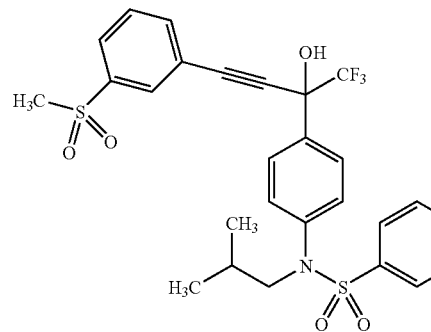

N-[4-(1-Hydroxy-3-(3-methanesulfonyl-phenyl)-1-trifluoromethyl-prop-2-ynyl)-phenyl]-N-isobutyl-benzenesulfonamide ¹H NMR (CDCl₃) δ 0.91 (m, 6 H), 1.58 (m, 1 H), 3.07 (s, 3 H), 3.32 (m, 2 H), 3.78 (s, 1 H), 7.13 (d, J=8.7 Hz, 2 H), 7.45 (m, 2 H), 7.57 (m, 4 H), 7.72 (d, J=8.7 Hz, 2 H), 7.77 (m, 1 H), 7.95 (m, 1 H), 8.07 (m, 1 H). Mass Spectrum (CI+) m/e=566 (M+1).

The starting material, (3-ethynyl-phenyl)methyl sulfone was prepared using methods similar to those described in Example 47, step A. ¹H NMR (CDCl₃) δ 3.05 (s, 3 H), 3.21 (s, 1 H), 7.54 (dd, J=7.8, 7.8 Hz, 1 H), 7.73 (d, J=7.8 Hz, 1 H), 7.91 (d, J=7.8 Hz, 1 H), 8.05 (s, 1 H).

Example 65

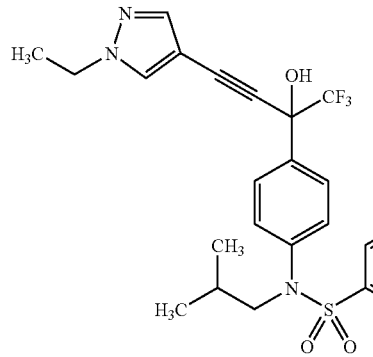

N-{4-[3-(1-Ethyl-1H-pyrazol-4-yl)1-hydroxy-1-trifluoromethyl-prop-2-ynyl]-phenyl}-N-isobutyl-benzenesulfonamide ¹H NMR (CDCl₃) δ, 0.91 (m, 6 H), 1.50 (t, J=7.3 Hz, 3 H), 1.58 (m, 1 H), 3.32(m, 2 H), 3.57 (s, 1 H), 4.18 (q, J=7.3 Hz, 2 H), 7.10 (d, J=8.6 Hz, 2 H), 7.43-7.64 (m, 7 H), 7.72 (d, J=8.6 Hz, 2 H). Mass Spectrum (CI+) m/e=506 (M+1).

Preparation of 1-Ethyl-4-ethynyl-1H-pyrazole

Step A. 1-Ethyl-4-iodo-1H-pyrazole

To a solution of 5 g of 4-iodopyrazole (25.8 mmol) in 20 mL of DMF at 0° C. was added 1.24 g (31 mmol) of NaH (60% dispersion in oil) and the mixture was stirred at 0° C. for 30 min. After this time, 3.1 mL (38.8 mmol) of iodoethane were added and the mixture was allowed to warm to room temperature and stirred for 14 h. After this time the reaction was quenched by the addition of a saturated aqueous solution of ammonium chloride, allowed to warm to room temperature, and extracted with EtOAc. The combined organic layers were washed with brine, dried over MgSO$_4$, filtered and the filtrate was concentrated. The residue was purified by chromatography on silica gel (hexanes:EtOAc, 9:1) to give the title compound.
$^1$H-NMR (CDCl$_3$) δ 1.46 (t, 3H, J=7.4 Hz), 4.2 (q, 2H, J=7.4Hz), 7.43 (s, 1H), 7.49 (s, 1H).

Step B. 1-Ethyl-4-ethynyl-1H-pyrazole

The title compound was prepared following methods similar to those described in Example 47, Step A. $^1$H-NMR (CDCl$_3$) δ 1.46 (t, 3H, J=7.4 Hz), 2.99 (s, 1H), 4.13 (q, 2H, J=7.4 Hz), 7.54 (s, 1H), 7.59 (s, 1H).

Example 66

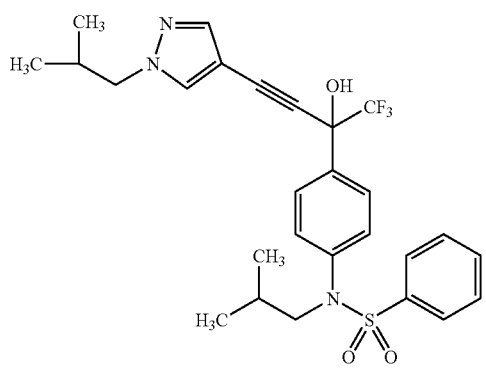

66

N-{4-[3-(1-Isobutyl-1H-pyrazol-4-yl)1-hydroxy-1-trifluoromethyl-prop-2-ynyl]-phenyl}-N-isobutyl-benzenesulfonamide The title compound was prepared following methods described in Example 65. Preparation of starting materials is provided below. $^1$H NMR (CDCl$_3$) δ 0.91 (m, 12 H),1.58 (m, 1 H), 2.21 (m, 1 H), 3.32 (m, 2 H), 3.71 (s, 1 H), 3.90 (d, J=7.2 Hz, 2 H), 7.10 (d, J=8.6 Hz, 2 H), 7.43-7.58 (m, 6 H), 7.64 (s, 1 H), 7.72 (d, J=8.6 Hz, 2 H). Mass Spectrum (CI+) m/e=534 (M+1).

Preparation of 1-Isobutyl-4-ethynyl-1H-pyrazole

Step A. 1-Isobutyl-4-iodo-1H-pyrazole

The title compound was prepared using methods similar to those described in Example 65. $^1$H-NMR (CDCl$_3$) δ 0.89 (d, 6H, J=6.8 Hz), 2.17 (m, 1H), 3.91 (d, 2H, J=6.8 Hz), 7.39 (s, 1H), 7.50 (s, 1H).

Step B. 1-Isobutyl-4-ethynyl-1H-pyrazole

The title compound was prepared using methods similar to those described in Example 65. $^1$H-NMR (CDCl$_3$) δ 0.90 (d, 6H, J=7.2 Hz), 2.19 (m, 1H), 3.01 (s, 1H), 3.88 (d, 2H, J=7.2 Hz), 7.51 (s, 1H), 7.61 (s, 1H).

Example 67

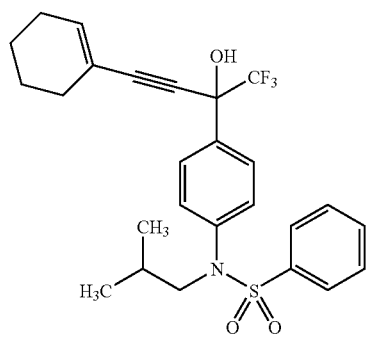

67

N-[4-(3-Cyclohex-1-enyl-1-hydroxy-1-trifluoromethyl-prop-2-ynyl)-phenyl]-N-isobutyl-benzenesulfonamide $^1$H NMR (400 MHz, CDCl$_3$) δ 0.90 (m, 6 H), 1.63 (m, 5 H), 2.14 (m, 4 H), 3.22 (s, 1 H), 3.31 (m, 2 H), 6.28 (m, 1 H), 7.08 (d, J=8.7 Hz, 2 H), 7.42-7.58 (m, 5 H), 7.67 (d, J=8.7 Hz, 2 H). Mass Spectrum (CI+) m/e=492 (M+1).

Example 68

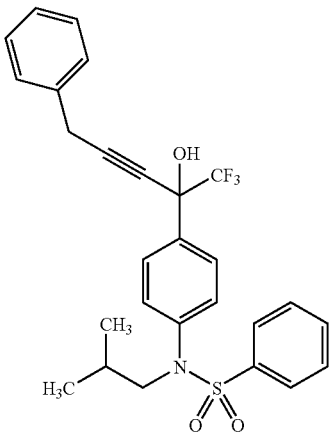

68

N-[4-(1-Hydroxy-4-phenyl-1-trifluoromethyl-but-2-ynyl)-phenyl]-N-isobutyl-benzenesulfonamide $^1$H NMR (400 MHz, CDCl$_3$) δ 0.91 (m, 6 H), 1.58 (m, 1 H), 3.32 (m, 2 H), 3.76 (s, 2 H), 7.08 (d, J=8.7 Hz, 2 H), 7.27-7.58 (m, 10 H), 7.68 (d, J=8.7 Hz, 2 H). Mass Spectrum (CI+) m/e=502 (M+1).

Example 69

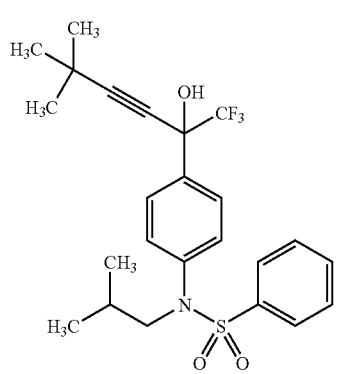

N-[4-(1-Hydroxy-4,4-dimethyl-1-trifluoromethyl-pent-2-ynyl)-phenyl]-N-isobutyl-benzenesulfonamide $^1$H NMR (400 MHz, CDCl$_3$) δ 0.91 (m, 6 H), 1.30 (s, 9 H), 1.58 (m, 1 H), 2.84 (br s, 1 H), 3.32 (m, 2 H), 6.90 (m, 2 H), 7.08 (d, J=8.4, 2 H), 7.43-7.58 (m, 5 H), 7.65 (d, J=8.4 Hz, 2 H). Mass Spectrum (CI+) m/e=490 (M+23).

Example 70

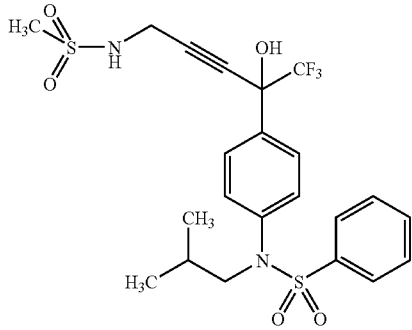

N-[4-(1-Hydroxy-4-methanesulfonylamino-1-trifluoromethyl-but-2-ynyl)-phenyl]-N-isobutyl-benzenesulfonamide $^1$H NMR (400 MHz, CDCl$_3$) δ, 0.89 (m, 6 H), 1.55 (m, 1 H), 3.04 (s, 3 H), 3.32 (m, 2 H), 4.05 (m, 2 H), 4.37 (br s, 1 H), 5.26 (br s, 1 H), 7.09 (d, J=8.7 Hz, 2 H), 7.44-7.60 (m, 5 H), 7.64 (d, J=8.7 Hz, 2 H). Mass Spectrum (CI+) m/e=519 (M+1).

Example 71

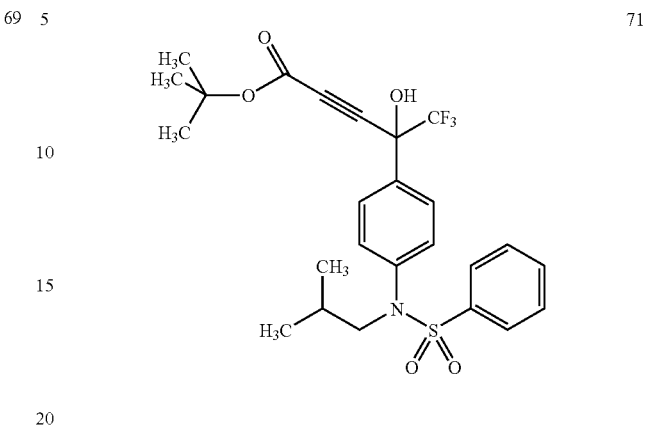

4-[4-(Benzenesulfonyl-isobutyl-amino)-phenyl]-5,5,5-trifluoro-4-hydroxy-pent-2-ynoic acid tert-butyl ester $^1$H NMR (400 MHz, CDCl$_3$) δ 0.90 (m, 6 H), 1.52 (s, 9 H), 1.54 (m, 1 H), 3.31 (m, 2 H), 3.81 (d, J=4.7 Hz, 1 H), 7.11 (d, J=8.6 Hz, 2 H), 7.43-7.59 (m, 5 H), 7.65 (d, J=8.6 Hz, 2 H). Mass Spectrum (CI+) m/e=534 (M+23).

Example 72

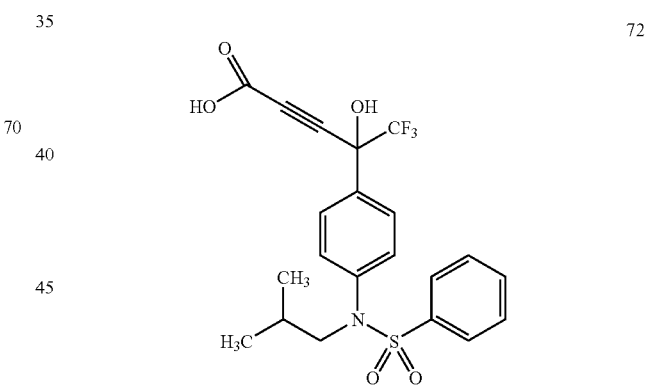

4-[4-(Benzenesulfonyl-isobutyl-amino)-phenyl]-5,5,5-trifluoro-4-hydroxy-pent-2-ynoic acid To a solution of 0.56 g (1.1 mmol) of 4-[4-(benzenesulfonyl-isobutyl-amino)-phenyl]-5,5,5-trifluoro-4-hydroxy-pent-2-ynoic acid tert-butyl ester (Example 71) in 15 mL of CH$_2$Cl$_2$ was added 0.3 mL of trifluoroacetic acid. The mixture was stirred at room temperature for 24 h. After this time the solvent was evaporated, and the residue was purified by chromatography (silica, hexanes:EtOAc, 1:1) to give the title compound.

$^1$H NMR (400 MHz, DMSO) δ 0.84 (d, J=6.6 Hz, 6 H), 1.41 (m, 1 H), 3.36 (d, J=7.3 Hz, 2 H), 7.23 (d, J=8.1 Hz, 2 H), 7.54-7.72 (m, 7 H), 8.36 (s, 1 H). Mass Spectrum (CI+) m/e=410 (M−45).

Example 73

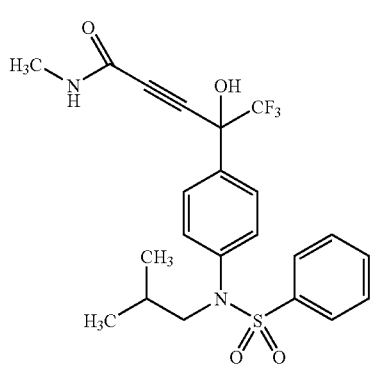

4-[4-(Benzenesulfonyl-isobutyl-amino)-phenyl]-5,5,5-trifluoro-4-hydroxy-pent-2-ynoic acid methylamide 0.2 g of 4-[4-(benzenesulfonyl-isobutyl-amino)-phenyl]-5,5,5-trifluoro-4-hydroxy-pent-2-ynoic acid (see Example 69; 0.439 mmol) and 0.26 mL of methylamine (2M in THF) were combined in 3 mL of $CH_2Cl_2$ at rt. 0.1 g of 1-[3-(dimethylamino)propyl]-3-ethylcarbodiimide hydrochloride (0.527 mmol) was added. The resulting mixture was stirred at rt for 16 h. After addition of 80 mL of $CH_2Cl_2$ the resulting solution was washed with an aqueous solution of citric acid, a saturated aqueous solution of sodium bicarbonate and brine. The organic layers were dried over $MgSO_4$, filtered and the filtrate was concentrated. The residue was purified by chromatography on silica(EtOAc:hexanes, 1:1) to give the title compound. $^1$H NMR (400 MHz, CDCl$_3$) δ 0.90 (m, 6 H), 1.56 (m, 1 H), 2.91 (d, J=5.0 Hz, 3 H), 3.31 (m, 2 H), 3.72 (br s, 1 H), 6.26 (d, 5.0 Hz, 1 H), 7.11 (d, J=8.7 Hz, 2 H), 7.44-7.60 (m, 5 H), 7.64 (d, J=8.7 Hz, 2 H). Mass Spectrum (CI+) m/e=486 (M+18).

Example 74

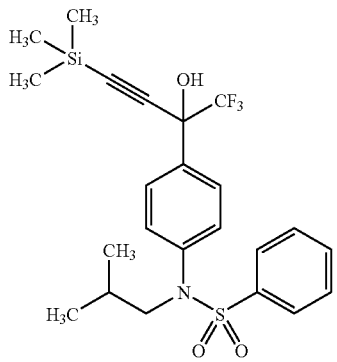

N-[4-(1-Hydroxy-1-trifluoromethyl-3-trimethylsilanyl-prop-2-ynyl)-phenyl]-N-isobutyl-benzenesulfonamide $^1$H NMR (CDCl$_3$) δ 0.25 (s, 9 H), 0.91 (m, 6 H), 1.58 (m, 1 H), 3.06 (s, 1 H), 3.32(m, 2 H), 7.09 (d, J=8.6 Hz, 2 H), 7.42-7.56 (m, 5 H), 7.65 (d, J=8.6 Hz, 2 H). Mass Spectrum (CI+) m/e=506 (M+23).

Example 75

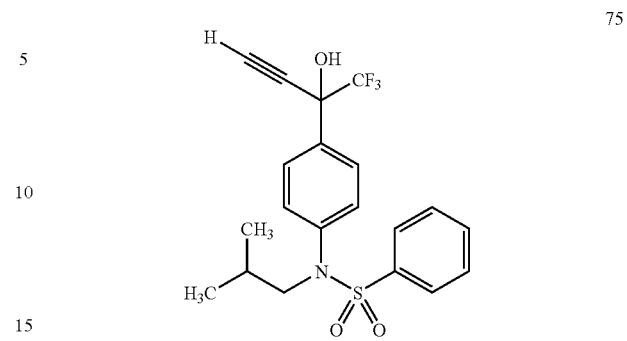

N-[4-(1-Hydroxy-1-trifluoromethyl-prop-2-ynyl)-phenyl]-N-isobutyl-benzenesulfonamide To a solution of 0.25 g (0.51 mmol) of N-[4-(1-hydroxy-1-trifluoromethyl-3-trimethylsilanyl-prop-2-ynyl)-phenyl]-N-isobutyl-benzenesulfonamide (Example 74) in 6 mL of $CH_2Cl_2$ was added 0.4 mL of a 1 M solution of tetrabutylammonium fluoride in THF. The mixture was stirred at room temperature for 1 hour. $CH_2Cl_2$ (60 mL) was added and the solution was washed with saturated aqueous NH$_4$Cl-solution (20 mL) and brine (15 mL). The organic layer was dried over Na$_2$SO$_4$, filtered and the filtrate was concentrated. The residue was purified by chromatography on silica gel, (hexane:EtOAc, 7:3) to give the title compound.
$^1$H NMR (CDCl$_3$) δ 0.91 (d, J=6.6 Hz, 6 H), 1.58 (m, 1 H), 2.84 (s, 1 H), 3.10 (s, 1 H), 3.32 (d, J=7.4 Hz, 2 H), 7.11 (d, J=8.5 Hz, 2 H), 7.43-7.57 (m, 5 H), 7.68 (d, J=8.5 Hz, 2 H). Mass Spectrum (CI+) m/e=434 (M+23).

Example 76

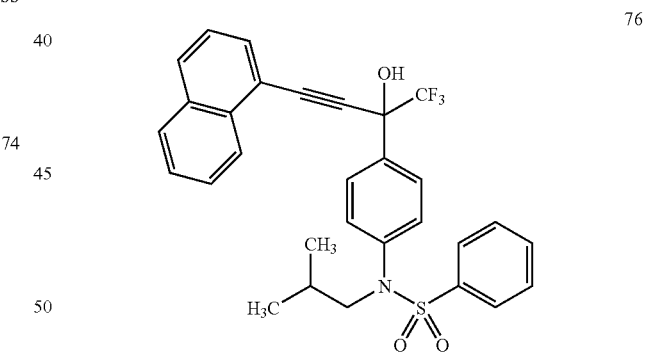

N-[4-(1-Hydroxy-3-naphthalen-1-yl-1-trifluoromethyl-prop-2-ynyl)-phenyl]-N-isobutyl-benzenesulfonamide 80.6 mg (0.39 mmol) 2-Bromonaphthalene, 21 mg palladium on carbon (10% Pd), 74.-1 mg (0.39 mmol) copper (I) iodide, and 135 mg (0.98 mmol) K$_2$CO$_3$ were combined 2 mL of DME and 2 mL of water and the resulting mixture was stirred at room temperature for 30 min. A solution of 80 mg (0.2 mmol) of N-[4-(1-hydroxy-1-trifluoromethyl-prop-2-ynyl)-phenyl]-N-isobutyl-benzenesulfonamide (Example 75) in 1 mL of DME was added and the reaction mixture was stirred at 65° C. overnight. The catalyst was removed by filtration over a pad of celite. The filtrate was washed with a saturated aqueous solution of ammonium chloride and brine. The organic layers were dried over Na$_2$SO$_4$, filtered and the filtrate was concentrated. The residue was purified by chromatography on silica gel (hexanes:EtOAc=9:1) to give the title compound.

$^1$H NMR (CDCl$_3$) δ 0.92 (m, 6 H), 1.60 (m, 1 H), 3.22 (s, 1 H), 3.34 (m, 2 H), 7.14 (d, J=8.5 Hz, 2 H), 7.44-7.59 (m, 8 H), 7.78 (d, J=8.5 Hz, 2 H), 7.83-7.86 (m, 3 H), 8.08 (s, 1 H). Mass Spectrum (CI+) m/e=538 (M+1).

Example 77

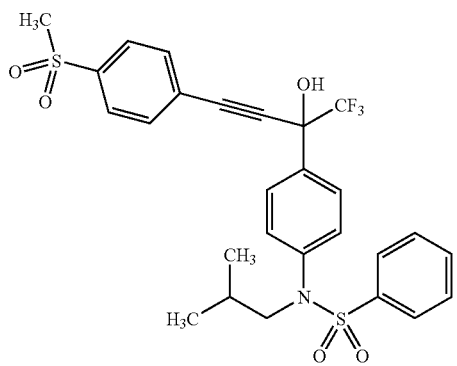

N-[4-(1-Hydroxy-3-(4-methanesulfonyl-phenyl)-1-trifluoromethyl-prop-2-ynyl)-phenyl]-N-isobutyl-benzenesulfonamide The title compound was prepared using methods as described in Example 76.

$^1$H NMR (CDCl$_3$) δ 0.91 (m, 6 H), 1.59 (m, 1 H), 3.07 (s, 3 H), 3.33 (m, 2 H), 3.49 (s, 1 H), 7.14 (d, J=8.7 Hz, 2 H), 7.43-7.73 (m, 9 H), 7.94 (d, J=8.7 Hz, 2 H). Mass Spectrum (CI+) m/e=588 (M+23).

Example 78

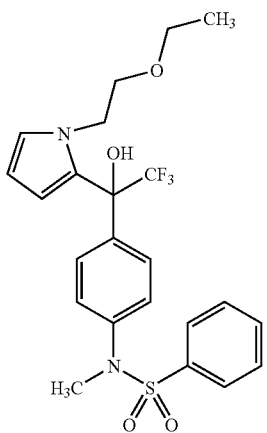

N-(4-{1-[1-(2-Ethoxyethyl)-1H-pyrrol-2-yl]-2,2,2-trifluoro-1-hydroxyethyl}-phenyl)-N-methyl-benzenesulfonamide Step A. N-Ethoxyethyl-2-trifluoroacetylpyrrole To a suspension of 268 mg (6.70 mmol) of NaH (60% dispersion in oil) in 20 mL DMF at 0° C. was added 1.01 g (6.19 mmol) of 2-(trifluoroacteyl)pyrrole and the mixture was stirred at 0° C. for 1 h. After this time, 765 μL (6.51 mmol) of 2-bromoethyl ethyl ether was added and the mixture was warmed to 60° C. and stirred for 16 h. After this time, the reaction mixture was allowed to cool to room temperature, quenched by the addition of a saturated aqueous solution of ammonium chloride, and extracted with EtOAc. The organic layer was washed with water and brine, dried over Na$_2$SO$_4$, filtered and the filtrate was concentrated. The residue was purified by chromatography on silica gel (pure hexanes grading to hexanes:EtOAc, 97:3) to give the title compound.

$^1$H-NMR (CDCl$_3$) δ 7.19 (s, 1H), 6.25-6.30 (m, 1H), 4.52 (t, J=5.1 Hz, 1H), 3.69 (t, J=5.4 Hz, 2H), 3.42 (q, J=7.0 Hz, 2H), 1.13 (t, J=7.0 Hz, 3H). Mass Spectrum (ESI) m/e=190 (M−45).

Step B. 4-Bromo-N-methylaniline

The title compound was prepared in a manner similar to that described in Example 1, Step A. $^1$H-NMR (DMSO) δ 2.64 (s, 3H), 5.82 (brs, 1H), 6.46-6.49 (m, 2H), 7.18-7.21 (m, 2H).

Step C. N-(4-Bromophenyl)-N-methyl-benzenesulfonamide

A solution of 0.61 g (3.3 mmol) of 4-bromo-N-methylaniline and 0.5 mL (3.92 mmol) of benzenesulfonyl chloride in 5 mL of pyridine was stirred for 12 h at rt. After that time the pyridine was removed by azeotropic distillation with heptane. The residue was purified by chromatography on silica (hexanes:EtOAc, 9:1) to give the title compound.

$^1$H NMR (DMSO) δ 3.12 (s, 3 H), 7.04-7.08 (m, 2 H), 7.50-7.62 (m, 6 H), 7.69-7.74 (m, 1 H).

Step D. N-(4-{1-[1-(2-Ethoxyethyl)-1H-pyrrol-2-yl]-2,2,2-trifluoro-1-hydroxyethyl}-phenyl)-N-methyl-benzenesulfonamide To a solution of 75 mg (0.23 mmol) of N-(4-bromophenyl)-N-methyl-benzenesulfonamide in 4 mL of Et$_2$O at −78° C. was added dropwise 285 μL (0.49 mmol) of a 1.7 M solution of tert-BuLi in pentane and the resultant mixture was stirred at −78° C. for 10 min. To this mixture was then added a solution of 81 mg (0.34 mmol) of N-ethoxyethyl-2-trifluoroacetylpyrrole in 3 mL THF and the mixture was allowed to gradually warm to room temperature over an 18 h period. The reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (hexanes:EtOAc, 4:1) to give the title compound.

$^1$H-NMR (CDCl$_3$) δ 7.49-7.60 (m, 3H), 7.42 (t, J=7.4 Hz, 2H), 7.32 (d, J=8.5 Hz, 2H), 7.06 (d, J=8.7 Hz, 2H), 6.67 (dd, J=2.7 Hz, 1.7 Hz, 1H), 6.45-6.50 (m, 1H), 6.20 (t, J=3.3 Hz, 1H), 5.82 (s, 1H), 3.76-3.85 (m, 1H), 3.55-3.65 (m, 2H), 3.43-3.52 (m, 2H), 3.29-3.38 (m, 1H), 3.17 (s, 3H), 1.15 (t, J=7.0 Hz, 3H). Mass Spectrum (ESI) m/e=505.1 (M+23).

The following examples were prepared from N-(4-bromophenyl)-N-methyl-benzenesulfonamide as described in Example 78. The required ketones are prepared as described in Example 78, Step A, or alternative procedures will described.

Example 79

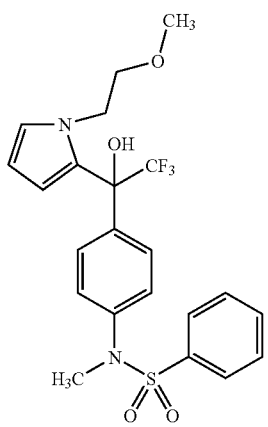

N-(4-{1-[1-(2-Methoxyethyl)-1H-pyrrol-2-yl]-2,2,2-trifluoro-1-hydroxyethyl}-phenyl)-N-methyl-benzenesulfonamide $^1$H-NMR (CDCl$_3$) δ 3.16 (s, 3H), 3.26 (s, 3H), 3.42-3.62 (m, 4H), 6.18 (m, 1H), 6.46 (m, 1H), 6.69 (m, 1H), 7.04-7.56 (m, 9H). Mass Spectrum (CI+) m/e=491.1 (M+1).

The starting material, N-methoxyethyl-2-trifluoroacetylpyrrole, was prepared in a manner similar to that described in Example 78, Step A.

$^1$H-NMR (CDCl$_3$) δ 1.25 (s, 3H), 3.64 (t, J=5.1 Hz, 2H), 4.52 (t, J=5.0 Hz, 2H), 6.25 (m, 1H), 7.17 (m, 1H), 7.25 (m, 1H). Mass Spectrum (CI+) m/e=mass ion not observed.

Example 80

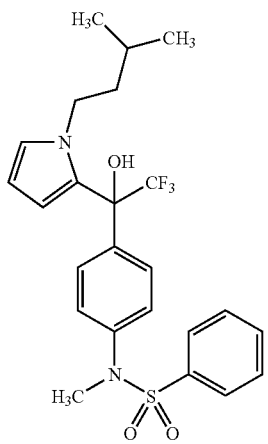

N-(4-{1-[1-(3-methylbutyl)-1H-pyrrol-2-yl]-2,2,2-trifluoro-1-hydroxyethyl}-phenyl)-N-methyl-benzenesulfonamide Mass Spectrum (CI+) m/e=481.1 (M+1).

The starting material, N-(3-methylbutyl)-2-trifluoroacetylpyrrole, was prepared using methods similar to those described in Example 78, Step A.

$^1$H-NMR (CDCl$_3$) δ 0.94-0.98 (m, 6 H), 1.64 (m, 3 H), 4.35 (m, 2 H), 6.27 (m, 1 H), 7.10 (m, 1 H), 7.24 (m, 1 H).

Example 81

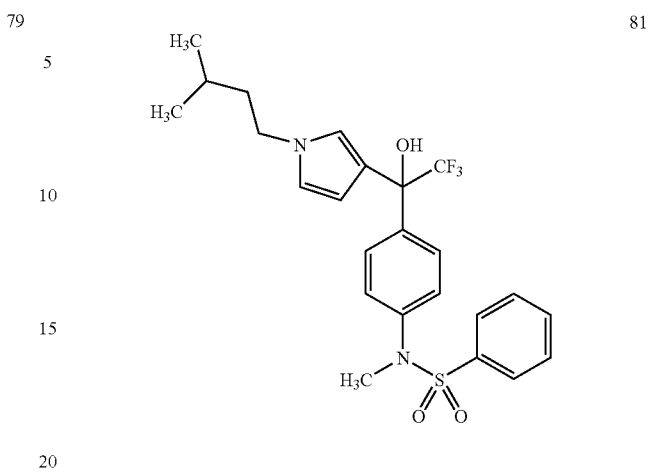

N-(4-{1-[1-(3-Methylbutyl)-1H-pyrrol-3-yl]-2,2,2-trifluoro-1-hydroxyethyl}-phenyl)-N-methyl-benzenesulfonamide $^1$H-NMR (CDCl$_3$) δ 0.96 (d, J=6.5 Hz, 6H), 1.57-1.71 (m, 3H), 2.78 (brs, 1H), 3.20 (s, 3H), 3.87 (m, 2H), 6.09 (m, 1H), 6.63(m, 1 H), 6.70 (m, 1H), 7.10 (m, 2H), 7.44-7.61 (m, 7H). Mass Spectrum (CI+) m/e=503.1 (M+23).

The starting material, N-(3-methylbutyl)-3-trifluoroacetylpyrrole was prepared using methods as described in Example 78, Step A.

$^1$H-NMR (CDCl$_3$) δ 0.98 (d, J=6.6 Hz, 6H), 1.58-1.62 (m, 1H), 1.70-1.76 (m, 2H), 3.97 (m, 2H), 6.70 (m, 1H), 6.76 (m, 1H), 7.50 (m, 1H). Mass Spectrum (CI+) m/e=234.1 (M+1).

Example 82

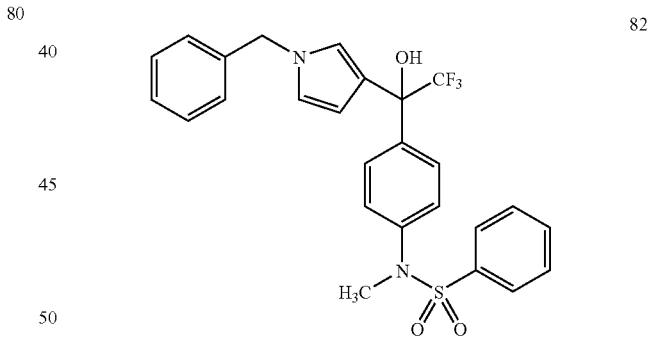

N-(4-{1-[1-Benzyl-1H-pyrrol-3-yl]-2,2,2-trifluoro-1-hydroxyethyl}-phenyl)-N-methyl-benzenesulfonamide $^1$H-NMR (CDCl$_3$) δ 2.86 (brs, 1H), 3.20 (s, 3H), 5.06 (s, 2H), 6.17 (m, 1H), 6.68 (m, 1H), 6.78 (m, 1H), 7.10-7.16 (m, 4H), 7.34-7.56 (m, 10H). Mass Spectrum (CI+) m/e=523.1 (M+23).

The starting material, N-benzyl-3-trifluoroacetylpyrrole was prepared using methods similar to those described in Example 78, Step A.

$^1$H-NMR (CDCl$_3$) δ 5.14 (s, 2H), 6.72-6.80 (m, 2H), 7.19-7.21 (m, 2H), 7.37-7.43 (m, 3H), 7.56 (m, 1H). Mass Spectrum (CI+) m/e=254.1 (M+1).

Example 83

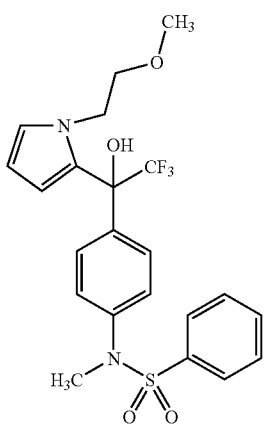

N-(4-{1-Hydroxy-1-[1-(2-methoxyethyl)-1H-pyrrol-2-yl]-ethyl}-phenyl)-N-methyl-benzenesulfonamide $^1$H-NMR (CDCl$_3$) δ 6.99 (dd, J=4.0 Hz, 1.7 Hz, 1H), 6.93 (t, J=2.0 Hz, 1H), 6.12 (dd, J=4.0 Hz, 2.6 Hz, 1H), 4.50 (t, J=5.2 Hz, 2H), 3.65 (t, J=5.2 Hz, 2H), 3.28 (s, 3H), 2.42 (s, 3H). Mass Spectrum (ESI) m/e=136.1 (M−31).

The starting material, N-methoxyethyl-2-acetylpyrrole, was prepared using methods similar to those described in Example 78, Step A.

$^1$H-NMR (CDCl$_3$) δ 6.99 (dd, J=4.0 Hz, 1.7 Hz, 1H), 6.93 (t, J=2.0 Hz, 1H), 6.12 (dd, J=4.0 Hz, 2.6 Hz, 1H), 4.50 (t, J=5.2 Hz, 2H), 3.65 (t, J=5.2 Hz, 2H), 3.28 (s, 3H), 2.42 (s, 3H). Mass Spectrum (ESI) m/e=136.1 (M−31).

Example 84

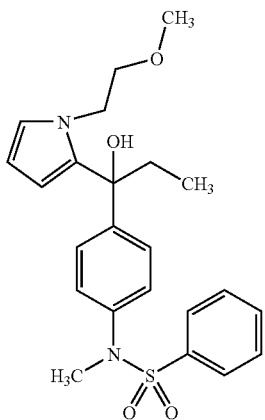

N-(4-{1-Hydroxy-1-[1-(2-methoxyethyl)-1H-pyrrol-2-yl]-propyl)-phenyl}-N-methyl-benzenesulfonamide $^1$H-NMR (CDCl$_3$) δ 7.48-7.59 (m, 3H), 7.41 (t, J=7.5 Hz, 2H), 7.19 (d, J=8.6 Hz, 2H), 6.99 (d, J=8.6 Hz, 2H), 6.62 (dd, J=2.7 Hz, 1.9 Hz, 1H), 6.30 (dd, J=3.6 Hz, 1.8 Hz, 1H), 6.15 (t, J=3.2 Hz, 1H), 3.94 (s, 1H), 3.77-3.86 (m, 1H), 3.59-3.67 (m, 1H), 3.33-3.45 (m, 2H), 3.27 (s, 3H), 3.16 (s, 3H), 2.21-2.31 (m, 1H), 2.01-2.11 (m, 1H), 0.80 (t, J=7.4 Hz, 3H). Mass Spectrum (ESI) m/e=451.1 (M+23).

The starting material, N-methoxyethyl-2-propionylpyrrole was prepared as follows:

To a solution of 102 mg (0.61 mmol) of N-methoxyethyl-2-acetylpyrrole in 4.5 mL THF at −78° C. was added dropwise 670 μL (0.67 mmol) of a 1.0 M solution of LHMDS in THF and the resultant mixture was stirred for 30 min. After this time, 57 L (0.92 mmol) of MeI was added dropwise and the mixture was stirred at −78° C. for 1.5 h, then was warmed to 0° C. and stirred for an additional 45 min. After this time, the reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (pure hexanes grading to hexanes:EtOAc, 88:12) to give the title compound.

$^1$H-NMR (CDCl$_3$) δ 7.00 (dd, J=4.0 Hz, 1.7 Hz, 1H), 6.92 (t, J=2.1 Hz, 1H), 6.13 (dd, J=4.1 Hz, 2.5 Hz, 1H), 4.50 (t, J=5.1 Hz, 2H), 3.65 (t, J=5.2 Hz, 2H), 3.29 (s, 3H), 2.81 (q, J=7.4 Hz, 2H), 1.17 (t, J=7.4 Hz, 3H). Mass Spectrum (ESI) m/e=150.1 (M−31).

Example 85

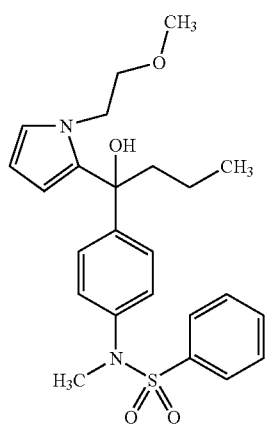

N-(4-{1-Hydroxy-1-[1-(2-methoxyethyl)-1H-pyrrol-2-yl]-butyl}-phenyl)-N-methyl-benzenesulfonamide $^1$H-NMR (CDCl$_3$) δ 7.39-7.61 (m, 5H), 7.19 (d, J=8.6 Hz, 2H), 6.99 (d, J=8.5 Hz, 2H), 6.60-6.63 (m, 1H), 6.39-6.42 (m, 1H), 6.15 (t, J=3.1 Hz, 1H), 3.98 (s, 1H), 3.75-3.85 (m, 1H), 3.58-3.67 (m, 1H), 3.31-3.44 (m, 2H), 3.26 (s, 3H), 3.16 (s, 3H), 1.95-2.22 (m, 2H), 1.39-1.56 (m, 1H), 0.90-1.05 (m, 1H), 0.87 (t, J=7.2 Hz, 3H). Mass Spectrum (ESI) m/e=465.2 (M+23).

The starting material, N-methoxyethyl-2-butyrylpyrrole, was prepared as follows:

To a solution of 150 mg (0.90 mmol) of N-methoxyethyl-2-acetylpyrrole in 6 mL THF at −78° C. was added dropwise 990 μL (0.99 mmol) of a 1.0 M solution of LHMDS in THF and the resultant mixture was stirred for 30 min. After this time, 108 μL (1.35 mmol) of EtI was added dropwise and the mixture was warmed to 0° C. and stirred for 2.5 h, then was farther warmed to room temperature and stirred for an additional 2.5 h. After this time, 43 μL (0.54 mmol) of EtI was added and the mixture was stirred for an additional 1 h. The reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (pure hexanes grading to hexanes:EtOAc, 9:1) to give the title compound.

$^1$H-NMR (CDCl$_3$) δ 7.00 (dd, J=4.0 Hz, 1.6 Hz, 1H), 6.92 (t, J=2.0 Hz, 1H), 6.13 (dd, J=4.0 Hz, 2.5 Hz, 1H), 4.50 (t, J=5.1 Hz, 2H), 3.65 (t, J=5.1 Hz, 2H), 3.29 (s, 3H), 2.75 (t, J=7.3 Hz, 2H), 1.67-1.78 (m, 2H), 0.97 (t, J=7.4 Hz, 3H). Mass Spectrum (ESI) m/e=164.1 (M−31).

Example 86

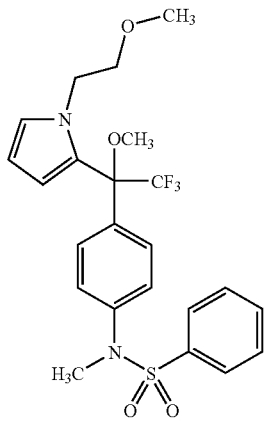

86

N-(4-{1-[1-(2-Methoxyethyl)-1H-pyrrol-2-yl]-2,2,2-trifluoro-1-methoxyethyl}-phenyl)-N-methyl-benzenesulfonamide To a suspension of 3.8 mg of NaH (0.10 mmol) in 3 mL of DMF at 0° C. was added 32 mg of N-(4-{1-[1-(2-methoxyethyl)-1H-pyrrol-2-yl]-2,2,2-trifluoro-1-hydroxyethyl}-phenyl)-N-methyl-benzenesulfonamide (Example 79, 0.068 mmol) and the reaction mixture was stirred at 0° C. for 35 min. 6 μL of iodomethane (0.089 mmol) was added and the reaction mixture allowed to warm to room temperature and stirred for 2.5 h. The reaction was quenched by the addition of a saturated aqueous solution of ammonium chloride and the aqueous layer was extracted with ethyl acetate. The combined organic layers were washed with brine, dried over MgSO$_4$, filtered and the filtrate was concentrated. The residue was purified by chromatography (silica, hexanes:EtOAc, 9:1) to give the title compound.

$^1$H-NMR (CDCl$_3$) δ 3.10-3.13 (m, 2H), 3.19 (s, 3H), 3.23 (s, 3H), 3.39 (s, 3H), 3.63-3.67 (m, 2H), 6.21-6.22 (m, 1H), 6.56 (s\m, 1H), 6.69 (m, 1H), 6.89 (m, 2H), 7.28-7.59 (m, 7H). Mass Spectrum (CI+) m/e=505.1 (M+1).

Example 87

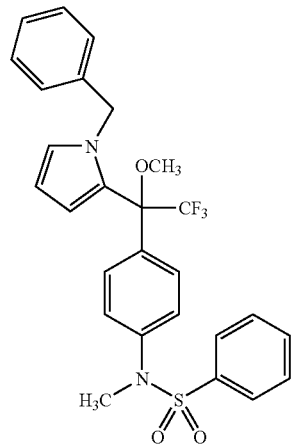

87

N-(4-{1-[1-Benzyl-1H-pyrrol-2-yl]-2,2,2-trifluoro-1-methoxyethyl}-phenyl)-N-methyl-benzenesulfonamide The title compound was prepared in a manner similar to that described in Example 86.

$^1$H-NMR (CDCl$_3$) δ 3.12 (s, 3H), 3.23 (s, 3H), 3.24 (s, 3H), 4.50 and 4.56 (AB, 2H, J=14.8 Hz), 6.18 (m, 1H), 6.55-6.60 (m, 2H), 6.86 (m, 2H), 7.00 (m, 2H), 7.18-7.52 (m, 10H). Mass Spectrum (CI+) m/e=515 (M+1).

Example 88

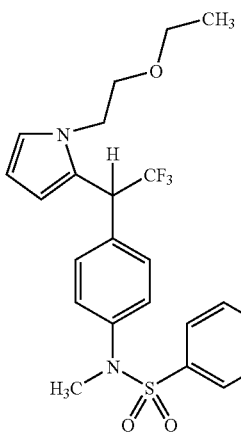

88

N-(4-{1-[1-(2-Ethoxyethyl)-1H-pyrrol-2-yl]-2,2,2-trifluoroethyl}-phenyl)-N-methyl-benzenesulfonamide To a solution of 32 mg (0.07 mmol) of N-(4-{1-[1-(2-ethoxyethyl)-1H-pyrrol-2-yl]-2,2,2-trifluoro-1-hydroxy ethyl}-phenyl)-N-methyl-benzenesulfonamide (Example 78) in 2 mL of CH$_2$Cl$_2$ at 0° C. were added 1.05 mL (6.57 mmol) of triethylsilane followed by 167 µL (1.32 mmol) of boron trifluoride diethyl etherate dropwise. The mixture was warmed to room temperature and stirred for 1.75 h. After this time, the reaction mixture was cooled to 0° C., quenched by the addition of a saturated aqueous solution of sodium bicarbonate, allowed to warm to room temperature, and extracted with EtOAc. The combined organic layers were dried over Na$_2$SO$_4$, filtered and the filtrate was concentrated. The residue was purified by chromatography on silica gel (hexanes:EtOAc, 4:1) to give the title compound.

$^1$H-NMR (CDCl$_3$) δ 7.50-7.61 (m, 3H), 7.41-7.49 (m, 2H), 7.22-7.28 (m, 2H), 7.07 (d, J=8.3 Hz, 2H), 6.66 (s, 1H), 6.32 (s, 1H), 6.18 (t, J=3.2 Hz, 1H), 5.06 (q, J$_{C-F}$=9.2 Hz, 1H), 3.79-3.83 (m, 2H), 3.31-3.57 (m, 4H), 3.14 (s, 3H), 1.13 (t, J=7.0 Hz, 3H). Mass Spectrum (ESI) m/e=489.1 (M+23).

Example 89

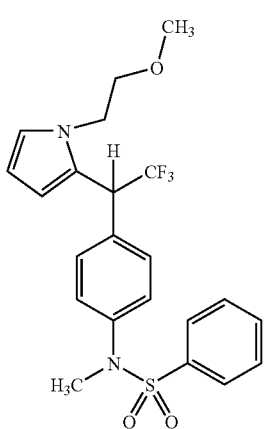

N-(4-{1-[1-(2-Methoxyethyl)-1H-pyrrol-2-yl]-2,2,2-trifluoroethyl}-phenyl)-N-methyl-benzenesulfonamide The title compound was prepared from N-(4-{1-[1-(2-methoxyethyl)-1H-pyrrol-2-yl]-2,2,2-trifluoro-1-hydroxyethyl}-phenyl)-N-methyl-benzenesulfonamide (Example 79) following the procedure described in Example 88.

$^1$H-NMR (CDCl$_3$) δ 7.51-7.59 (m, 3H), 7.43 (t, J=7.7 Hz, 2H), 7.27 (d, J=8.6 Hz, 2H), 7.08 (d, J=8.4 Hz, 2H), 6.66 (dd, J=2.6 Hz, 2.0 Hz, 1H), 6.32 (s, 1H), 6.17 (t, J=3.1 Hz, 1H), 4.95 (q, J$_{C-F}$=9.2 Hz, 1H), 3.82-3.86 (m, 2H), 3.37-3.47 (m, 2H), 3.24 (s, 3H), 3.15 (s, 3H). Mass Spectrum (ESI) m/e=475.1 (M+23).

Example 90

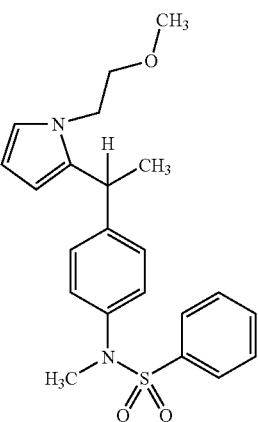

N-(4-{1-[1-(2-Methoxyethyl)-1H-pyrrol-2-yl]-ethyl}-phenyl)-N-methyl-benzenesulfonamide The title compound was prepared from N-(4-{1-hydroxy-1-[1-(2-methoxyethyl)-1H-pyrrol-2-yl]-ethyl}-phenyl)-N-methyl-benzenesulfonamide (Example 83) following the procedure described in Example 88.

$^1$H-NMR (CDCl$_3$) δ 7.51-7.60 (m, 3H), 7.43 (t, J=7.8 Hz, 2H), 7.04 (d, J=8.4 Hz, 2H), 6.98 (d, J=8.5 Hz, 2H), 6.65 (s, 1H), 6.13 (t, J=3.4 Hz, 1H), 6.10-6.13 (m, 1H), 4.06-4.13 (m, 1H), 3.68-3.82 (m, 2H), 3.27 (t, J=5.9 Hz, 2H), 3.21 (s, 3H), 3.13 (s, 3H), 1.57 (t, J=7.2 Hz, 3H). Mass Spectrum (ESI) m/e=421.1 (M+23).

Example 91

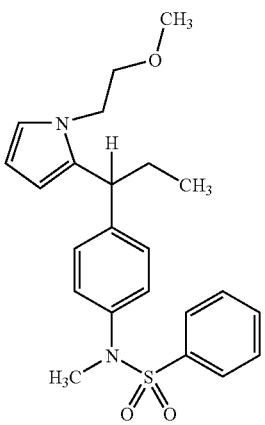

N-(4-{1-[1-(2-Methoxyethyl)-1H-pyrrol-2-yl]-propyl}-phenyl)-N-methyl-benzenesulfonamide The title compound was prepared from N-(4-{1-hydroxy-1-[1-(2-methoxyethyl)-1H-pyrrol-2-yl]-propyl}-phenyl)-N-methyl-benzenesulfonamide (Example 84) following the procedure described in Example 88.

$^1$H-NMR (CDCl$_3$) δ 7.00 (dd, J=4.0 Hz, 1.7 Hz, 1H), 6.92 (t, J=2.1 Hz, 1H), 6.13 (dd, J=4.1 Hz, 2.5 Hz, 1H), 4.50 (t,

J=5.1 Hz, 2H), 3.65 (t, J=5.2 Hz, 2H), 3.29 (s, 3H), 2.81 (q, J=7.4 Hz, 2H), 1.17 (t, J=7.4 Hz, 3H). Mass Spectrum (ESI) m/e=150.1 (M−31).

Example 92

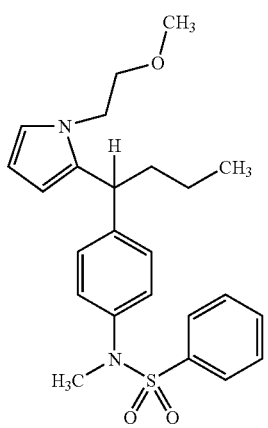

N-(4-{1-[1-(2-Methoxyethyl)-1H-pyrrol-2-yl]-butyl}-phenyl)-N-methyl-benzenesulfonamide The title compound was prepared from N-(4-{1-hydroxy-1-[1-(2-methoxyethyl)-1H-pyrrol-2-yl]-butyl}-phenyl)-N-methyl-benzenesulfonamide (Example 85) following the procedure described in Example 88.

$^1$H-NMR (CDCl$_3$) δ 7.50-7.61 (m, 3H), 7.40-7.47 (m, 2H), 7.05 (d, J=8.5 Hz, 2H), 6.97 (d, J=8.4 Hz, 2H), 6.62 (t, J=2.2 Hz, 1H), 6.10-6.17 (m, 2H), 3.71-3.92 (m, 3H), 3.25 (t, J=6.2 Hz, 2H), 3.21 (s, 3H), 3.13 (s, 3H), 1.96-2.07 (m, 1H), 1.74-1.86 (m, 1H), 1.21-1.42 (m, 2H), 0.91 (t, J=7.3 Hz, 3H). Mass Spectrum (ESI) m/e=449 (M+23).

Example 93

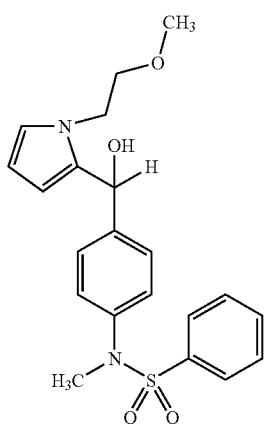

N-(4-{1-Hydroxy-1-[1-(2-methoxyethyl)-1H-pyrrol-2-yl]-methyl}-phenyl)-N-methyl-benzenesulfonamide Step A. N-Methoxyethylpyrrole-2-carboxaldehyde To a suspension of 450 mg (11.25 mmol) of NaH (60% dispersion in mineral oil) in 30 mL DMF at 0° C. was added 990 mg (10.41 mmol) of pyrrole-2-carboxaldehyde and the mixture was stirred at 0° C. for 1.5 h. After this time, 1.03 mL (10.96 mmol) of 2-bromomethyl methyl ether was added and the mixture was warmed to 50° C. and stirred for 2.75 h. The reaction mixture was allowed to cool to room temperature, quenched by the addition of a saturated aqueous solution of ammonium chloride, and extracted with EtOAc. The organic layer was washed with water and brine, dried over Na$_2$SO$_4$, filtered and the filtrate was concentrated. The residue was purified by chromatography on silica gel (hexanes:EtOAc, 9:1) to give the title compound.

$^1$H-NMR (CDCl$_3$) δ 9.53 (d, J=1.0 Hz, 1H), 7.03 (s, 1H), 6.95 (dd, J=4.0 Hz, 1.7 Hz, 1H), 6.23 (dd, J=4.0 Hz, 2.5 Hz, 1H), 4.50 (t, J=5.1 Hz, 2H), 3.66 (t, J=5.1 Hz, 2H), 3.29 (s, 3H). Mass Spectrum (ESI) m/e=122 (M−31).

Step B. N-(4-{1-Hydroxy-1-[1-(2-methoxyethyl)-1H-pyrrol-2-yl]-methyl}-phenyl)-N-methyl-benzenesulfonamide To a solution of 1.49 g (4.59 mmol) of N-(4-bromophenyl)-N-methyl benzenesulfonamide (Example 78, Step C) in 37.5 mL THF at −78° C. was added dropwise 5.94 mL (10.10 mmol) of a 1.7 M solution of tert-BuLi in pentane and the resultant mixture was stirred at −78° C. for 15 min. To this mixture was then added a solution of 1.01 g (6.59 mmol) of N-methoxyethylpyrrole-2-carboxaldehyde in 6 mL THF and the mixture was allowed to gradually warm to −30° C. over a 4 h period. After this time, the reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (hexanes:EtOAc, 13:7) to give the title compound.

$^1$H-NMR (CDCl$_3$) δ 7.52-7.64 (m, 3H), 7.45 (t, J=7.6 Hz, 2H), 7.38 (d, J=8.3 Hz, 2H), 7.06 (d, J=8.3 Hz, 2H), 6.70 (s, 1H), 6.09 (t, J=2.6 Hz, 1H), 5.85 (s, 1H), 5.65 (t, J=1.6 Hz, 1H), 4.03-4.21 (m, 3H), 3.60-3.71 (m, 2H), 3.35 (s, 3H), 3.19 (s, 3H). Mass Spectrum (ESI) m/e=423.1 (M+23).

Example 94

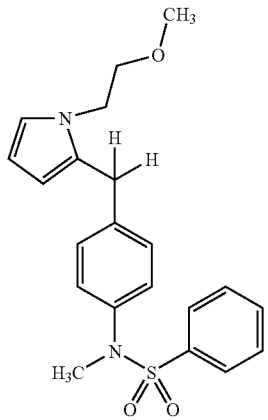

N-(4-{1-[1-(2-methoxyethyl)-1H-pyrrol-2-yl]-methyl}-phenyl)-N-methyl-benzenesulfonamide To a solution of 16 mg (0.04 mmol) of N-(4-{1-hydroxy-1-[1-(2-methoxyethyl)-1H-pyrrol-2-yl]-methyl}-phenyl)-N- methyl-benzenesulfonamide (Example 93) in 1.5 mL $CH_2Cl_2$ at 0° C. were added 620 μL (3.88 mmol) of triethylsilane followed by 100 μL (0.79 mmol) of boron trifluoride diethyl etherate dropwise. The mixture was warmed to room temperature and stirred for 2.5 h. After this time, the reaction mixture was cooled to 0° C., quenched by the addition of a saturated aqueous solution of sodium bicarbonate, allowed to warm to room temperature, and extracted with EtOAc. The combined organic layers were dried over $Na_2SO_4$, filtered and the filtrate was concentrated. The residue was purified by chromatography on silica gel (hexanes:EtOAc, 3:1) to give the title compound.

$^1$H-NMR (CDCl$_3$) δ 7.52-7.60 (m, 3H), 7.45 (t, J=7.7 Hz, 2H), 7.09 (d, J=8.4 Hz, 2H), 7.00 (d, J=8.4 Hz, 2H), 6.68 (t, J=2.0 Hz, 1H), 6.10 (t, J=3.1 Hz, 1H), 5.85 (s, 1H), 3.95 (s, 2H), 3.88 (t, J=5.8 Hz, 2H), 3.45 (t, J=5.8 Hz, 2H), 3.27 (s, 3H), 3.16 (s, 3H). Mass Spectrum (ESI) m/e=407.1 (M+23).

What is claimed is:

1. A compound having the formula:

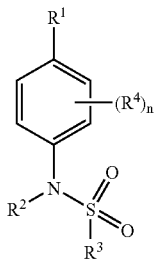

wherein
R$^1$ is

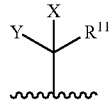

wherein
R$^{11}$ is a member selected from the group consisting of phenyl, pyridyl, pyridazinyl, pyrrolyl, imidazolyl, thiazolyl, oxazolyl, tetrazolyl, indolyl, benzimidazolyl, benzothienyl and benzothiazolyl, each of said R$^{11}$ groups being optionally substituted with from one to five substituents independently selected from the group consisting of halogen, cyano, nitro, (C$_1$-C$_8$)alkyl, (C$_2$-C$_8$)heteroalkyl, (C$_1$-C$_8$)haloalkyl, phenyl(C$_1$-C$_6$)alkyl and phenyl(C$_2$-C$_6$)heteroalkyl;
X is OH; and
Y is fluoro(C$_1$-C$_4$)alkyl;
R$^2$ is a member selected from the group consisting of H, (C$_1$-C$_8$)alkyl, (C$_2$-C$_8$)heteroalkyl, (C$_3$-C$_8$)alkenyl, (C$_3$-C$_8$)alkynyl, (C$_3$-C$_8$)cycloalkyl and (C$_4$-C$_8$)cycloalkyl-alkyl, wherein any alkyl portions of R$^2$ are optionally substituted with from one to three substituents independently selected from halogen, nitro, cyano, hydroxy, oxo and amino, or optionally R$^2$ is combined with R$^4$ to form a five- to six-membered fused ring containing from 1 to 3 heteroatoms selected from the group consisting of N, O and S;
R$^3$ is a member selected from the group consisting of aryl and heteroaryl, said aryl or heteroaryl group being optionally substituted with from one to five substituents independently selected from the group consisting of halogen, cyano, nitro, R$^{16}$, OR$^{16}$, SR$^{16}$, COR$^{16}$, CO$_2$R$^{16}$, NHR$^{16}$, N(R$^{16}$)$_2$, CONHR$^{16}$, CON(R$^{16}$)$_2$, NHSO$_2$R$^{16}$, NHC(O)R$^{16}$, phenyl, phenyl(C$_1$-C$_8$)alkyl, and phenyl(C$_2$-C$_8$)heteroalkyl; wherein each R$^{16}$ is independently selected from (C$_1$-C$_8$)alkyl, (C$_3$-C$_8$)alkenyl, (C$_3$-C$_8$)alkynyl, (C$_2$-C$_8$)heteroalkyl and halo(C$_1$-C$_8$)alkyl, or two R$^{16}$ groups attached to the same nitrogen atom are combined to form a five- to eight-membered ring;
the subscript n is an integer of from 0 to 3; and
each R$^4$ is independently selected from the group consisting of halogen, cyano, nitro, R$^{17}$, OR$^{17}$, SR$^{17}$, COR$^{17}$, CO$_2$R$^{17}$, N(R$^{17}$)$_2$ and CON(R$^{17}$)$_2$, wherein each R$^{17}$ is independently selected from H, (C$_1$-C$_8$)alkyl, (C$_3$-C$_8$)alkenyl, (C$_3$-C$_8$)alkynyl, (C$_2$-C$_8$)heteroalkyl and halo(C$_1$-C$_8$)alkyl, or two R$^{17}$ groups attached to the same nitrogen atom are combined to form a five- to eight-membered ring; and pharmaceutically acceptable salts thereof.

2. A compound of claim 1, wherein R$^{11}$ is phenyl, optionally substituted with from one to two substituents independently selected from the group consisting of halogen, cyano, nitro, (C$_1$-C$_8$)alkyl, (C$_2$-C$_8$)heteroalkyl, (C$_1$-C$_8$)haloalkyl, phenyl(C$_1$-C$_6$)alkyl and phenyl(C$_2$-C$_6$)hetroalkyl.

3. A compound of claim 2, wherein R$^2$ is a member selected from the group consisting of H, (C$_1$-C$_8$)alkyl, (C$_3$-C$_8$)cycloalkyl and (C$_4$-C$_8$)cycloalkyl-alkyl, wherein any alkyl portions of R$^2$ are optionally substituted with from one to three substituents independently selected from halogen, nitro, cyano, hydroxy, oxo and amino.

4. A compound of claim 3, wherein R$^3$ is a member selected from the group consisting of phenyl, pyridyl, thienyl and thiazolyl, optionally substituted with from one to five substituents independently selected from the group consisting of halogen, cyano, nitro, R$^{16}$, OR$^{16}$, SR$^{16}$, COR$^{16}$, CO$_2$R$^{16}$, NHR$^{16}$, N(R$^{16}$)$_2$, CONHR$^{16}$, CON(R$^{16}$)$_2$, NHSO$_2$R$^{16}$, NHC(O)R$^{16}$, phenyl, phenyl(C$_1$-C$_8$)alkyl, and phenyl(C$_2$-C$_8$)heteroalkyl; wherein each R$^{16}$ is independently selected from (C$_1$-C$_8$)alkyl, (C$_3$-C$_8$)alkenyl, (C$_3$-C$_8$)alkynyl, (C$_2$-C$_8$)heteroalkyl and halo(C$_1$-C$_8$)alkyl, or two R$^{16}$ groups attached to the same nitrogen atom are combined to form a five- to eight-membered ring.

5. A compound of claim 4, wherein the subscript n is an integer of from 0 to 2, and each R$^4$ is independently selected from the group consisting of halogen, (C$_1$-C$_8$)alkyl and halo(C$_1$-C$_8$)alkyl.

6. A compound of claim 1, wherein R$^{11}$ is pyrrolyl, optionally substituted with from one to two substituents independently selected from the group consisting of halogen, cyano, nitro, (C$_1$-C$_8$)alkyl, (C$_2$-C$_8$)heteroalkyl, (C$_1$-C$_8$) haloalky, phenyl(C$_1$-C$_6$)alkyl and phenyl(C$_2$-C$_6$)hetroalkyl.

7. A compound of claim 6, wherein R$^2$ is a member selected from the group consisting of H, (C$_1$-C$_8$)alkyl, (C$_3$-C$_8$)cycloalkyl and (C$_4$-C$_8$)cycloalkyl-alkyl, wherein any alkyl portions of R$^2$ are optionally substituted with from one to three substituents independently selected from halogen, nitro, cyano, hydroxy, oxo and amino.

8. A compound of claim 7, wherein R$^3$ is a member selected from the group consisting of phenyl, pyridyl, thienyl and thiazolyl, optionally substituted with from one to five substituents independently selected from the group consisting of halogen, cyano, nitro, R$^{16}$, OR$^{16}$, SR$^{16}$, COR$^{16}$, CO$_2$R$^{16}$, NHR$^{16}$, N(R$^{16}$)$_2$, CONHR$^{16}$, CON(R$^{16}$)$_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{16}$ groups attached to the same nitrogen atom are combined to form a five- to eight-membered ring.

9. A compound of claim 8, wherein the subscript n is an integer of from 0 to 2, and each $R^4$ is independently selected from the group consisting of halogen, ($C_1$-$C_8$)alkyl and halo($C_1$-$C_8$)alkyl.

* * * * *